United States Patent
Vlasenko et al.

(10) Patent No.: US 7,354,743 B2
(45) Date of Patent: Apr. 8, 2008

(54) METHODS FOR DEGRADING LIGNOCELLULOSIC MATERIALS

(75) Inventors: Elena Vlasenko, Davis, CA (US); Joel Cherry, Davis, CA (US); Feng Xu, Davis, CA (US)

(73) Assignee: Novozymes, Inc., Davis, CA (US)

( * ) Notice: Subject to any disclaimer, the term of this patent is extended or adjusted under 35 U.S.C. 154(b) by 25 days.

(21) Appl. No.: 11/036,871

(22) Filed: Jan. 14, 2005

(65) Prior Publication Data

US 2005/0164355 A1 Jul. 28, 2005

Related U.S. Application Data

(60) Provisional application No. 60/537,452, filed on Jan. 16, 2004.

(51) Int. Cl.
*C12P 19/04* (2006.01)

(52) U.S. Cl. ............... 435/101; 435/200; 435/209; 435/277

(58) Field of Classification Search .......... 435/99, 435/262, 274, 277, 278, 101, 200, 209; 162/5, 162/70, 72, 77
See application file for complete search history.

(56) References Cited

U.S. PATENT DOCUMENTS

| | | | |
|---|---|---|---|
| 4,539,353 A | | 9/1985 | Abel et al. |
| 5,705,369 A | * | 1/1998 | Torget et al. ............... 435/105 |
| 5,713,962 A | | 2/1998 | Scialla et al. |
| 5,919,691 A | * | 7/1999 | Schulein et al. ............ 435/209 |
| 5,972,872 A | * | 10/1999 | Lange et al. ................. 510/392 |
| 6,001,639 A | * | 12/1999 | Schulein et al. ............ 435/263 |
| 6,099,688 A | * | 8/2000 | Pere et al. .................... 162/24 |
| 6,387,690 B1 | * | 5/2002 | Schulein et al. ............ 435/263 |
| 2003/0124710 A1 | * | 7/2003 | Borch et al. ................. 435/262 |

OTHER PUBLICATIONS

Kaar et al., "Benefits from Tween During Enzymic Hydrolysis of Corn Stover", *Biotechnol. Bioengg.*, 1998, vol. 59, No. 4, pp. 419-427.

Kurakake M et al., "Pretreatment of Bagasse by Nonionic Surfactant for the Enzymatic Hydrolysis", *Bioresource Technology*, 1994, vol. 49, No. 3, pp. 247-251.

Park et al., "Effects of Nonionic Surfactant on Enzymatic Hydrolysis of Used Newspaper", *Biotechnol. Bioengg.*, 1992, vol. 39, No. 1, pp. 117-120.

Adams CD et al, "Biodegradation of Nonionic Surfactants and Effects of Oxidative Pretreatment", *J. Environ. Engg.*, 1996, vol. 122, No. 6, pp. 477-483.

* cited by examiner

*Primary Examiner*—Herbert J. Lilling
(74) *Attorney, Agent, or Firm*—Robert L. Starnes

(57) ABSTRACT

The present invention relates to methods for degrading a lignocellulosic material, comprising: treating the lignocellulosic material with an effective amount of one or more cellulolytic enzymes in the presence of at least one surfactant selected from the group consisting of a secondary alcohol ethoxylate, fatty alcohol ethoxylate, nonylphenol ethoxylate, tridecyl ethoxylate, and polyoxyethylene ether, wherein the presence of the surfactant increases the degradation of lignocellulosic material compared to the absence of the surfactant. The present invention also relates to methods for producing an organic substance, comprising: (a) saccharifying a lignocellulosic material with an effective amount of one or more cellulolytic enzymes in the presence of at least one surfactant selected from the group consisting of a secondary alcohol ethoxylate, fatty alcohol ethoxylate, nonylphenol ethoxylate, tridecyl ethoxylate, and polyoxyethylene ether, wherein the presence of the surfactant increases the degradation of lignocellulosic material compared to the absence of the surfactant; (b) fermenting the saccharified lignocellulosic material of step (a) with one or more fermentating microorganisms; and (c) recovering the organic substance from the fermentation.

13 Claims, 29 Drawing Sheets

ATG AAG CTT GGT TGG ATC GAG GTG GCC GCA TTG GCG GCT GCC TCA GTA GTC AGT GCC
M   K   L   G   W   I   E   V   A   A   L   A   A   A   S   V   V   S   A

Fig 7

ATG CGT TCC TCC CCC CTC CTC CGC TCC GCC GTT GTG GCC GCC CTG CCG GTG TTG GCC CTT GCC
 M   R   S   S   P   L   L   R   S   A   V   V   A   A   L   P   V   L   A   L   A

Fig. 8

```
ATGAGATTCGGTTGGCTCGAGGTGGCCGGCTTCTGACGGCCGCTTCTGTAGCCAATGCCCAGGTTTGTGATGCCTTTCCCGTCATTGTTTCGGATATAGTTGA  100
 M  R  F  G  W  L  E  V  A  A  L  T  A  A  S  V  A  N  A  Q
CAATAGTCATGGAAATAATCAGGAATTGGCTTTCTCCACCATTCTCGCCTTGGCTGATGGCCAGGAGAGTGGGCAGATGCCCATCGACGC  200
                E  L  A  F  S  P  F  Y  P  S  P  W  A  D  G  Q  G  E  W  A  D  A  H  R  R
GCCGTCGAGATCGTTTCTCAGATGACACTGGCGGAGAAGGTTAACCTTACAACGGGTACTGGTGGGTTGCGACTTTTTTGTTGACAGTGAGCTTTCTC  300
 A  V  E  I  V  S  Q  M  T  L  A  E  K  V  N  L  T  T  G  T  G
ACTGACCATCTACACAGATGGGAAATGGACCGATGCGTCGTCAAACCGGCAGCGTTCCCAGTAAGCTTGCAATTCTGCAACAACGTGCAAGTGTAGTT  400
             W  E  M  D  R  C  V  G  Q  T  G  S  V  P  R
GCTAAAACGCGTGGTGCAGATTGGTCATCAACTGGGGTCTTTGTGGCCAGGAATTCCCCTTTGGGCTATACCGTTCTGAGCTATAATGTGCCGGAGTCTTT  500
               L  G  I  N  W  G  L  C  G  Q  D  S  P  L  G  I  R  F
CAGTCCCTTGTATTATGTCGTGATGATTGTCTCTGTATAGCTGACCTCAACTCCGCCTTCCCTGCTGGTACTAATGTCGCCGGACATGGACAAGACACT  600
                 S  D  L  N  S  A  F  P  A  G  T  N  V  A  A  T  W  D  K  T  L
CGCCTACCTTCGTGGCAAGGCCATGGGTGAGGAATTCAACGACAAGGGCGTGGACATTTTGCTGGGGCCTGCTGTCTCTCGCCAAATACCCGGAC  700
 A  Y  L  R  G  K  A  M  G  E  E  F  N  D  K  G  V  D  I  L  L  G  P  A  A  G  P  L  G  K  Y  P  D
GGGCCAGAATCTGGGAAGGCTTCTCTCCTGATCCGGTTCTCACTGTGTACTTTTGCCGAAACTATCAAGGGTATCAAGACGCGGGTGTGATTGCTA  800
 G  G  R  I  W  E  G  F  S  P  D  D  P  V  L  T  G  V  L  F  A  E  T  I  K  G  I  Q  D  A  G  V  I  A
CTGCCAAGCATTACATTCTGAATGAACAGGAGCATTTCCGACAGTTGGCGAGGGCCAGGAGATGGTTACAACATCGGAGACGATCAGCTCCAACGT  900
 T  A  K  H  Y  I  L  N  E  Q  E  H  F  R  Q  V  G  E  A  Q  G  Y  N  I  T  E  T  I  S  S  N  V
GGATGACAAGACCATGCACGAGTTGTACTTTGGTGAGTAGTTGACACTGCAAATGAGGACCTTGATTGATTTGACTGACCTGGAATGCAGGCCCTTTGC  1000
 D  D  K  T  M  H  E  L  Y  L  W                                                              P  F  A
AGATGCTGCGCGGTAAGATTTCCGTAGACTTGACCTCGCCGACGAACCATCGTAGCTGGGCTTGAGCTGGCTGGCCTCGTCATGTGTTCCTA  1100
 D  A  V  R                                                             A  G  V  G  A  V  M  C  S  Y
CAATCAAATCAACAACGGTACGTTGTCAAAACAGTCTCAAACTCTCAACAAGCTCTCCTCAAGGCTTCGGGCTTCCAAGGCTTCGTCATGAGTGACTGG  1200
 N  Q  I  N  N  S  Y  G  C  Q  N  S  Q  T  L  N  K  L  L  K  A  E  L  G  F  Q  G  F  V  M  S  D  W
AGCGCTCACCACGGCGGTGTCGGCGCTCGCGCTCGGGTTGGATATGTCGATGATATGTCGATGATATCCTTCGACGAGACATTTCCTTCGACGACGACGA  1300
 S  A  H  H  S  G  V  G  A  A  L  A  G  L  D  M  S  M  P  G  D  I  S  F  D  D  G  L  S  F  W  G  T
ACCTAACTGTCAGTGTTCTTAACGGCACCGTTCCAGCGTGCATGGATGACATGGCTGTCGATCATGACCGGCTACTACAAGGTTGGTCGTGACCG  1400
 N  L  T  V  S  V  L  N  G  T  V  P  A  W  R  V  D  D  M  A  V  R  I  M  T  A  Y  Y  K  V  G  R  D  R
TCTTCGTATTCCCCTAACTTCAGTCTCAGATCATCCGTGAGATTGGTGCCGCTAGTACAGTGCTCTTGAAGAACACGGGTGTCTTCCTTTGACCGGCAAGG  1500
 L  R  I  P  P  N  F  S  S  W  T  R  D  E  Y  G  W  E  H  S  A  V  S  E  G  A  W  T  K  V  N  D  F
GTCAATGTGCAGCCAGTCACTCTGAGATCATCCGTGTTCTGAAGAACACGGGTGTCTTCTTTGACCGGCAAGG  1600
 V  N  V  Q  R  S  H  S  Q  I  I  H  R  E  I  G  A  A  S  T  V  L  K  N  T  G  A  L  P  L  T  G  K
AGGTTAAAGTGGGTGTTCTCGGTGAAGACGTCTTCCCAACTTCCCTTACCTTGTCATGCTAAGTCCAACGCGCGGGTGTGTAACGGCCACTCTTTGTATGGC  1700
 E  V  K  V  G  V  L  G  E  D  A  G  S  N  P  W  G  A  N  G  C  P  D  R  G  C  D  N  G  T  L  A  M  A
CTGGGGTAGTGCACTACTGCCGCCAACTTCCCTTACCTTGTCATCCAGCAGGCTATCATCAGCAACGCGGCAATGTCTTTGCTGTGACT  1800
 W  G  S  G  T  A  N  F  P  Y  L  V  T  P  E  Q  A  I  Q  R  E  V  I  S  N  G  G  N  V  F  A  V  T
GATAACGGGCTCTCAGCCAGATGTTGCATCATCAGGCAGATGTTGCGGGGCTCTTAGAAAAAAGAACGTTCTGAATGAAGTTTTTAACCA  1900
 D  N  G  A  L  S  Q  M  A  D  V  A  S  Q  S  S
```

Fig. 10A

```
TTGCGAACACGCGTGTCTTTGGTGTTTGTCAACGCCGACTCTGGAGAGGGTTTCATCAGTGTCGACGGCAACGAGGGTGACCGCAACGAGGGTGACCGCAAAAATCTCACTCTGTG  2000
  V  S  L  V  F  V  N  A  D  S  G  E  G  F  I  S  V  D  G  N  E  G  D  R  K  N  L  T  L  W
GAAGAACGGCGAGGCCGGTCATTGACACTGTTGTCAGCCACTGTCAACAACACGATTGTGGTTATTCACAGTTGTGGGCCCGTCTTGATCGACCGGTGGTAT  2100
  K  N  G  E  A  V  I  D  T  V  V  S  H  C  N  N  T  I  V  V  I  H  S  V  G  P  V  L  I  D  R  W  Y
GATAACCCCAACGTCACTGCCATCATCTGGGCAGCTTGCCCCGGTCAGGAGAGTGGCAACTCCCTGGTCGACGTGCTCTATGGCCGGTCAACCCCAGCG  2200
  D  N  P  N  V  T  A  I  I  W  A  G  L  P  G  Q  E  S  G  N  S  L  V  D  V  L  Y  G  R  V  N  P  S
CCAAGACCCCGTTCACCTGGGGCAAGACTCGGGAGTCTTACGGCCAGTCTCCCTGCTCACCGAGCTAACAATGGTGCTCCCCAGGATGATTCAA  2300
  A  K  T  P  F  T  W  G  K  T  R  E  S  Y  G  A  P  L  T  E  P  N  N  G  N  G  A  P  Q  D  D  F  N
CGAGGGCGTCTTCATTGACTACCGTCACTTTGACAAGCGCAATGAGACGCCCATTTATGAGTTTGCCATGGCTTGAGCTACACCACCTTTGGTTACTCT  2400
  E  G  V  F  I  D  Y  R  H  F  D  K  R  N  E  T  P  I  Y  E  F  G  H  G  L  S  Y  T  T  F  G  Y  S
CACCTTCGGGTTCAGGCCCCTCAATAGTTCGGCCATATGTCCCGACTAGCGGAGAGACCAAGCTGCCCAACCTATGGTGAGATCGGTAGTGCCG  2500
  H  L  R  V  Q  A  L  N  S  S  S  A  Y  V  P  T  S  G  E  T  K  P  A  P  T  Y  G  E  I  G  S  A
CCGACTACCTGTATCCCGAGGGTCTCAAAAGAATTACCAAGTTTAAGTTCATCTACCCTTGGCTCAACTGAGATTCTTCTGACGACCCGAACTA  2600
  A  D  Y  L  Y  P  E  G  L  K  R  I  T  K  F  I  Y  P  W  L  N  S  T  D  L  E  D  S  D  D  P  N  Y
CGGCTGGGAGGACTCGGAGTACATTCCCGAAGGCGTCAGGGATGGCTCCCTCCTGAAGGCTGGCGCTCCGGTGGTAACCCTACCCTT  2700
  G  W  E  D  S  E  Y  I  P  E  G  A  R  D  G  S  P  Q  P  L  L  K  A  G  G  A  P  G  G  N  P  T  L
TATCAGGATCTTGTTAGGGTCGCCTTCTAGTATGTTTCACTGGGGCGACCGAACGAGCCTCGTTCTGCCAAGTTCGACCGAATCTTCCTGGCTCCTGG  2800
  Y  Q  D  L  V  R  V  S  A  T  I  T  N  T  G  N  V  A  G  Y  E  V  P  Q  L
TTGCAATTTGGCTAACTCGCTTCTAGTATGTTTCACTGGGGCGACCGAACGAGCCTCGTTCTGCCAAGTTCGACCGAATCTTCCTGGCTCCTGG  2900
  Y  V  S  L  G  G  P  N  E  P  R  V  V  L  R  K  F  D  R  I  F  L  A  P  G
GGAGCAAAAGGTTTGGACCACGTCCTAACCGACTCTTAACCGTCGTGATCTCGCGTGATCTCGCCGTCATCACAAAGTACCCCAAGAAAGTG  3000
  E  Q  K  V  W  T  T  L  N  R  D  L  A  N  W  D  V  E  A  Q  D  W  V  I  T  K  Y  P  K  K  V
CACGTCGGCAGCTCCTCGCGTAAGCTGCCTCTGAGAGCGCCTCTGCCCCGTGTCTACTAG  3060
  H  V  G  S  S  R  K  L  P  L  R  A  P  L  P  R  V  Y
```

Fig. 10B

SEQUENCE LISTING

```
<160> NUMBER OF SEQ ID NOS: 43

<210> SEQ ID NO 1
<211> LENGTH: 22
<212> TYPE: DNA
<213> ORGANISM: Aspergillus oryzae

<400> SEQUENCE: 1
gtgccccatg atacgcctcc gg                                              22

<210> SEQ ID NO 2
<211> LENGTH: 26
<212> TYPE: DNA
<213> ORGANISM: Aspergillus oryzae

<400> SEQUENCE: 2
gagtcgtatt tccaaggctc ctgacc                                          26

<210> SEQ ID NO 3
<211> LENGTH: 24
<212> TYPE: DNA
<213> ORGANISM: Aspergillus oryzae

<400> SEQUENCE: 3
ggaggccatg aagtggacca acgg                                            24

<210> SEQ ID NO 4
<211> LENGTH: 45
<212> TYPE: DNA
```

```
<213> ORGANISM: Aspergillus niger

<400> SEQUENCE: 4
caccgtgaaa gccatgctct ttccttcgtg tagaagacca gacag         45

<210> SEQ ID NO 5
<211> LENGTH: 45
<212> TYPE: DNA
<213> ORGANISM: Aspergillus niger

<400> SEQUENCE: 5
ctggtcttct acacgaagga aagagcatgg ctttcacggt gtctg         45

<210> SEQ ID NO 6
<211> LENGTH: 44
<212> TYPE: DNA
<213> ORGANISM: Aspergillus oryzae

<400> SEQUENCE: 6
ctatatacac aactggattt accatgggcc cgcggccgca gatc          44

<210> SEQ ID NO 7
<211> LENGTH: 44
<212> TYPE: DNA
<213> ORGANISM: Aspergillus oryzae

<400> SEQUENCE: 7
gatctgcggc cgcgggccca tggtaaatcc agttgtgtat atag          44

<210> SEQ ID NO 8
<211> LENGTH: 29
<212> TYPE: DNA
<213> ORGANISM: Trichoderma reesei

<400> SEQUENCE: 8
aacgttaatt aaggaatcgt tttgtgttt                           29

<210> SEQ ID NO 9
<211> LENGTH: 29
<212> TYPE: DNA
<213> ORGANISM: Trichoderma reesei

<400> SEQUENCE: 9
agtactagta gctccgtggc gaaagcctg                           29

<210> SEQ ID NO 10
<211> LENGTH: 31
<212> TYPE: DNA
<213> ORGANISM: Humicola insolens

<400> SEQUENCE: 10
ttgaattgaa aatagattga tttaaaactt c                        31

<210> SEQ ID NO 11
<211> LENGTH: 25
<212> TYPE: DNA
<213> ORGANISM: Humicola insolens

<400> SEQUENCE: 11
ttgcatgcgt aatcatggtc atagc                               25

<210> SEQ ID NO 12
<211> LENGTH: 26
```

```
<212> TYPE: DNA
<213> ORGANISM: Saccharomyces cerevisiae

<400> SEQUENCE: 12
ttgaattcat gggtaataac tgatat                                  26

<210> SEQ ID NO 13
<211> LENGTH: 32
<212> TYPE: DNA
<213> ORGANISM: Saccharomyces cerevisiae

<400> SEQUENCE: 13
aaatcaatct attttcaatt caattcatca tt                           32

<210> SEQ ID NO 14
<211> LENGTH: 45
<212> TYPE: DNA
<213> ORGANISM: Aspergillus oryzae

<400> SEQUENCE: 14
ggatgctgtt gactccggaa atttaacggt ttggtcttgc atccc             45

<210> SEQ ID NO 15
<211> LENGTH: 44
<212> TYPE: DNA
<213> ORGANISM: Aspergillus oryzae

<400> SEQUENCE: 15
ggtattgtcc tgcagacggc aatttaacgg cttctgcgaa tcgc              44

<210> SEQ ID NO 16
<211> LENGTH: 29
<212> TYPE: DNA
<213> ORGANISM: Humicola insolens

<400> SEQUENCE: 16
aagcttaagc atgcgttcct cccccctcc                               29

<210> SEQ ID NO 17
<211> LENGTH: 32
<212> TYPE: DNA
<213> ORGANISM: Humicola insolens

<400> SEQUENCE: 17
ctgcagaatt ctacaggcac tgatggtacc ag                           32

<210> SEQ ID NO 18
<211> LENGTH: 32
<212> TYPE: DNA
<213> ORGANISM: Humicola insolens

<400> SEQUENCE: 18
ctgcagaatt ctacaggcac tgatggtacc ag                           32

<210> SEQ ID NO 19
<211> LENGTH: 36
<212> TYPE: DNA
<213> ORGANISM: Humicola insolens

<400> SEQUENCE: 19
accgcggact gcgcatcatg cgttcctccc ccctcc                       36

<210> SEQ ID NO 20
```

```
<211> LENGTH: 29
<212> TYPE: DNA
<213> ORGANISM: Trichoderma reesei

<400> SEQUENCE: 20
aaacgtcgac cgaatgtagg attgttatc                                          29

<210> SEQ ID NO 21
<211> LENGTH: 17
<212> TYPE: DNA
<213> ORGANISM: Trichoderma reesei

<400> SEQUENCE: 21
gatgcgcagt ccgcggt                                                       17

<210> SEQ ID NO 22
<211> LENGTH: 29
<212> TYPE: DNA
<213> ORGANISM: Trichoderma reesei

<400> SEQUENCE: 22
aaacgtcgac cgaatgtagg attgttatc                                          29

<210> SEQ ID NO 23
<211> LENGTH: 36
<212> TYPE: DNA
<213> ORGANISM: Trichoderma reesei

<400> SEQUENCE: 23
ggagggggga ggaacgcatg atgcgcagtc cgcggt                                  36

<210> SEQ ID NO 24
<211> LENGTH: 29
<212> TYPE: DNA
<213> ORGANISM: Trichoderma reesei

<400> SEQUENCE: 24
aaacgtcgac cgaatgtagg attgttatc                                          29

<210> SEQ ID NO 25
<211> LENGTH: 32
<212> TYPE: DNA
<213> ORGANISM: Trichoderma reesei

<400> SEQUENCE: 25
ctgcagaatt ctacaggcac tgatggtacc ag                                      32

<210> SEQ ID NO 26
<211> LENGTH: 57
<212> TYPE: DNA
<213> ORGANISM: Aspergillus oryzae

<400> SEQUENCE: 26
atgaagcttg gttggatcga ggtggccgca ttggcggctg cctcagtagt cagtgcc           57

<210> SEQ ID NO 27
<211> LENGTH: 19
<212> TYPE: PRT
<213> ORGANISM: Aspergillus oryzae

<400> SEQUENCE: 27

Met Lys Leu Gly Trp Ile Glu Val Ala Ala Leu Ala Ala Ala Ser Val
1               5                   10                  15
```

-continued

Val Ser Ala

<210> SEQ ID NO 28
<211> LENGTH: 42
<212> TYPE: DNA
<213> ORGANISM: Aspergillus oryzae

<400> SEQUENCE: 28
tgccggtgtt ggcccttgcc aaggatgatc tcgcgtactc cc          42

<210> SEQ ID NO 29
<211> LENGTH: 28
<212> TYPE: DNA
<213> ORGANISM: Aspergillus oryzae

<400> SEQUENCE: 29
gactagtctt actgggcctt aggcagcg                          28

<210> SEQ ID NO 30
<211> LENGTH: 63
<212> TYPE: DNA
<213> ORGANISM: Humicola insolens

<400> SEQUENCE: 30
atgcgttcct cccccctcct ccgctccgcc gttgtggccg ccctgccggt gttggccctt   60
gcc                                                               63

<210> SEQ ID NO 31
<211> LENGTH: 21
<212> TYPE: PRT
<213> ORGANISM: Humicola insolens

<400> SEQUENCE: 31

Met Arg Ser Ser Pro Leu Leu Arg Ser Ala Val Val Ala Ala Leu Pro
1               5                   10                  15

Val Leu Ala Leu Ala
            20

<210> SEQ ID NO 32
<211> LENGTH: 30
<212> TYPE: DNA
<213> ORGANISM: Aspergillus oryzae

<400> SEQUENCE: 32
acgcgtcgac cgaatgtagg attgttatcc                        30

<210> SEQ ID NO 33
<211> LENGTH: 42
<212> TYPE: DNA
<213> ORGANISM: Aspergillus oryzae

<400> SEQUENCE: 33
gggagtacgc gagatcatcc ttggcaaggg ccaacaccgg ca          42

<210> SEQ ID NO 34
<211> LENGTH: 31
<212> TYPE: DNA
<213> ORGANISM: Aspergillus fumigatus

<400> SEQUENCE: 34
actggattta ccatgagatt cggttggctc g                      31

<210> SEQ ID NO 35
<211> LENGTH: 31
<212> TYPE: DNA
<213> ORGANISM: Aspergillus fumigatus

<400> SEQUENCE: 35
agtcacctct agttactagt agacacgggg c                             31

<210> SEQ ID NO 36
<211> LENGTH: 3060
<212> TYPE: DNA
<213> ORGANISM: Aspergillus fumigatus

<400> SEQUENCE: 36

| | | | | | |
|---|---|---|---|---|---|
| atgagattcg | gttggctcga | ggtggccgct | ctgacggccg | cttctgtagc | caatgcccag | 60 |
| gtttgtgatg | ctttcccgtc | attgtttcgg | atatagttga | caatagtcat | ggaaataatc | 120 |
| aggaattggc | tttctctcca | ccattctacc | cttcgccttg | ggctgatggc | cagggagagt | 180 |
| gggcagatgc | ccatcgacgc | gccgtcgaga | tcgtttctca | gatgacactg | gcggagaagg | 240 |
| ttaaccttac | aacgggtact | gggtgggttg | cgactttttt | gttgacagtg | agctttcttc | 300 |
| actgaccatc | tacacagatg | gaaatggac | cgatgcgtcg | gtcaaaccgg | cagcgttccc | 360 |
| aggtaagctt | gcaattctgc | aacaacgtgc | aagtgtagtt | gctaaaacgc | ggtggtgcag | 420 |
| acttggtatc | aactggggtc | tttgtggcca | ggattcccct | tgggtatcc | gtttctgtga | 480 |
| gctatacccg | cggagtcttt | cagtccttgt | attatgtgct | gatgattgtc | tctgtatagc | 540 |
| tgacctcaac | tccgccttcc | ctgctggtac | taatgtcgcc | gcgacatggg | acaagacact | 600 |
| cgcctacctt | cgtggcaagg | ccatgggtga | ggaattcaac | gacaagggcg | tggacatttt | 660 |
| gctgggcct | gctgctggtc | ctctcggcaa | atacccggac | ggcggcagaa | tctgggaagg | 720 |
| cttctctcct | gatccggttc | tcactggtgt | acttttcgcc | gaaactatca | agggtatcca | 780 |
| agacgcgggt | gtgattgcta | ctgccaagca | ttacattctg | aatgaacagg | agcatttccg | 840 |
| acaggttggc | gaggcccagg | atatggttta | caacatcacg | gagacgatca | gctccaacgt | 900 |
| ggatgacaag | accatgcacg | agttgtacct | tggtgagta | gttgacactg | caaatgagga | 960 |
| ccttgattga | tttgactgac | ctggaatgca | ggccctttgc | agatgctgtg | cgcggtaaga | 1020 |
| ttttccgtag | acttgacctc | gcgacgaaga | aatcgctgac | gaaccatcgt | agctggcgtt | 1080 |
| ggcgctgtca | tgtgttccta | caatcaaatc | aacaacagct | acggttgtca | aaacagtcaa | 1140 |
| actctcaaca | agctcctcaa | ggctgagctg | ggcttccaag | gcttcgtcat | gagtgactgg | 1200 |
| agcgctcacc | acagcggtgt | cggcgctgcc | ctcgctgggt | tggatatgtc | gatgcctgga | 1260 |
| gacatttcct | tcgacgacgg | actctccttc | tggggcacga | acctaactgt | cagtgttctt | 1320 |
| aacggcaccg | ttccagcctg | gcgtgtcgat | gacatggctg | ttcgtatcat | gaccgcgtac | 1380 |
| tacaaggttg | gtcgtgaccg | tcttcgtatt | ccccctaact | tcagctcctg | gacccgggat | 1440 |
| gagtacggct | gggagcattc | tgctgtctcc | gagggagcct | ggaccaaggt | gaacgacttc | 1500 |
| gtcaatgtgc | agcgcagtca | ctctcagatc | atccgtgaga | ttggtgccgc | tagtacagtg | 1560 |
| ctcttgaaga | acacgggtgc | tcttcctttg | accggcaagg | aggttaaagt | gggtgttctc | 1620 |
| ggtgaagacg | ctggttccaa | cccgtgggt | gctaacggct | gccccgaccg | cggctgtgat | 1680 |
| aacggcactc | ttgctatggc | ctgggtagt | ggtactgcca | acttcccttt | acttgtcacc | 1740 |
| cccgagcagg | ctatccagcg | agaggtcatc | agcaacggcg | gcaatgtctt | tgctgtgact | 1800 |
| gataacgggg | ctctcagcca | gatggcagat | gttgcatctc | aatccaggtg | agtgcgggct | 1860 |

```
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg aagaacggc gaggccgtca ttgacactgt tgtcagccac    2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgaggcgtc ttcattgact accgtcactt tgacaagcgc    2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaaccccct cctgaaggct ggcggcgctc ctggtggtaa ccctaccctt   2700
tatcaggatc ttgttagggt gtcggccacc ataaccaaca ctggtaacgt cgccggttat   2760
gaagtccctc aattggtgag tgaccccgcat gttccttgcg ttgcaatttg gctaactcgc   2820
ttctagtatg tttcactggg cggaccgaac gagcctcggg tcgttctgcg caagttcgac   2880
cgaatcttcc tggctcctgg ggagcaaaag gtttggacca cgactcttaa ccgtcgtgat   2940
ctcgccaatt gggatgtgga ggctcaggac tgggtcatca caaagtaccc caagaaagtg   3000
cacgtcggca gctcctcgcg taagctgcct ctgagagcgc tctgccccg tgtctactag    3060
```

<210> SEQ ID NO 37
<211> LENGTH: 863
<212> TYPE: PRT
<213> ORGANISM: Aspergillus fumigatus

<400> SEQUENCE: 37

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
```

-continued

```
            165                 170                 175
Ile Lys Gly Ile Gln Asp Ala Gly Val Ile Ala Thr Ala Lys His Tyr
            180                 185                 190
Ile Leu Asn Glu Gln Glu His Phe Arg Gln Val Gly Glu Ala Gln Gly
            195                 200                 205
Tyr Gly Tyr Asn Ile Thr Glu Thr Ile Ser Ser Asn Val Asp Asp Lys
            210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
            245                 250                 255
Gly Cys Gln Asn Ser Gln Thr Leu Asn Lys Leu Leu Lys Ala Glu Leu
            260                 265                 270
Gly Phe Gln Gly Phe Val Met Ser Asp Trp Ser Ala His His Ser Gly
            275                 280                 285
Val Gly Ala Ala Leu Ala Gly Leu Asp Met Ser Met Pro Gly Asp Ile
            290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
            325                 330                 335
Arg Ile Met Thr Ala Tyr Tyr Lys Val Gly Arg Asp Arg Leu Arg Ile
            340                 345                 350
Pro Pro Asn Phe Ser Ser Trp Thr Arg Asp Glu Tyr Gly Trp Glu His
            355                 360                 365
Ser Ala Val Ser Glu Gly Ala Trp Thr Lys Val Asn Asp Phe Val Asn
            370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
            405                 410                 415
Val Lys Val Gly Val Leu Gly Glu Asp Ala Gly Ser Asn Pro Trp Gly
            420                 425                 430
Ala Asn Gly Cys Pro Asp Arg Gly Cys Asp Asn Gly Thr Leu Ala Met
            435                 440                 445
Ala Trp Gly Ser Gly Thr Ala Asn Phe Pro Tyr Leu Val Thr Pro Glu
            450                 455                 460
Gln Ala Ile Gln Arg Glu Val Ile Ser Asn Gly Gly Asn Val Phe Ala
465                 470                 475                 480
Val Thr Asp Asn Gly Ala Leu Ser Gln Met Ala Asp Val Ala Ser Gln
            485                 490                 495
Ser Ser Val Ser Leu Val Phe Val Asn Ala Asp Ser Gly Glu Gly Phe
            500                 505                 510
Ile Ser Val Asp Gly Asn Glu Gly Asp Arg Lys Asn Leu Thr Leu Trp
            515                 520                 525
Lys Asn Gly Glu Ala Val Ile Asp Thr Val Val Ser His Cys Asn Asn
            530                 535                 540
Thr Ile Val Val Ile His Ser Val Gly Pro Val Leu Ile Asp Arg Trp
545                 550                 555                 560
Tyr Asp Asn Pro Asn Val Thr Ala Ile Ile Trp Ala Gly Leu Pro Gly
            565                 570                 575
Gln Glu Ser Gly Asn Ser Leu Val Asp Val Leu Tyr Gly Arg Val Asn
            580                 585                 590
```

```
Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
        850                 855                 860

<210> SEQ ID NO 38
<211> LENGTH: 26
<212> TYPE: DNA
<213> ORGANISM: Trichoderma reesei

<400> SEQUENCE: 38
actagtcgac cgaatgtagg attgtt                                              26

<210> SEQ ID NO 39
<211> LENGTH: 19
<212> TYPE: DNA
<213> ORGANISM: Trichoderma reesei

<400> SEQUENCE: 39
tgaccatggt gcgcagtcc                                                      19

<210> SEQ ID NO 40
<211> LENGTH: 26
<212> TYPE: DNA
<213> ORGANISM: Trichoderma reesei

<400> SEQUENCE: 40
```

```
cgatcgtctc cctatgggtc attacc                                          26

<210> SEQ ID NO 41
<211> LENGTH: 28
<212> TYPE: DNA
<213> ORGANISM: Trichoderma reesei

<400> SEQUENCE: 41
actagttaat taagctccgt ggcgaaag                                        28

<210> SEQ ID NO 42
<211> LENGTH: 29
<212> TYPE: DNA
<213> ORGANISM: Trichoderma reesei

<400> SEQUENCE: 42
cttcaccatg gcgccctcag ttacactgc                                       29

<210> SEQ ID NO 43
<211> LENGTH: 33
<212> TYPE: DNA
<213> ORGANISM: Trichoderma reesei

<400> SEQUENCE: 43
gccgttaatt aaggcaagtc aacgctctaa agg                                  33
```

METHODS FOR DEGRADING LIGNOCELLULOSIC MATERIALS

CROSS-REFERENCE TO RELATED APPLICATION

This application claims the benefit of U.S. Provisional Application No. 60/537,452, filed Jan. 16, 2004, which application is incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to methods for degrading lignocellulosic materials.

2. Description of the Related Art

The majority of carbohydrates in plants are in the form of lignocellulose, which is composed of mainly cellulose, hemicellulose, pectin, and lignin. Lignocellulose is found, for example, in the stems, leaves, hulls, husks, and cobs of plants. Hydrolysis of these polymers releases a mixture of neutral sugars including glucose, xylose, mannose, galactose, and arabinose.

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, glucohydrolases and beta-glucosidases. Endoglucanases digest the cellulose polymer at random locations, opening it to attack by cellobiohydrolases. Glucohydrolases liberate molecules of glucose from the ends of the cellulose polymer. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

Hemicelluloses are short branched chain heteropolysaccharides that are composed of various hexoses (glucose, mannose and galactose), pentoses (D-xylose and L-arabinose), uronic acids, acetic acid, and other minor sugars. Similar to cellulose degradation, hemicellulose hydrolysis requires coordinated action of many enzymes, which can be placed into three general categories, the endo-acting enzymes that attack internal bonds within the polysaccharide chain, the exo-acting enzymes that act processively from either the reducing or nonreducing end of the polysaccharide chain, and the accessory enzymes (acetylesterases and esterases that hydrolyze lignin glycoside bonds).

Lignocellulosic materials, such as wood, herbaceous material, agricultural residues, corn fiber, waste paper, pulp and paper mill residues can be used to produce ethanol. No known natural organism can rapidly and efficiently metabolize all carbohydrate polymers in lignocellulosic biomass into ethanol. The conversion of lignocellulosic feedstocks into ethanol has the advantages of the ready availability of large amounts of feedstock, the desirability of avoiding burning or land filling the materials, and the cleanliness of the ethanol fuel. Once the cellulose is converted to glucose, the glucose is easily fermented by yeast into ethanol.

However, an obstacle to commercialization is the cost of enzymes to convert the lignocellulosic material to glucose and other fermentable sugars. There is a need in the art to improve the ability of cellulolytic enzymes to degrade lignocellulosic materials to useful organic products or to intermediates to useful end-products.

It is an object of the present invention to improve the ability of cellulolytic enzymes to degrade lignocellulosic materials.

SUMMARY OF THE INVENTION

The present invention relates to methods for degrading a lignocellulosic material, comprising: treating the lignocellulosic material with an effective amount of one or more cellulolytic enzymes in the presence of at least one surfactant selected from the group consisting of a secondary alcohol ethoxylate, fatty alcohol ethoxylate, nonylphenol ethoxylate, tridecyl ethoxylate, and polyoxyethylene ether, wherein the presence of the surfactant increases the degradation of lignocellulosic material compared to the absence of the surfactant.

The present invention also relates to methods for producing an organic substance, comprising:

(a) saccharifying a lignocellulosic material with an effective amount of one or more cellulolytic enzymes in the presence of at least one surfactant selected from the group consisting of a secondary alcohol ethoxylate, fatty alcohol ethoxylate, nonylphenol ethoxylate, tridecyl ethoxylate, and polyoxyethylene ether, wherein the presence of the surfactant increases the degradation of lignocellulosic material compared to the absence of the surfactant;

(b) fermenting the saccharified lignocellulosic material of step (a) with one or more fermenting microorganisms; and (c) recovering the organic substance from the fermentation.

In a preferred embodiment, the organic substance is alcohol.

BRIEF DESCRIPTION OF THE FIGURES

FIG. 7 shows the DNA sequence (SEQ ID NO: 26) and deduced amino acid sequence (SEQ ID NO: 27) of the secretion signal sequence of an *Aspergillus oryzae* beta-glucosidase.
FIG. 8 shows the DNA sequence (SEQ ID NO: 30) and deduced amino acid sequence (SEQ ID NO: 31) of the secretion signal sequence of a *Humicola insolens* endoglucanase V.
FIGS. 10A and 10B shows the genomic DNA sequence and the deduced amino acid sequence of an *Aspergillus fumigatus* beta-glucosidase (SEQ ID NOS: 36 and 37, respectively). The predicted signal peptide is underlined and predicted introns are italicized.

DETAILED DESCRIPTION OF THE INVENTION

Figure 1:
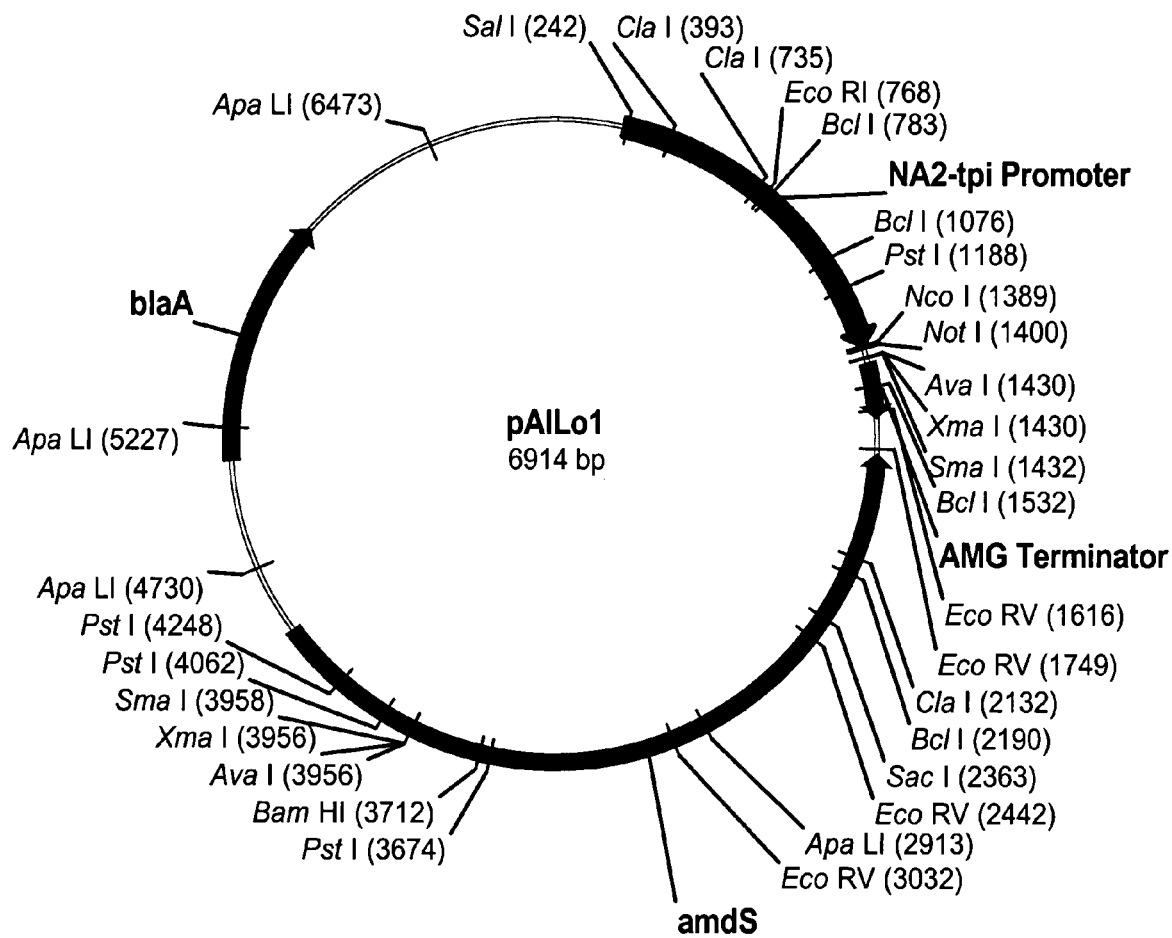
FIG. 1 shows a restriction map of pAlLo1.

The present invention relates to methods for degrading a lignocellulosic material, comprising: treating the lignocellulosic material with an effective amount of one or more cellulolytic enzymes in the presence of at least one surfactant selected from the group consisting of a secondary alcohol ethoxylate, fatty alcohol ethoxylate, nonylphenol ethoxylate, tridecyl ethoxylate, and polyoxyethylene ether, wherein the presence of the surfactant increases the degradation of lignocellulosic material compared to the absence of the surfactant.

Lignocellulosic Material

In the methods of the present invention, the lignocellulosic material can be any material containing lignocellulose. Lignocellulose is generally found, for example, in the stems, leaves, hulls, husks, and cobs of plants or leaves, branches, and wood of trees. The lignocellulosic material can also be, but is not limited to, herbaceous material, agricultural residues, forestry residues, municipal solid wastes, waste paper, and pulp and paper mill residues.

In a preferred embodiment, the lignocellulosic material is corn stover. In another preferred embodiment, the lignocellulosic material is corn fiber. In another preferred embodiment, the lignocellulosic material is rice straw. In another preferred embodiment, the lignocellulosic material is paper and pulp processing waste. In another preferred embodiment, the lignocellulosic material is woody or herbaceous plants.

The lignocellulosic material may be used as is or may be subjected to a pretreatment using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., Singh, A., 1993, Physicochemical and biological treatments for enzymatic/microbial conversion of lignocellulosic biomass, *Adv. Appl. Microbiol.*, 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech*, 18: 312-331; and Vallander, L., and Eriksson, K.-E. L., 1990, Production of ethanol from lignocellulosic materials: State of the art, *Adv. Biochem. Eng./Biotechnol.*, 42: 63-95).

Surfactants

In the methods of the present invention, the surfactant may be any surfactant selected from the group consisting of a secondary alcohol ethoxylate, fatty alcohol ethoxylate, nonylphenol ethoxylate, tridecyl ethoxylate, and polyoxyethylene ether. The surfactant is added exogenously.

In a preferred embodiment, the surfactant is a secondary alcohol ethoxylate.

In another preferred embodiment, the surfactant is a fatty alcohol ethoxylate.

In another preferred embodiment, the surfactant is a nonylphenol ethoxylate.

In another preferred embodiment, the surfactant is a tridecyl ethoxylate.

In another preferred embodiment, the surfactant is a polyoxyethylene ether.

A secondary alcohol ethoxylate surfactant has the formula $C_{11-15}H_{23-31}O(CH_2CH_2O)_xH$, wherein x is the degree of ethoxylation. The degree of ethoxylation can be from at least 3 to at least 50. In a preferred embodiment, the secondary alcohol ethoxylate is alkyloxypolyethyleneoxyethanol 50 (x=5). In another preferred embodiment, the secondary alcohol ethoxylate is alkyloxypolyethyleneoxyethanol 90 (x=9). In another preferred embodiment, the secondary alcohol ethoxylate is alkyloxypolyethyleneoxyethanol 120 (x=12). In another preferred embodiment, the secondary alcohol ethoxylate is alkyloxypolyethyleneoxyethanol 200 (x=20). Examples of commercially available secondary alcohol ethoxylate surfactants include, but are not limited to, SOFTANOL™ 50, SOFTANOL™ 90, SOFTANOL™ 120, and SOFTANOL™ 200, obtainable from INEOS Oxide, Zwijndrecht, Belgium.

A fatty alcohol ethoxylate has the formula $C_{16-18}H_{33-37}O(CH_2CH_2O)_xH$, wherein x is the degree of ethoxylation. The degree of ethoxylation can be from at least 11 to at least 80. Examples of commercially available fatty alcohol ethoxylate surfactants include, but are not limited to, Lutensol AT50 (x=50) and Lutensol AT80 (x=80), obtainable from BASF Corp., Mount Olive, N.J., USA.

A nonylphenol ethoxylate has the formula $C_9H_{19}C_6H_4(CH_2CH_2O)_xOH$, wherein x is the degree of ethoxylation. The degree of ethoxylation can be from at least 4 to at least 70. Examples of commercially available nonylphenol ethoxylate surfactants include, but are not limited to, Tergitol NP-9 (x=9.3), obtainable from the Dow Chemical Company, Midland, Mich., USA.

A tridecyl ethoxylate has the formula $C_{13-15}H_{27-31}O(CH_2CH_2O)_xH$, wherein x is the degree of ethoxylation. The degree of ethoxylation can be from at least 2 to at least 50. Examples of commercially available tridecyl ethoxylate surfactants include, but are not limited to, Novell II TDA-6.6 (x=6.6) and Novell II TDA-8.5 (x=8.5), obtainable from Sasol, Houston, Tex.

A polyoxyethylene ether has the formula $C_{12-18}H_{25-37}(CH_2CH_2O)_xOCH_2CHO$, wherein x is the degree of ethoxylation. The degree of ethoxylation can be from at least 10 to at least 23. Examples of commercially available polyoxyethylene ether surfactants include, but are not limited to, Brij 35 (x=23), Brij 56 (x=10), Brij 97 (x=10), and Brij 98 (x=20), obtainable from Sigma Chemical Co., St. Loius, Mo.

A summary of the above-noted surfactants is shown in Table 1.

TABLE 1

| Surfactant | Chemistry | Supplier | MW | CP, °C. | HLB | EO Mole # | Appearance |
|---|---|---|---|---|---|---|---|
| Softanol 50 | Secondary AE $C_{11-15}H_{23-31}O(EO)_5H$ | Honeywell & Stein/INEOS Oxide | 420 | <0 | 10.5 | 5 | Liquid |
| Sofftanol 90 | Secondary AE $C_{11-15}H_{23-31}O(EO)_9H$ | Honeywell & Stein/INEOS Oxide | 600 | 56 | 13.3 | 9 | Liquid |
| Softanol 120 | Secondary AE $C_{11-15}H_{23-31}O(EO)_{12}H$ | Honeywell & Stein/INEOS Oxide | 730 | 83 | 14.5 | 12 | Wax (Liquid @ 30° C.) |
| Softanol 200 | Secondary AE $C_{11-15}H_{23-31}O(EO)_{20}H$ | Honeywell & Stein/INEOS Oxide | 1080 | NA | | 20 | Solid |
| Lutensol AT50 | Fatty AE $C_{16-18}H_{33-37}O(EO)_{50}H$ | BASF | | 92 | | 50 | Solid |
| Lutensol AT80 | Fatty AE $C_{16-18}H_{33-37}O(EO)_{80}H$ | BASF | | | | 80 | Solid |
| Tergitol NP-9 | Nonylphenol Ethoxylate $C_9H_{19}C_6H_4(EO)_{9.3}OH$ | Dow Chemical Company | | 53 | 13 | 9.3 | Liquid |
| Novell II TDA-6.6 | Tridecyl AE $C_{13-15}H_{27-31}O(EO)_{6.6}H$ | Sasol North America | | 25 | 11.8 | 6.7 | Liquid |
| Novell II TDA-8.5 | Tridecyl AE $C_{13-15}H_{27-31}O(EO)_{8.5}H$ | Sasol North America | | 54 | 13 | 8.7 | Liquid |
| Brij 35 | Polyoxyethylene 23 Lauryl Ether | ICI Americas/Sigma | | | | | Liquid |
| Brij 56 | Polyoxyethylene 10 Cetyl Ether | ICI Americas/Sigma | | | | | Wax |
| Brij 97 | Polyoxyethylene 10 Oleyl Ether | ICI Americas/Sigma | | | | | Wax |
| Brij 98 | Polyoxyethylene 20 Oleyl Ether | ICI Americas/Sigma | | | | | Wax |

AE—alcohol ethoxylate,
EO—ethylene oxide ($CH_2CH_2O$),
PO—propylene oxide ($CH_2CHCH_3O$),
CP—cloud point,
HLB—hydrophilic/lipophilic balance Cellulolytic Enzymes In the methods of the present invention, the cellulolytic enzyme may any enzyme involved in the degradation of lignocellulose to glucose, xylose, mannose, galactose, and arabinose. The cellulolytic enzyme may be a multicomponent enzyme preparation, e.g., cellulase, a monocomponent enzyme preparation, e.g., endoglucanase, cellobiohydrolase, glucohydrolase, beta-glucosidase, or a combination of multicomponent and monocomponent enzymes. The cellulolytic enzymes may have activity, i.e., hydrolyze cellulose, either in the acid, neutral, or alkaline pH-range.

The cellulolytic enzyme may be of fungal or bacterial origin, which may be obtainable or isolated and purified from microorganisms which are known to be capable of producing cellulolytic enzymes, e.g., species of *Humicola, Coprinus, Thielavia, Fusarium, Myceliophthora, Acremonium, Cephalosporium, Scytalidium, Penicillium* or *Aspergillus* (see, for example, EP 458162), especially those produced by a strain selected from the species *Humicola insolens* (reclassified as *Scytalidium thermophilum*, see for example, U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Trichoderma* (particularly *Trichoderma viride, Trichoderma reesei,* and *Trichoderma koningii*), alkalophilic *Bacillus* (see, for example, U.S. Pat. No. 3,844,890 and EP 458162), and *Streptomyces* (see, for example, EP 458162).

The cellulolytic enzymes used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of a cellulolytic enzyme. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the cellulase to be expressed or isolated.

The resulting cellulolytic enzymes produced by the methods described above may be recovered from the fermentation medium by conventional procedures including, but not limited to, centrifugation, filtration, spray-drying, evaporation, or precipitation. The recovered enzyme may then be further purified by a variety of chromatographic procedures, e.g., ion exchange chromatography, gel filtration chromatography, affinity chromatography, or the like.

Cellulase hydrolyzes carboxymethyl cellulose (CMC), thereby decreasing the viscosity of the incubation mixture. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of carboxymethyl cellulose (CMC). The assay is carried out at 40° C. in 0.1 M phosphate pH 9.0 buffer for 30 minutes with CMC as substrate (33.3 g/L carboxymethyl cellulose Hercules 7 LFD) and an enzyme concentration of approximately 3.3-4.2 CEVU/ml. The CEVU activity is calculated relative to a declared enzyme standard, such as Celluzyme™ Standard 17-1194 (obtained from Novozymes A/S, Bagsvaerd, Denmark).

Examples of cellulases suitable for use in the present invention include, for example, CELLUCLAST™ (available from Novozymes A/S) and NOVOZYM™ 188 (available from Novozymes A/S). Other commercially available preparations comprising cellulase which may be used include CELLUZYME™, CEREFLO™ and ULTRA-FLO™ (Novozymes A/S), LAMINEX™ and SPEZYME™ CP (Genencor Int.), and ROHAMENT™ 7069 W (Röhm GmbH). The cellulase enzymes are added in amounts effective from about 0.001% to about 5.0% wt. of solids, more preferably from about 0.025% to about 4.0% wt. of solids, and most preferably from about 0.005% to about 2.0% wt. of solids.

As mentioned above, the cellulolytic enzymes used in the methods of the present invention may be monocomponent preparations, i.e., a component essentially free of other cellulase components. The single component may be a recombinant component, i.e., produced by cloning of a DNA sequence encoding the single component and subsequent cell transformed with the DNA sequence and expressed in a host (see, for example, WO 91/17243 and WO 91/17244). Other examples of monocomponent cellulolytic enzymes include, but are not limited to, those disclosed in JP-07203960-A and WO-9206209. The host is preferably a heterologous host (enzyme is foreign to host), but the host may under certain conditions also be a homologous host (enzyme is native to host). Monocomponent cellulolytic enzymes may also be prepared by purifying such an enzyme from a fermentation medium.

Examples of monocomponent cellulolytic enzymes useful in practicing the methods of the present invention include, but are not limited to, endoglucanase, cellobiohydrolase, glucohydrolase, and beta-glucosidase.

The term "endoglucanase" is defined herein as an endo-1,4-(1,3;1,4)-beta-D-glucan 4-glucanohydrolase (E.C. No. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268.

The exo-1,4-beta-D-glucanases include both cellobiohydrolases and glucohydrolases.

The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, *Anal. Biochem.* 47: 273-279 and by van Tilbeurgh et al., 1982, *FEBS Letters,* 149: 152-156; van Tilbeurgh and Claeyssens, 1985, *FEBS Letters,* 187: 283-288. In the present invention, the Lever et al. method was employed to assess hydrolysis of cellulose in corn stover, while the method of van Tilbeurgh et al. was used to determine the cellobiohydrolase activity on a fluorescent disaccharide derivative.

The term "glucohydrolase" is defined herein as a 1,4-beta-D-glucan glucohydrolase (E.C. 3.2.1.74), which catalyzes the hydrolysis of 1,4-linkages (O-glycosyl bonds) in 1,4-beta-D-glucans so as to remove successive glucose units. For purposes of the present invention, exoglucanase activity is determined according to the procedure described by Himmel et al., 1986, *J. Biol. Chem.* 261: 12948-12955.

The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 µmole of p-nitrophenol produced per minute at 50° C., pH 5 from 4 mM p-nitrophenyl-beta-D-glucopyranoside as substrate in 100 mM sodium citrate, 0.01% Tween-20.

Processing of Lignocellulosic Materials

The methods of the present invention may be used to process a lignocellulosic material to many useful organic products, chemicals and fuels. In addition to ethanol, some commodity and specialty chemicals that can be produced from lignocellulose include xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., 1999, Biocommodity engineering, *Biotechnol. Prog.*, 15: 777-793; Philippidis, G. P., 1996, Cellulose bioconversion technology, in *Handbook on Bioethanol: Production and Utilization*, Wyman, C. E., ed., Taylor & Francis, Washington, D.C., 179-212; and Ryu, D. D. Y., and Mandels, M., 1980, Cellulases: biosynthesis and applications, *Enz. Microb. Technol.*, 2: 91-102). Potential coproduction benefits extend beyond the synthesis of multiple organic products from fermentable carbohydrate. Lignin-rich residues remaining after biological processing can be converted to lignin-derived chemicals, or used for power production.

Conventional methods used to process the lignocellulosic material in accordance with the methods of the present invention are well understood to those skilled in the art. The methods of the present invention may be implemented using any conventional biomass processing apparatus configured to operate in accordance with the invention.

Such an apparatus may include a batch-stirred reactor, a continuous flow stirred reactor with ultrafiltration, a continuous plug-flow column reactor (Gusakov, A. V., and Sinitsyn, A. P., 1985, Kinetics of the enzymatic hydrolysis of cellulose: 1. A mathematical model for a batch reactor process, *Enz. Microb. Technol.*, 7: 346-352), an attrition reactor (Ryu, S. K., and Lee, J. M., 1983, Bioconversion of waste cellulose by using an attrition bioreactor, *Biotechnol. Bioeng.*, 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.*, 56: 141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to glucose and then ferment glucose to ethanol. In SSF, the enzymatic hydrolysis of cellulose and the fermentation of glucose to ethanol is combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF includes the coferementation of multiple sugars (Sheehan, J., and Himmel, M., 1999, Enzymes, energy and the environment: A strategic perspective on the U.S. Department of Energy's research and development activities for bioethanol, *Biotechnol. Prog.*, 15: 817-827). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbiol. Mol. Biol. Reviews*, 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

Methods for Producing Organic Substances

The present invention also relates to methods for producing an organic substance, comprising: (a) saccharifying a lignocellulosic material with an effective amount of one or more cellulolytic enzymes in the presence of at least one surfactant selected from the group consisting of a secondary alcohol ethoxylate, fatty alcohol ethoxylate, nonylphenol ethoxylate, tridecyl ethoxylate, and polyoxyethylene ether, wherein the presence of the surfactant increases the degradation of lignocellulosic material compared to the absence of the surfactant; (b) fermenting the saccharified lignocellulosic material of step (a) with one or more fermentating microoganisms; and (c) recovering the organic substance from the fermentation.

The organic substance can be any substance derived from the fermentation. In a preferred embodiment, the organic substance is an alcohol. It will be understood that the term "alcohol" encompasses an organic substance that contains one or more hydroxyl moieties. In a more preferred embodiment, the alcohol is arabinitol. In another more preferred embodiment, the alcohol is butanol. In another more preferred embodiment, the alcohol is ethanol. In another more preferred embodiment, the alcohol is glycerol. In another more preferred embodiment, the alcohol is methanol. In another more preferred embodiment, the alcohol is 1,3-propanediol. In another more preferred embodiment, the alcohol is sorbitol. In another more preferred embodiment, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry*, 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred embodiment, the organic substance is an organic acid. In another more preferred embodiment, the organic acid is acetic acid. In another more preferred embodiment, the organic acid is acetonic acid. In another more preferred embodiment, the organic acid is adipic acid. In another more preferred embodiment, the organic acid is ascorbic acid. In another more preferred embodiment, the organic acid is citric acid. In another more preferred embodiment, the organic acid is 2,5-diketo-D-gluconic acid. In another more preferred embodiment, the organic acid is formic acid. In another more preferred embodiment, the organic acid is fumaric acid. In another more preferred embodiment, the organic acid is glucaric acid. In another more preferred embodiment, the organic acid is gluconic acid. In another more preferred embodiment, the organic acid is glucuronic acid. In another more preferred embodiment, the organic acid is glutaric acid. In another preferred embodiment, the organic acid is 3-hydroxypropionic acid. In another more preferred embodiment, the organic acid is itaconic acid. In another more preferred embodiment, the organic acid is lactic acid. In another more preferred embodiment, the organic acid is malic acid. In another more preferred embodiment, the organic acid is malonic acid. In another more preferred embodiment, the organic acid is oxalic acid. In another more preferred embodiment, the organic acid is propionic acid. In another more preferred embodiment, the organic acid is succinic acid. In another more preferred embodiment, the organic acid is xylonic acid. See, for example, Chen, R., and Lee, Y. Y., 1997, Membrane-mediated extractive fermentation for lactic acid production from cellulosic biomass, *Appl. Biochem. Biotechnol.*, 63-65: 435-448.

In another preferred embodiment, the organic substance is a ketone. It will be understood that the term "ketone" encompasses an organic substance that contains one or more ketone moieties. In another more preferred embodiment, the ketone is acetone. See, for example, Qureshi and Blaschek, 2003, supra.

In another preferred embodiment, the organic substance is an amino acid. In another more preferred embodiment, the organic acid is aspartic acid. In another more preferred embodiment, the amino acid is glutamic acid. In another more preferred embodiment, the amino acid is glycine. In another more preferred embodiment, the amino acid is lysine. In another more preferred embodiment, the amino acid is serine. In another more preferred embodiment, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering*, 87 (4): 501-515.

In another preferred embodiment, the organic substance is a gas. In another more preferred embodiment, the gas is methane. In another more preferred embodiment, the gas is $H_2$. In another more preferred embodiment, the gas is $CO_2$. In another more preferred embodiment, the gas is CO. See, for example, Kataoka, N., A. Miya, and K. Kiriyama, 1997, Studies on hydrogen production by continuous culture system of hydrogen-producing anaerobic bacteria, *Water Science and Technology* 36(6-7): 41-47; and Gunaseelan V. N. in *Biomass and Bioenergy*, Vol. 13 (1-2), pp. 83-114, 1997, Anaerobic digestion of biomass for methane production: A review.

Production of an organic substance from lignocellulosic material typically requires four major steps. These four steps are pretreatment, enzymatic hydrolysis, fermentation, and recovery. Exemplified below is a process for producing ethanol, but it will be understood that similar processes can be used to produce other organic substances, for example, the substances described above.

Pretreatment. In the pretreatment or pre-hydrolysis step, the lignocellulosic material is heated to break down the lignin and carbohydrate structure, solubilize most of the hemicellulose, and make the cellulose fraction accessible to cellulolytic enzymes. The heating is peformed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Lignocellulosic biomass may also be subject to a hydrothermal steam explosion pre-treatment (See U.S. Patent Application No. 20020164730).

Saccharification. In the enzymatic hydrolysis step, also known as saccharification, enzymes as described herein are added to the pretreated material to convert the cellulose fraction to glucose and/or other sugars. The saccharification is generally performed in stirred-tank reactors or fermentors under controlled pH, temperature, and mixing conditions. A saccharification step may last up to 120 hours. Saccharification may be carried out at temperatures from about 30° C. to about 65° C., in particular around 50° C., and at a pH in the range between about 4 and about 5, especially around pH 4.5. To produce glucose that can be metabolized by yeast, the hydrolysis is typically performed in the presence of a beta-glucosidase.

Fermentation. In the fermentation step, sugars, released from the lignocellulosic material as a result of the pretreatment and enzymatic hydrolysis steps, are fermented to ethanol by a fermenting organism, such as yeast. The fermentation can also be carried out simultaneously with the enzymatic hydrolysis in the same vessel, again under controlled pH, temperature, and mixing conditions. When saccharification and fermentation are performed simultaneously in the same vessel, the process is generally termed simultaneous saccharification and fermentation or SSF.

Any suitable lignocellulosic substrate or raw material may be used in a fermentation process of the present invention. The substrate is generally selected based on the desired fermentation product, i.e., the organic substance to be obtained from the fermentation, and the process employed, as is well known in the art. Examples of substrates suitable for use in the methods of present invention, include lignocellulose-containing materials, such as wood or plant residues or low molecular sugars $DP_{1-3}$ obtained from processed lignocellulosic material that can be metabolized by the fermenting microorganism, and which may be supplied by direct addition to the fermentation medium.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms according to the invention are able to ferment, i.e., convert, sugars, such as glucose, xylose, arabinose, mannose, galactose, or oligosaccharides directly or indirectly into the desired fermentation product. Examples of fermenting microorganisms include fungal organisms, such as yeast. Preferred yeast includes strains of the *Sacchromyces* spp., and in particular, *Sacchromyces cerevisiae*. Commercially available yeast include, e.g., Red Star®/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

In a preferred embodiment, the yeast is a *Saccharomyces* spp. In a more preferred embodiment, the yeast is *Saccharomyces cerevisiae*. In another more preferred embodiment, the yeast is *Saccharomyces distaticus*. In another more preferred embodiment, the yeast is *Saccharomyces uvarum*. In another preferred embodiment, the yeast is a *Kluyveromyces*. In another more preferred embodiment, the yeast is *Kluyveromyces marxianus*. In another more preferred embodiment, the yeast is *Kluyveromyces fragilis*. In another preferred embodiment, the yeast is a *Candida*. In another more preferred embodiment, the yeast is *Candida pseudotropicalis*. In another more preferred embodiment, the yeast is *Candida brassicae*. In another preferred embodiment, the yeast is a *Clavispora*. In another more preferred embodiment, the yeast is *Clavispora lusitaniae*. In another more preferred embodiment, the yeast is *Clavispora opuntiae*. In another preferred embodiment, the yeast is a *Pachysolen*. In another more preferred embodiment, the yeast is *Pachysolen tannophilus*. In another preferred embodiment, the yeast is a *Bretannomyces*. In another more preferred embodiment, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment glucose to ethanol include, for example, *Zymomonas mobilis* and *Clostridium thermocellum* (Philippidis, 1996, supra).

It is well known in the art that the various of the organisms described above can also be used to produce other organic substances, as described herein.

The cloning of heterologous genes in *Saccharomyces cerevisiae* (Chen, Z., Ho, N. W. Y., 1993, Cloning and improving the expression of *Pichia stipitis* xylose reductase gene in *Saccharomyces cerevisiae*, *Appl. Biochem. Biotechnol.* 39-40: 135-147; Ho, N. W. Y., Chen, Z, Brainard, A. P., 1998, Genetically engineered *Saccharomyces* yeast capable of effectively cofermenting glucose and xylose, *Appl. Environ. Microbiol.*, 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli*, *Biotech. Bioeng.* 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.* 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis*, *Science* 267: 240-243; Deanda, K., Zhang, M., Eddy, C., and Picataggio, S., 1996, Development of an arabinose-fermenting *Zymomonas mobilis* strain by metabolic pathway engineering, *Appl. Environ. Microbiol.* 62: 4465-4470) has led to the construction of organisms capable of converting hexoses and pentoses to ethanol (cofermentation).

Yeast or another microorganism typically is added to the degraded lignocellulose or hydrolysate and the fermentation is ongoing for about 24 to about 96 hours, such as about 35 to about 60 hours. The temperature is typically between about 26° C. to about 40° C., in particular at about 32° C., and at about pH 3 to about pH 6, in particular around pH 4-5.

In preferred embodiments, yeast or another microorganism is applied to the degraded lignocellulose or hydrolysate and the fermentation is ongoing for about 24 to about 96 hours, such as typically 35-60 hours. In preferred embodiments, the temperature is generally between about 26 to about 40° C., in particular about 32° C., and the pH is generally from about pH 3 to about pH 6, preferably around pH 4-5. Yeast or another microorganism is preferably applied in amounts of approximately $10^5$ to $10^{12}$, preferably from approximately $10^7$ to $10^{10}$, especially approximately $5 \times 10^7$ viable count per ml of fermentation broth. During an ethanol producing phase the yeast cell count should preferably be in the range from approximately $10^7$ to $10^{10}$, especially around approximately $2 \times 10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the mash is distilled to extract the ethanol. The ethanol obtained according to the process of the invention may be used as, e.g., fuel ethanol; drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisiae* by a vitamin feeding strategy during fed-batch process," Springer-Verlag (2002), which is hereby incorporated by reference. Examples of minerals include minerals and mineral salts that can supply nutrients comprising P, K, Mg, S, Ca, Fe, Zn, Mn, and Cu.

Recovery. The alcohol is separated from the fermented lignocellulosic material and purified by conventional methods of distillation. Ethanol with a purity of up to about 96 vol. % ethanol can be obtained, which can be used as, for example, fuel ethanol, drinking ethanol, i.e., potable neutral spirits, or industrial ethanol.

For other organic substances, any method known in the art can be used including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

Additional Enzymes

In the methods of the present invention, the cellulolytic enzyme(s) may be supplemented by one or more additional enzyme activities to improve the degradation of the lignocellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

The enzymes referenced herein may be derived or obtained from any suitable origin, including, bacterial, fungal, yeast or mammalian origin. The term "obtained" means herein that the enzyme may have been isolated from an organism which naturally produces the enzyme as a native enzyme. The term "obtained" also means herein that the enzyme may have been produced recombinantly in a host organism, wherein the recombinantly produced enzyme is either native or foreign to the host organism or has a modified amino acid sequence, e.g., having one or more amino acids which are deleted, inserted and/or substituted, i.e., a recombinantly produced enzyme which is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be "substantially pure," that is, free from other components from the organism in which it is produced, that is, for example, a host organism for recombinantly produced enzymes. In preferred embodiment, the enzymes are at least 75% (w/w), preferably at least 80%, more preferably at least 85%, more preferably at least 90%, more preferably at least 95%, more preferably at least 96%, more preferably at least 97%, even more preferably at least 98%, or most preferably at least 99% pure. In another preferred embodiment, the enzyme is 100% pure.

The enzymes used in the present invention may be in any form suitable for use in the processes described herein, such as, for example, in the form of a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

Hemicellulases

Enzymatic hydrolysis of hemicelluloses can be performed by a wide variety of fungi and bacteria. Similar to cellulose degradation, hemicellulose hydrolysis requires coordinated action of many enzymes. Hemicellulases can be placed into three general categories: the endo-acting enzymes that attack internal bonds within the polysaccharide chain, the exo-acting enzymes that act processively from either the reducing or nonreducing end of polysaccharide chain, and the accessory enzymes, acetylesterases and esterases that hydrolyze lignin glycoside bonds, such as coumaric acid esterase and ferulic acid esterase (Wong, K. K. Y., Tan, L. U. L., and Saddler, J. N., 1988, Multiplicity of β-1,4-xylanase in microorganisms: Functions and applications, *Microbiol. Rev.* 52: 305-317; Tenkanen, M., and Poutanen, K., 1992, Significance of esterases in the degradation of xylans, in *Xylans and Xylanases*, Visser, J., Beldman, G., Kuster-van Someren, M. A., and Voragen, A. G. J., eds., Elsevier, New York, N.Y., 203-212; Coughlan, M. P., and Hazlewood, G. P., 1993, Hemicellulose and hemicellulases, Portland, London, UK; Brigham, J. S., Adney, W. S., and Himmel, M. E., 1996, Hemicellulases: Diversity and applications, in *Handbook on Bioethanol: Production and Utilization*, Wyman, C. E., ed., Taylor & Francis, Washington, D.C., 119-141).

Hemicellulases include xylanases, arabinofuranosidases, acetyl xylan esterase, glucuronidases, endo-galactanase, mannanases, endo or exo arabinases, exo-galactanses, and mixtures thereof. Examples of endo-acting hemicellulases and ancillary enzymes include endoarabinanase, endoarabinogalactanase, endoglucanase, endomannanase, endoxylanase, and feraxan endoxylanase. Examples of exo-acting hemicellulases and ancillary enzymes include α-L-arabinosidase, β-L-arabinosidase, α-1,2-L-fucosidase, α-D-galactosidase, β-D-galactosidase, β-D-glucosidase, β-D-glucuronidase, β-D-mannosidase, β-D-xylosidase, exoglucosidase, exocellobiohydrolase, exomannobiohydrolase, exomannanase, exoxylanase, xylan α-glucuronidase, and coniferin β-glucosidase. Examples of esterases include acetyl esterases (acetylgalactan esterase, acetylmannan esterase, and acetylxylan esterase) and aryl esterases (coumaric acid esterase and ferulic acid esterase).

Preferably, the hemicellulase is an exo-acting hemicellulase, and more preferably, an exo-acting hemicellulase which has the ability to hydrolyze hemicellulose under acidic conditions of below pH 7. An example of a hemicellulase suitable for use in the present invention includes VISCOZYME™ (available from Novozymes A/S, Denmark). The hemicellulase is added in an effective amount from about 0.001% to about 5.0% wt. of solids, more preferably from about 0.025% to about 4.0% wt. of solids, and most preferably from about 0.005% to about 2.0% wt. of solids.

A xylanase (E.C. 3.2.1.8) may be obtained from any suitable source, including fungal and bacterial organisms, such as *Aspergillus, Disporotrichum, Penicillium, Neurospora, Fusarium, Trichoderma, Humicola, Thermomyces*, and *Bacillus*. Preferred commercially available preparations comprising xylanase include SHEARZYME®, BIOFEED WHEAT®, BIO-FEED Plus® L, CELLUCLAST®, ULTRAFLO®, VISCOZYME®, PENTOPAN MONO®

BG, and PULPZYME® HC (Novozymes A/S); and LAMINEX® and SPEZYME® CP (Genencor Int.).

Esterases

Esterases that can be used for bioconversion of lignocellulose include acetyl esterases such as acetylgalactan esterase, acetylmannan esterase, and acetylxylan esterase, and esterases that hydrolyze lignin glycoside bonds, such as coumaric acid esterase and ferulic acid esterase.

As used herein, an "esterase" also known as a carboxylic ester hydrolyase, refers to enzymes acting on ester bonds, and includes enzymes classified in EC 3.1.1 Carboxylic Ester Hydrolases according to Enzyme Nomenclature (Enzyme Nomenclature 1992, Academic Press, San Diego, Calif., with Supplement 1 (1993), Supplement 2 (1994), Supplement 3 (1995), Supplement 4 (1997) and Supplement 5, in Eur. J. Biochem. 223: 1-5, 1994; Eur. J. Biochem. 232: 1-6,1995; Eur. J. Biochem. 237: 1-5, 1996; Eur. J. Biochem. 250: 1-6, 1997, and Eur. J. Biochem. 264: 610-650, 1999; respectively). Non-limiting examples of esterases include arylesterase, triacylglycerol lipase, acetylesterase, acetylcholinesterase, cholinesterase, tropinesterase, pectinesterase, sterol esterase, chlorophyllase, L-arabinonolactonase, gluconolactonase, uronolactonase, tannase, retinyl-palmitate esterase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinonolactonase, 6-phosphogluconolactonase, phospholipase A1, 6-acetylglucose deacetylase, lipoprotein lipase, dihydrocoumarin lipase, limonin-D-ring-lactonase, steroid-lactonase, triacetate-lactonase, actinomycin lactonase, orsellinate-depside hydrolase, cephalosporin-C deacetylase, chlorogenate hydrolase, alpha-amino-acid esterase, 4-methyloxaloacetate esterase, carboxymethylenebutenolidase, deoxylimonate A-ring-lactonase, 2-acetyl-1-alkylglycerophosphocholine esterase, fusarinine-C ornithinesterase, sinapine esterase, wax-ester hydrolase, phorbol-diester hydrolase, phosphatidylinositol deacylase, sialate O-acetylesterase, acetoxybutynyl-bithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethylhexyl)phthalate esterase, protein-glutamate methylesterase, 11-cis-retinyl-palmitate hydrolase, all-trans-retinyl-palmitate hydrolase, L-rhamnono-1,4-lactonase, 5-(3,4-diacetoxybut-1-ynyl)-2, 2'-bithiophene deacetylase, fatty-acyl-ethyl-ester synthase, xylono-1,4-lactonase, N-acetylglucosaminylphosphatidylinositol deacetylase, cetraxate benzylesterase, acetylalkylglycerol acetylhydrolase, and acetylxylan esterase.

Preferred esterases for use in the present invention are lipolytic enzymes, such as, lipases (classified as EC 3.1.1.3, EC 3.1.1.23, and/or EC 3.1.1.26) and phospholipases (classified as EC 3.1.1.4 and/or EC 3.1.1.32, including lysophospholipases classified as EC 3.1.1.5). Other preferred esterases are cutinases (classified as EC 3.1.1.74).

The esterase may be added in an amount effective to obtain the desired benefit to improve the performance of the fermenting microorganism, for example, to change the lipid composition/concentration inside and/or outside of the fermenting microorganism or in the cell membrane of the fermenting microorganism, to result in an improvement in the movement of solutes into and/or out of the fermenting microorganisms during fermentation and/or to provide more metabolizable energy sources (such as, for example, by converting components, such as, oil from the corn substrate, to components useful the fermenting microorganism, e.g., unsaturated fatty acids and glycerol), to increase ethanol yield. Examples of effective amounts of esterase are from about 0.01 to about 400 LU/g DS (Dry Solids). Preferably, the esterase is used in an amount of about 0.1 to about 100 LU/g DS, more preferably about 0.5 to about 50 LU/g DS, and even more preferably about 1 to about 20 LU/g DS. Further optimization of the amount of esterase can hereafter be obtained using standard procedures known in the art.

One Lipase Unit (LU) is the amount of enzyme which liberates 1.0 µmol of titratable fatty acid per minute with tributyrin as substrate and gum arabic as an emulsifier at 30° C., pH 7.0 (phosphate buffer).

In a preferred embodiment, the esterase is a lipolytic enzyme, more preferably, a lipase. As used herein, a "lipolytic enzyme" refers to lipases and phospholipases (including lyso-phospholipases). The lipolytic enzyme is preferably of microbial origin, in particular of bacterial, fungal or yeast origin. The lipolytic enzyme used may be derived from any source, including, for example, a strain of *Absidia*, in particular *Absidia blakesleena* and *Absidia corymbifera*, a strain of *Achromobacter*, in particular *Achromobacter iophagus*, a strain of *Aeromonas*, a strain of *Alternaria*, in particular *Alternaria brassiciola*, a strain of *Aspergillus*, in particular *Aspergillus niger*, *Aspergillus oryzae*, *Asoergillus fumigatus*, and *Aspergillus flavus*, a strain of *Achromobacter*, in particular *Achromobacter iophagus*, a strain of *Aureobasidium*, in particular *Aureobasidium pullulans*, a strain of *Bacillus*, in particular *Bacillus pumilus*, *Bacillus stearothermophilus*, and *Bacillus subtilis*, a strain of *Beauveria*, a strain of *Brochothrix*, in particular *Brochothrix thermosohata*, a strain of *Candida*, in particular *Candida cylindracea* (*Candida rugosa*), *Candida paralipolytica*, and *Candida antarctica*, a strain of *Chromobacter*, in particular *Chromobacter viscosum*, a strain of *Coprinus*, in particular *Coprinus cinerius*, a strain of *Fusarium*, in particular *Fusarium graminearum*, *Fusarium oxysporum*, *Fusarium solani*, *Fusarium solani pisi*, *Fusarium roseum culmorum*, and *Fusarium venenatum*, a strain of *Geotricum*, in particular *Geotricum penicillatum*, a strain of *Hansenula*, in particular *Hansenula anomala*, a strain of *Humicola*, in particular *Humicola brevispora*, *Humicola brevis var. thermoidea*, and *Humicola insolens*, a strain of *Hyphozyma*, a strain of *Lactobacillus*, in particular *Lactobacillus curvatus*, a strain of *Metarhizium*, a strain of *Mucor*, a strain of *Paecilomyces*, a strain of *Penicillium*, in particular *Penicillium cyclopium*, *Penicillium crustosum* and *Penicillium expansum*, a strain of *Pseudomonas* in particular *Pseudomonas aeruginosa*, *Pseudomonas alcaligenes*, *Pseudomonas cepacia* (syn. *Burkholderia cepacia*), *Pseudomonas fluorescens*, *Pseudomonas fragi*, *Pseudomonas maltophilia*, *Pseudomonas mendocina*, *Pseudomonas mephitica lipolytica*, *Pseudomonas alcaligenes*, *Pseudomonas plantari*, *Pseudomonas pseudoalcaligenes*, *Pseudomonas putida*, *Pseudomonas stutzeri*, and *Pseudomonas wisconsinensis*, a strain of *Rhizooctonia*, in particular *Rhizooctonia solani*, a strain of *Rhizomucor*, in particular *Rhizomucor miehei*, a strain of *Rhizopus*, in particular *Rhizopus japonicus*, *Rhizopus microsporus*, and *Rhizopus nodosus*, a strain of *Rhodosporidium*, in particular *Rhodosporidium toruloides*, a strain of *Rhodotorula*, in particular *Rhodotorula glutinis*, a strain of *Sporobolomyces*, in particular *Sporobolomyces shibatanus*, a strain of *Thermomyces*, in particular *Thermomyces lanuginosus* (formerly *Humicola lanuginosa*), a strain of *Thiarosporella*, in particular *Thiarosporella phaseolina*, a strain of *Trichoderma*, in particular, *Trichoderma harzianum* and *Trichoderma reesei*, and/or a strain of *Verticillium*.

In a preferred embodiment, the lipolytic enzyme is derived from a strain of *Aspergillus*, *Achromobacter*, *Bacil-*

*lus, Candida, Chromobacter, Fusarium, Humicola, Hyphozyma, Pseudomonas, Rhizomucor, Rhizopus*, or *Thermomyces*.

In more preferred embodiments, the lipolytic enzyme is a lipase. Lipases may be applied herein for their ability to modify the structure and composition of triglyceride oils and fats in the fermentation media (including fermentation yeast), for example, resulting from a corn substrate. Lipases catalyze different types of triglyceride conversions, such as hydrolysis, esterification, and transesterification. Suitable lipases include acidic, neutral, and basic lipases, as are well-known in the art, although acidic lipases (such as, e.g., the lipase G AMANO 50, available from Amano) appear to be more effective at lower concentrations of lipase as compared to either neutral or basic lipases. Preferred lipases for use in the present invention include *Candida* antarcitca lipase and *Candida cylindracea* lipase. More preferred lipases are purified lipases such as *Candida antarcitca* lipase (lipase A), *Candida antarcitca* lipase (lipase B), *Candida cylindracea* lipase, and *Penicillium camembertii* lipase.

The lipase may be the one disclosed in EP 258,068-A or may be a lipase variant such as a variant disclosed in WO 00/60063 or WO 00/32758, hereby incorporated by reference. Preferred commercial lipases include LECITASE™, LIPOLASE™, and LIPEX™ (available from Novozymes A/S, Denmark) and G AMANO™ 50 (available from Amano).

Lipases are preferably added in amounts from about 1 to about 400 LU/g DS, preferably about 1 to about 10 LU/g DS, and more preferably about 1 to about 5 LU/g DS.

In another preferred embodiment of the present invention, the esterase is a cutinase. Cutinases are enzymes which are able to degrade cutin. The cutinase may be derived from any source. In a preferred embodiment, the cutinase is derived from a strain of *Aspergillus*, in particular *Aspergillus oryzae*, a strain of *Alternaria*, in particular *Alternaria brassiciola*, a strain of *Fusarium*, in particular *Fusarium solani, Fusarium solani pisi, Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina* or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*. In a most preferred embodiment the cutinase is derived from a strain of *Humicola insolens*, in particular the strain *Humicola insolens* DSM 1800. *Humicola insolens* cutinase is described in WO 96/13580, which is hereby incorporated by reference. The cutinase may be a variant such as one of the variants disclosed in WO 00/34450 and WO 01/92502, which are hereby incorporated by reference. Preferred cutinase variants include variants listed in Example 2 of WO 01/92502 which are hereby specifically incorporated by reference. An effective amount of cutinase is from about 0.01 to about 400 LU/g DS, preferably from about 0.1 to about 100 LU/g DS, and more preferably from about 1 to about 50 LU/g DS. Further optimization of the amount of cutinase can hereafter be obtained using standard procedures known in the art.

In another preferred embodiment, the esterase is a phospholipase. As used herein, the term "phospholipase" is an enzyme which has activity towards phospholipids, e.g., hydrolytic activity. Phospholipids, such as lecithin or phosphatidylcholine, consist of glycerol esterified with two fatty acids in an outer (sn-1) and the middle (sn-2) positions and esterified with phosphoric acid in the third position. The phosphoric acid may be esterified to an amino-alcohol. Several types of phospholipase activity can be distinguished, including phospholipases $A_1$ and $A_2$ which hydrolyze one fatty acyl group (in the sn-1 and sn-2 position, respectively) to form lysophospholipid; and lysophospholipase (or phospholipase B) which hydrolyzes the remaining fatty acyl group in lysophospholipid. Phospholipase C and phospholipase D (phosphodiesterases) release diacyl glycerol or phosphatidic acid respectively.

The term "phospholipase" includes enzymes with phospholipase activity, e.g., phospholipase A ($A_1$ or $A_2$), phospholipase B activity, phospholipase C activity, or phospholipase D activity. The term "phospholipase A" as used herein is intended to cover an enzyme with phospholipase $A_1$ and/or phospholipase $A_2$ activity. The phospholipase activity may be provided by enzymes having other activities as well, such as, e.g., a lipase with phospholipase activity. The phospholipase activity may, for example, be from a lipase with phospholipase side activity. In other embodiments, the phospholipase enzyme activity is provided by an enzyme having essentially only phospholipase activity and wherein the phospholipase enzyme activity is not a side activity.

The phospholipase may be of any origin, for example, of animal origin (e.g., mammalian, for example, bovine or porcine pancreas), or snake venom or bee venom. Alternatively, the phospholipase may be of microbial origin, for example, from filamentous fungi, yeast or bacteria, such as *Aspergillus*, e.g., *A. awamori, A. foetidus, A. japonicus, A. niger*, or *A. oryzae, Dictyostelium*, e.g., *D. discoideum; Fusarium*, e.g., *F. culmorum, F. graminearum, F. heterosporum, F. solani, F. oxysporum*, or *F. venenatum; Mucor*, e.g., *M. javanicus, M. mucedo*, or *M. subtilissimus; Neurospora*, e.g., *N. crassa; Rhizomucor*, e.g., *R. pusillus; Rhizopus*, e.g., *R. arrhizus, R. japonicus, R. stolonifer, Sclerotinia*, e.g., *S. libertiana; Trichophyton*, e.g., *T. rubrum; Whetzelinia*, e.g., *W. sclerotiorum; Bacillus*, e.g., *B. megaterium*, or *B. subtilis; Citrobacter*, e.g., *C. freundii; Enterobacter*, e.g., *E. aerogenes* or *E. cloacae; Edwardsiella, E. tarda; Erwinia*, e.g., *E. herbicola; Escherichia*, e.g., *E. coli; Klebsiella*, e.g., *K. pneumoniae; Proteus*, e.g., *P. vulgaris; Providencia*, e.g., *P. stuartii; Salmonella*, e.g., *S. typhimurium; Serratia*, e.g., *S. liquefasciens, S. marcescens; Shigella*, e.g., *S. flexneri; Streptomyces*, e.g., *S. violeceoruber*; or *Yersinia*, e.g., *Y. enterocolitica*.

Preferred commercial phospholipases include LECITASE™ and LECITASE™ ULTRA (available from Novozymes A/S, Denmark).

An effective amount of phospholipase is from about 0.01 to about 400 LU/g DS, preferably from about 0.1 to about 100 LU/g DS, and more preferably from about 1 to about 50 LU/g DS. Further optimization of the amount of phospholipase can hereafter be obtained using standard procedures known in the art.

Proteases

In another preferred embodiment of the invention, at least one surfactant and at least one carbohydrate generating enzyme is used in combination with at least one protease. The protease may be used, e.g., to digest protein to produce free amino nitrogen (FAN). Such free amino acids function as nutrients for the yeast, thereby enhancing the growth of the yeast and, consequently, the production of ethanol.

The fermenting microorganism for use in a fermentation process may be produced by propagating the fermenting microorganism in the presence of at least one protease. Although not limited to any one theory of operation, it is believed that the propagation of the fermenting microorganism with an effective amount of at least one protease reduces the lag time of the fermenting microorganism when the fermenting microorganism is subsequently used in a fermentation process as compared to a fermenting microorganism that was propagated under the same conditions without the addition of the protease. The action of the protease in the propagation process is believed to directly or indirectly result in the suppression or expression of genes which are detrimental or beneficial, respectively, to the fermenting microorganism during fermentation, thereby decreasing lag time and resulting in a faster fermentation cycle.

Proteases are well known in the art and refer to enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH 7. Suitable acid fungal proteases include fungal proteases derived from *Aspergillus, Mucor, Rhizopus, Candida, Coriolus, Endothia, Enthomophtra, Irpex, Penicillium, Sclerotium*, and *Torulopsis*. Especially contemplated are proteases derived from *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem*. 42: 927-933, *Aspergillus aculeatus* (WO 95/02044), or *Aspergillus oryzae*; and acidic proteases from *Mucor pusillus* or *Mucor miehei*.

Bacterial proteases, which are not acidic proteases, include the commercially available products ALCALASE™ and NEUTRASE™ (available from Novozymes A/S). Other proteases include GC106 from Genencor Int, Inc., USA and NOVOZYM™ 50006 from Novozymes A/S.

Preferably, the protease is an aspartic acid protease, as described, for example, in *Handbook of Proteolytic Enzymes*, Edited by A. J. Barrett, N. D. Rawlings and J. F. Woessner, Academic Press, San Diego, 1998, Chapter 270). Suitable examples of aspartic acid protease include, e.g., those disclosed by Berka et al., 1990, *Gene* 96: 313; Berka et al., 1993, *Gene* 125: 195-198; and Gomi et al., 1993, *Biosci. Biotech. Biochem.* 57: 1095-1100.

Peroxidases

Other compounds possessing peroxidase activity may be any peroxidase (EC 1.11.1.7), or any fragment having peroxidase activity derived therefrom, exhibiting peroxidase activity.

Preferably, the peroxidase is produced by plants (e.g., horseradish or soybean peroxidase) or microorganisms such as fungi or bacteria.

Some preferred fungi include strains belonging to the subdivision Deuteromycotina, class Hyphomycetes, e.g., *Fusarium, Humicola, Tricoderma, Myrothecium, Verticillum, Arthromyces, Caldariomyces, Ulocladium, Embellisia, Cladosporium*, or *Dreschlera*, in particular *Fusarium oxysporum* (DSM 2672), *Humicola insolens, Trichoderma resii, Myrothecium verrucaria* (IFO 6113), *Verticillum alboatrum, Verticillum dahlie, Arthromyces ramosus* (FERM P-7754), *Caldariomyces fumago, Ulocladium chartarum, Embellisia alli*, or *Dreschlera halodes*.

Other preferred fungi include strains belonging to the subdivision Basidiomycotina, class Basidiomycetes, e.g., *Coprinus, Phanerochaete, Coriolus*, or *Trametes*, in particular *Coprinus cinereus* f. microsporus (IFO 8371), *Coprinus macrorhizus, Phanerochaete chrysosporium* (e.g. NA-12), or *Trametes* (previously called *Polyporus*), e.g., *T. versicolor* (e.g. PR4 28-A).

Further preferred fungi include strains belonging to the subdivision Zygomycotina, class Mycoraceae, e.g., *Rhizopus* or *Mucor*, in particular *Mucor hiemalis*.

Some preferred bacteria include strains of the order Actinomycetales, e.g. *Streptomyces spheroides* (ATTC 23965), *Streptomyces thermoviolaceus* (IFO 12382), or *Streptoverticillum verticillium* ssp. *verticillium*.

Other preferred bacteria include *Rhodobacter sphaeroides, Rhodomonas palustri, Streptococcus lactis, Pseudomonas purrocinia* (ATCC 15958), *Pseudomonas fluorescens* (NRRL B-11), and *Bacillus* strains, e.g., *Bacillus pumilus* (ATCC 12905) and *Bacillus stearothermophilus*.

Further preferred bacteria include strains belonging to *Myxococcus*, e.g., *M. virescens*.

The peroxidase may also be one which is produced by a method comprising cultivating a host cell transformed with a recombinant DNA vector which carries a DNA sequence encoding the peroxidase as well as DNA sequences for expression of the DNA sequence encoding the peroxidase, in a culture medium under conditions permitting the expression of the peroxidase and recovering the peroxidase from the culture.

In a preferred embodiment, a recombinantly produced peroxidase is a peroxidase derived from a *Coprinus* sp., in particular *C. macrorhizus* or *C. cinereus* according to WO 92/16634.

In the present invention, compounds possessing peroxidase activity comprise peroxidase enzymes and peroxidase active fragments derived from cytochromes, haemoglobin, or peroxidase enzymes.

One peroxidase unit (POXU) is the amount of enzyme which under the following conditions catalyzes the conversion of 1 μmole hydrogen peroxide per minute at 30° C. in 0.1 M phosphate buffer pH 7.0, 0.88 mM hydrogen peroxide, and 1.67 mM 2,2'-azino-bis(3-ethylbenzothiazoline-6-sulfonate) (ABTS). The reaction is followed for 60 seconds (15 seconds after mixing) by the change in absorbance at 418 nm, which should be in the range of 0.15 to 0.30. For calculation of activity, an absorption coefficient of oxidized ABTS of 36 mM$^{-1}$ cm$^{-1}$ and a stoichiometry of one pmole $H_2O_2$ converted per two μmole ABTS oxidized are used.

Laccases

In the present invention, laccases and laccase related enzymes comprise any laccase enzyme classified as EC 1.10.3.2, any catechol oxidase enzyme classified as EC 1.10.3.1, any bilirubin oxidase enzyme classified as EC 1.3.3.5, or any monophenol monooxygenase enzyme classified as EC 1.14.18.1.

The above-mentioned enzymes may be microbial, i.e., obtained from bacteria or fungi (including filamentous fungi and yeasts), or they may be derived from plants.

Suitable examples from fungi include a laccase obtained from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizooctonia*, e.g., *R. solani, Coprinus*, e.g., *C. cinereus, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Pycnoporus*, e.g., *P. cinnabarinus, Phlebia*, e.g., *P. radita* (WO 92/01046), or *Coriolus*, e.g., *C. hirsutus* (JP 2-238885).

Suitable examples from bacteria include a laccase obtained from a strain of *Bacillus*.

A laccase obtained from *Coprinus, Myceliophthora, Polyporus, Pycnoporus, Scytalidium* or *Rhizoctonia* is preferred; in particular a laccase obtained from *Coprinus cinereus, Myceliophthora thermophila, Polyporus pinsitus, Pycnoporus cinnabarinus, Scytalidium thermophilum*, or *Rhizoctonia solani*.

Commercially available laccases are NS51001 (a *Polyporus pinsitius* laccase, available from Novozymes A/S, Denmark) and NS51002 (a *Myceliopthora thermophila* laccase, available from Novozymes A/S, Denmark).

The laccase or the laccase related enzyme may also be one which is produced by a method comprising cultivating a host cell transformed with a recombinant DNA vector which carries a DNA sequence encoding the laccase as well as DNA sequences for expression of the DNA sequence encoding the laccase, in a culture medium under conditions permitting the expression of the laccase enzyme, and recovering the laccase from the culture.

Laccase activity (LACU) is determined from the oxidation of syringaldazin under aerobic conditions at pH 5.5. The violet colour produced is photometered at 530 nm. The analytical conditions are 19 mM syringaldazin, 23 mM acetate buffer, pH 5.5, 30° C., 1 minute reaction time. One laccase unit (LACU) is the amount of enzyme that catalyses the conversion of 1.0 µmole syringaldazin per minute under the above conditions.

Laccase activity (LAMU) is determined from the oxidation of syringaldazin under aerobic conditions at pH 7.5. The violet colour produced is photometered at 530 nm. The analytical conditions are 19 mM syringaldazin, 23 mM Tris/maleate pH 7.5, 30° C., 1 minute reaction time. One laccase unit (LAMU) is the amount of enzyme that catalyses the conversion of 1.0 µmole syringaldazin per minute under the above conditions.

The present invention is further described by the following examples which should not be construed as limiting the scope of the invention.

EXAMPLES

Materials

Chemicals used as buffers and substrates were commercial products of at least reagent grade.

Strains

*Trichoderma reesei* RutC30 (ATCC 56765; Montenecourt and Eveleigh, 1979, *Adv. Chem. Ser.* 181: 289-301), which was derived from *Trichoderma reesei* Qm6A (ATCC 13631; Mandels and Reese, 1957, *J. Bacteriol.* 73: 269-278), was used as a host for the expression of *Aspergillus oryzae* beta-glucosidase.

*Escherichia coli* strain TOP10 cells (Invitrogen, Carlsbad, Calif.) and *Epicurian coli* SURE electroporation-competent cells (Stratagene, La Jolla, Calif.) were used for propagation of plasmids.

*Aspergillus oryzae* JaL250 strain (WO 99/61651) was used for expression of the *Aspergillus fumigatus* beta-glucosidase. *Aspergillus fumigatus* PaHa34 was used as the source of the Family GH3A beta-glucosidase.

Media and Buffer Solutions

YP medium was composed per liter of 10 g of yeast extract and 20 g of bactopeptone.

COVE selection plates were composed per liter of 342.3 g of sucrose, 20 ml of COVE salt solution, 10 mM acetamide, 15 mM CsCl$_2$, and 25 g of Noble agar.

COVE2 plates were composed per liter of 30 g of sucrose, 20 ml COVE of salt solution, 10 mM acetamide, and 25 g of Noble agar.

COVE salt solution was composed per liter of 26 g of KCl, 26 g of MgSO$_4$.7H$_2$O, 76 g of KH$_2$PO$_4$, and 50 ml of COVE trace metals solution.

COVE trace metals solution was composed per liter of 0.04 g of NaB$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_2$MoO$_2$.2H$_2$O, and 10 g of ZnSO$_4$.7H$_2$O.

Cellulase-inducing media was composed per liter of 20 g of Arbocel B800-natural cellulose fibers (J. Rettenmaier USA LP, Schoolcraft, Mich.), 10 g of corn steep solids (Sigma Chemical Co., St. Louis, Mo.), 1.45 g of (NH$_4$)$_2$SO$_4$, 2.08 g of KH$_2$PO$_4$, 0.28 g of CaCl$_2$, 0.42 g of MgSO$_4$.7H$_2$O, 0.42 ml *Trichoderma reesei* trace metals solution, and 2 drops of pluronic acid; pH to 6.0 with 10 N NaoH.

*Trichoderma reesei* trace metals solution was composed per liter of 216 g of FeCl$_3$.6H$_2$O, 58 g of ZnSO$_4$.7H$_2$O, 27 g of MnSO$_4$.H$_2$O, 10 g of CuSO$_4$.5H$_2$O, 2.4 g of H$_3$BO$_3$, and 336 g of citric acid.

PEG Buffer was composed per liter of 500 g of PEG 4000 (BDH, Poole, England), 10 mM CaCl$_2$, and 10 mM Tris-HCl pH 7.5 (filter sterilize).

STC was composed per liter of 1 M sorbitol, 10 mM CaCl$_2$, and 10 mM Tris-HCl pH 7.5 (filter sterilize).

YPD medium was composed per liter of 10 g of yeast extract, 20 g of bacto tryptone, and 40 ml of 50% glucose.

Yeast selection medium was composed per liter of 6.7 g of yeast nitrogen base, 0.8 g of complete supplement mixture (CSM, Qbiogene, Inc., Carlsbad, Calif.; missing uracil and containing 40 mg/ml of adenine), 5 g of casamino acids (without amino acids), 100 ml of 0.5 M succinate pH 5.0, 40 ml of 50% glucose, 1 ml of 100 mM CUSO$_4$, 50 mg of ampicillin, and 25 mg of chloramphenicol.

Yeast selection plate medium was composed per liter of yeast selection medium supplemented with 20 g of bacto agar and 150 mg of 5-bromo-4-chloro-3-indolyl-beta-D-glucopyranoside (X-Glc, INALCO SPA, Milano, Italy) but lacking both ampicillin and chloramphenicol.

Potato dextrose medium was composed per liter of 39 grams of potato dextrose (Difco).

PDA plates were composed per liter of 39 grams of potato dextrose agar.

MDU2BP medium was composed per liter of 45 g of maltose, 1 g of MgSO$_4$.7H$_2$O, 1 g of NaCl, 2 g of K$_2$SO$_4$, 12 g of KH$_2$PO$_4$, 7 g of yeast extract, 2 g of urea, and 0.5 ml of AMG trace metals solution, pH to 5.0.

AMG trace metals solution was composed per liter of 14.3 g of ZnSO$_4$.7H$_2$O, 2.5 g of CuSO$_4$.5H$_2$O, 0.5 g of NiCl$_2$.6H$_2$O, 13.8 g of FeSO$_4$.7H$_2$O, 8.5 g of MnSO$_4$.H$_2$O, and 3 g of citric acid.

CIM medium was composed per liter of 20 g of cellulose, 10 g of corn steep solids, 1.45 g of (NH$_4$)$_2$SO$_4$, 2.08 g of KH$_2$PO$_4$, 0.28 g of CaCl$_2$, 0.42 g of MgSO$_4$.7H$_2$O, and 0.42 ml of trace metals solution, pH to 6.0.

Trace metals solution was composed per liter of 41.2 mg of FeCl$_3$.6H$_2$O, 11.6 mg of ZnSO$_4$.7H$_2$O, 5.4 mg of MnSO$_4$.H$_2$O, 2.0 mg of CuSO$_4$.5H$_2$O, 0.48 mg of H$_3$BO$_3$, and 67.2 mg of citric acid.

Beta-Glucosidase Activity Assay

Beta-glucosidase activity was determined at ambient temperature on 25 µl of crude culture supernatants, diluted 1:10 in 50 mM succinate pH 5.0, using 200 µl of 0.5 mg/ml p-nitrophenyl-beta-D-glucopyranoside (pnpBDG) as substrate in 50 mM succinate pH 5.0. After 15 minutes incubation the reaction was stopped by adding 100 µl of 1 M Tris-HCl pH 8.0 and the absorbance was read spectrophotometrically at 405 nm. *Aspergillus niger* beta-glucosidase (Novozyme 188, Novozymes A/S, Bagsveerd, Denmark) was used as an enzyme standard.

Endoglucanase Activity Assay

The specific activity of endoglucanases towards carboxymethylcellulose (CMC, 5 mg/ml) was determined by measuring the initial rate of hydrolysis in the range of linear increase of reducing sugar (RS) concentration over time in 50 mM sodium acetate pH 5.0 at 50° C. Hydrolysis was carried out without stirring in the presence of 0.5 mg/ml BSA. Specific activity was expressed in international units (IU) per mg protein. One IU is defined as the μmol of glycosidic bonds hydrolyzed in one minute during the initial period of hydrolysis. Enzymes were diluted so as to give a linear relationship between enzyme concentration and activity measured.

Carboxymethylcellulose (type 7L2, Hercules Inc., Wilmington, Del.) with average degree of substitution (DS) of 0.7. A 6.25 mg/ml solution of CMC in 50 mM sodium acetate pH 5.0 was prepared by slowly adding CMC to vigorously agitated buffer, followed by heating to approximately 60° C. under continuous stirring until complete dissolution.

Cellobiohydrolase Activity Assay

Cellobiohydrolase activity was determined according to the procedure described by Deshpande et al. (Deshpande, M. V., Eriksson, K.-E., Pettersson, L. G., 1984, An assay for selective determination of exo-1,4-β-glucanases in a mixture of cellulolytic enzymes, *Anal. Biochem.* 138: 481-487), which was modified to a 96-well microplate format. Concentration of p-nitrophenol (PNP) produced from 2.5 mM p-nitrophenyl-β-D-cellobioside (PNPC, Cat. # 5754, Sigma, St. Louis, Mo.) was measured spectrophotometrically at 405 nm ($A_{405}$) after 30 minutes of hydrolysis in 50 mM sodium acetate pH 5.0 at 40° C. Prior to hydrolysis, the enzymes were diluted in 50 mM sodium acetate pH 5.0 to give less than 8% conversion of PNPC at the conditions specified.

Enzymes

Celluclast 1.5 L was obtained from Novozymes A/S, Bagsvaerd, Denmark. Protein concentration in cellulase samples was determined by the BCA Microplate Assay as described in the Instructions for PCS Protein Assay Reagent Kit (Pierce Chemical Co., Rockford, Ill.). Prior to determining the concentration, some samples were desalted by passing through Bio Spin 6 columns (BioRad Laboratories, Hercules, Calif.) according to the manufacturer's instructions.

Prior to hydrolysis experiments, *Aspergillus oryzae* beta-glucosidase (recombinantly produced in *Aspergillus oryzae* according to WO 02/095014), *Aspergillus fumigatis* beta-glucosidase (recombinantly produced in *Aspergillus oryzae*), and *Trichoderma reesei* endoglucanase 1 (recombinantly produced in *Aspergillus oryzae*) were desalted and exchanged into 50 mM sodium acetate pH 5.0 buffer, using Centricon Plus-20 centrifugal filter with Biomax-5 membrane (5000 NMWL; Millipore, Bedford, Mass.).

Enzyme dilutions were prepared fresh before each experiment from stock enzyme solutions, which were stored at −20° C.

Example 1

Construction of pAlLo1 Expression Vector

Expression vector pAlLo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor Site-Directed Mutagenesis Kit (Promega, Madison, Wis.) according to the manufacturer's instructions using the following primers (underlined nucleotide represents the changed base):

```
AMDS3NcoMut (2050):
5'-GTGCCCCATGATACGCCTCCGG-3'        (SEQ ID NO: 1)

AMDS2NcoMut (2721):
5'-GAGTCGTATTTCCAAGGCTCCTGACC-3'    (SEQ ID NO: 2)

AMDS1NcoMut (3396):
5'-GGAGGCCATGAAGTGGACCAACGG-3'      (SEQ ID NO: 3)
```

A plasmid comprising all three expected sequence changes was then submitted to site-directed mutagenesis, using a QuickChange Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Upper Primer to mutagenize the AMG terminator sequence:

```
                                    (SEQ ID NO: 4)
5'-CACCGTGAAAGCCATGCTCTTTCCTTCGTGTAGAAGACCAGACAG-
                                                3'
```

Lower Primer to mutagenize the AMG terminator sequence:

```
                                    (SEQ ID NO: 5)
5'-CTGGTCTTCTACACGAAGGAAAGAGCATGGCTTTCACGGTGTCTG-
                                                3'
```

Figure 3:
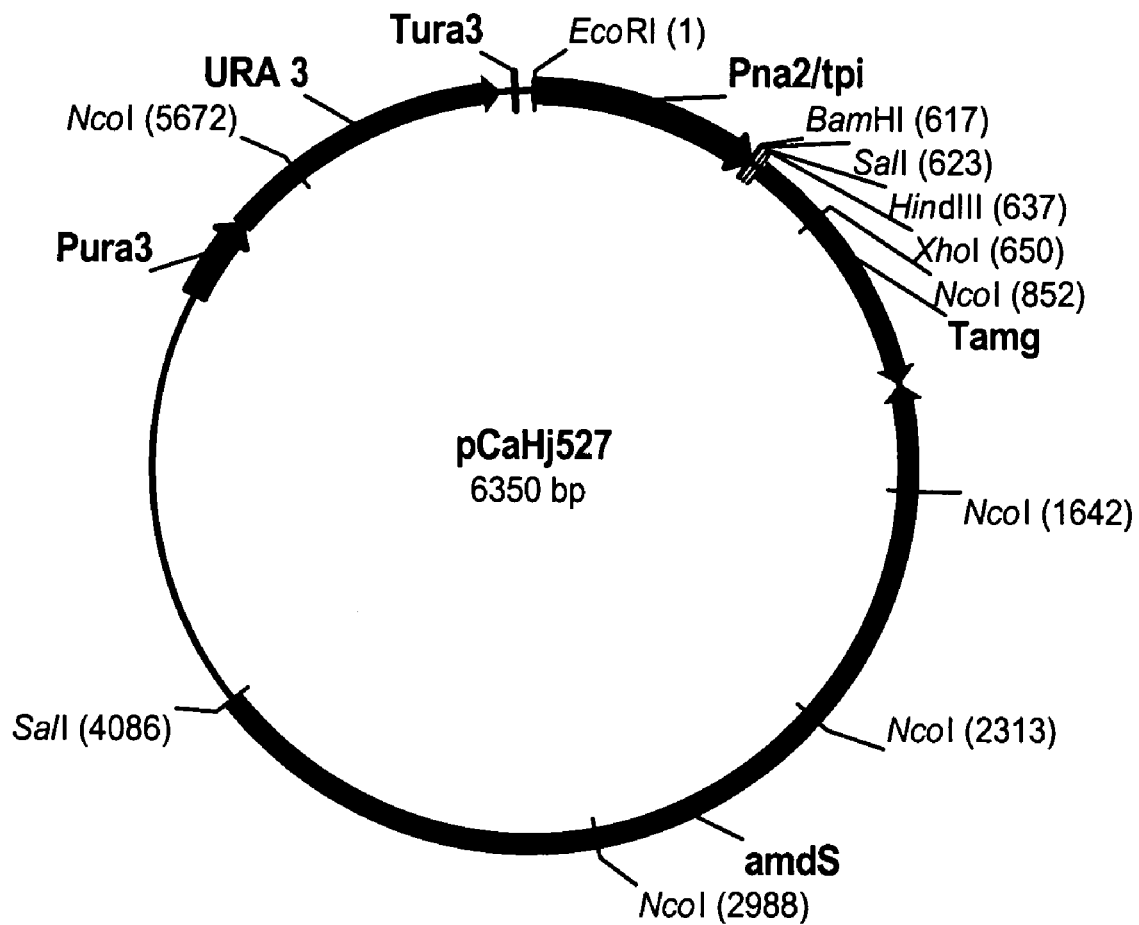
FIG. 3 shows a restriction map of pCaHj527.

The last step in the modification of pBANe6 was the addition of a new Nco I restriction site at the beginning of the polylinker using a QuickChange Mutagenesis Kit and the following primers (underlined nucleotides represent the changed bases) to yield pAlLo1 (FIG. 3).

Upper Primer to mutagenize the NA2-tpi promoter:

```
                                    (SEQ ID NO: 6)
5'-CTATATACACAACTGGATTTACCATGGGCCCGCGGCCGCAGATC-3'
```

Lower Primer to mutagenize the NA2-tpi promoter:

```
                                    (SEQ ID NO: 7)
5'-GATCTGCGGCCGCGGGCCCATGGTAAATCCAGTTGTGTATATAG-3'
```

Example 2

Construction of pMJ04 Expression Vector

Expression vector pMJ04 was constructed by PCR amplifying the *Trichoderma reesei* Cel7A cellobiohydrolase Iterminator from *Trichoderma reesei* RutC30 genomic DNA using primers 993429 (antisense) and 993428 (sense) shown below. The antisense primer was engineered to have a Pac I site at the 5'-end and a Spe I site at the 5'-end of the sense primer.

```
Primer 993429 (antisense):
5'-AACGTTAATTAAGGAATCGTTTTGTGTTT-3'    (SEQ ID NO: 8)

Primer 993428 (sense):
5'-AGTACTAGTAGCTCCGTGGCGAAAGCCTG-3'    (SEQ ID NO: 9)
```

The amplification reactions (50 µl) were composed of 1× ThermoPol Reaction Buffer (New England Biolabs, Beverly, Mass.), 0.3 mM dNTPs, 100 ng of *Trichoderma reesei* RutC30 genomic DNA (which was isolated using a DNeasy Plant Maxi Kit, QIAGEN Inc., Chatsworth, Calif.), 0.3 µM primer 993429, 0.3 µM primer 993428, and 2 units of Vent polymerase (New England Biolabs, Beverly, Mass.). The reactions were incubated in an Eppendorf Mastercycler 5333 (Hamburg, Germany) programmed as follows: 30 cycles each for 30 seconds at 94° C., 30 seconds at 55° C., and 30 seconds at 72° C. (15 minute final extension). The reaction products were isolated on a 1.0% agarose gel using 40 mM Tris base-20 mM sodium acetate-1 mM disodium EDTA (TAE) buffer where a 229 bp product band was excised from the gel and purified using a QIAquick Gel Extraction Kit (QIAGEN Inc., Chatsworth, Calif.) according to the manufacturer's instructions.

Figure 2:
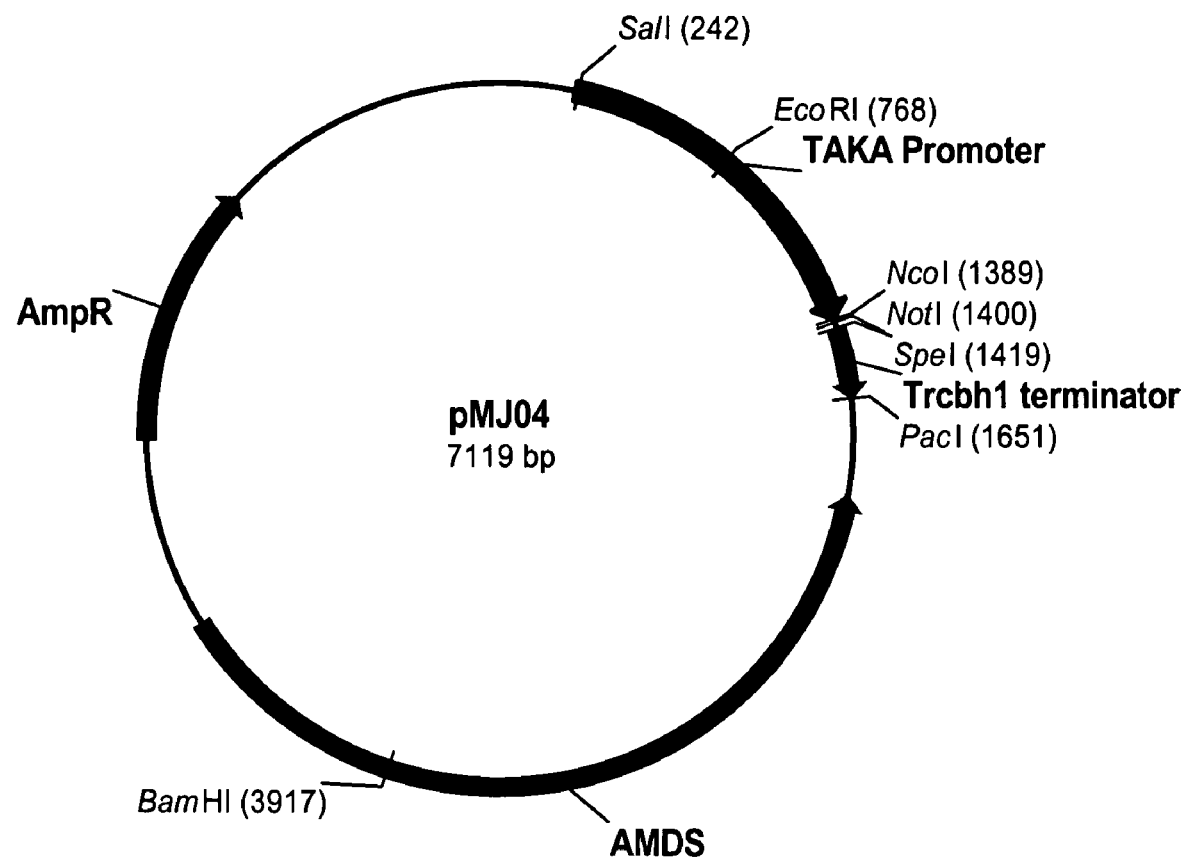
FIG. 2 shows a restriction map of pMJ04.

The resulting PCR fragment was digested with Pac I and Spe I and ligated into pAlLo1 digested with the same restriction enzymes using a Rapid Ligation Kit (Roche, Indianapolis, Ind.), to generate pMJ04 (FIG. 2).

Example 3

Construction of pCaHj568 Expression Vector

Expression plasmid pCaHj568 was constructed from pCaHj170 (U.S. Pat. No. 5,763,254) and pMT2188. Plasmid pCaHj170 comprises the *Humicola insolens* endoglucanase 5 (Cel45A) coding region. Plasmid pMT2188 was constructed as follows: The pUC19 origin of replication was PCR amplified from pCaHj483 (WO 98/00529) with primers 142779 and 142780 shown below. Primer 142780 introduces a Bbu I site in the PCR fragment.

```
142779:
                                        (SEQ ID NO: 10)
5'-TTGAATTGAAAATAGATTGATTTAAAACTTC-3'

142780:
                                        (SEQ ID NO: 11)
5'-TTGCATGCGTAATCATGGTCATAGC-3'
```

The Expand PCR System (Roche Molecular Biochemicals, Basel, Switserland) was used for the amplification following the manufacturer's instructions for this and subsequent PCR amplifications. PCR products were separated on an agarose gel and an 1160 bp fragment was isolated and purified using a Jetquick Gel Extraction Spin Kit (Genomed, Wielandstr, Germany).

The URA3 gene was amplified from the general *Saccharomyces cerevisiae* cloning vector pYES2 (Invitrogen, Carlsbad, Calif.) using primers 140288 and 142778 below. Primer 140288 introduces an Eco RI site in the PCR fragment.

```
140288:
                                        (SEQ ID NO: 12)
5'-TTGAATTCATGGGTAATAACTGATAT-3'

142778:
                                        (SEQ ID NO: 13)
5'-AAATCAATCTATTTTCAATTCAATTCATCATT-3'
```

PCR products were separated on an agarose gel and an 1126 bp fragment was isolated and purified using a Jetquick Gel Extraction Spin Kit.

The two PCR fragments were fused by mixing and amplifed using primers 142780 and 140288 shown above by overlap method splicing (Horton et al., 1989, *Gene* 77: 61-68). PCR products were separated on an agarose gel and a 2263 bp fragment was isolated and purified using a Jetquick gel extraction spin kit.

The resulting fragment was digested with EcoR I and Bbu I and ligated to the largest fragment of pCaHj483 digested with the same enzymes. The ligation mixture was used to transform pyrF *E. coli* strain DB6507 (ATCC 35673) made competent by the method of Mandel and Higa, 1970, *J. Mol. Biol.* 45: 154. Transformants were selected on solid M9 medium (Sambrook et al., 1989, Molecular Cloning, A Laboratory Manual, 2nd edition, Cold Spring Harbor Laboratory Press) supplemented per liter with 1 g of casaminoacids, 500 µg of thiamine, and 10 mg of kanamycin. A plasmid from one transformant was isolated and designated pCaHj527 (FIG. 3).

The NA2/tpi promoter present on pCaHj527 was subjected to site-directed mutagenesis by a simple PCR approach. Nucleotides 134-144 were converted from GTACTAAAACC to CCGTTAAATTT using mutagenic primer 141223:

```
Primer 141223:
                                        (SEQ ID NO: 14)
5'-GGATGCTGTTGACTCCGGAAATTTAACGGTTTGGTCTTGCATCCC-3'
```

Nucleotides 423-436 were converted from ATGCAATTTAMCT to CGGCAATTTAACGG using mutagenic primer 141222:

```
Primer 141222:
                                        (SEQ ID NO: 15)
5'-GGTATTGTCCTGCAGACGGCAATTTAACGGCTTCTGCGAATCGC-3'
```

Figure 4:
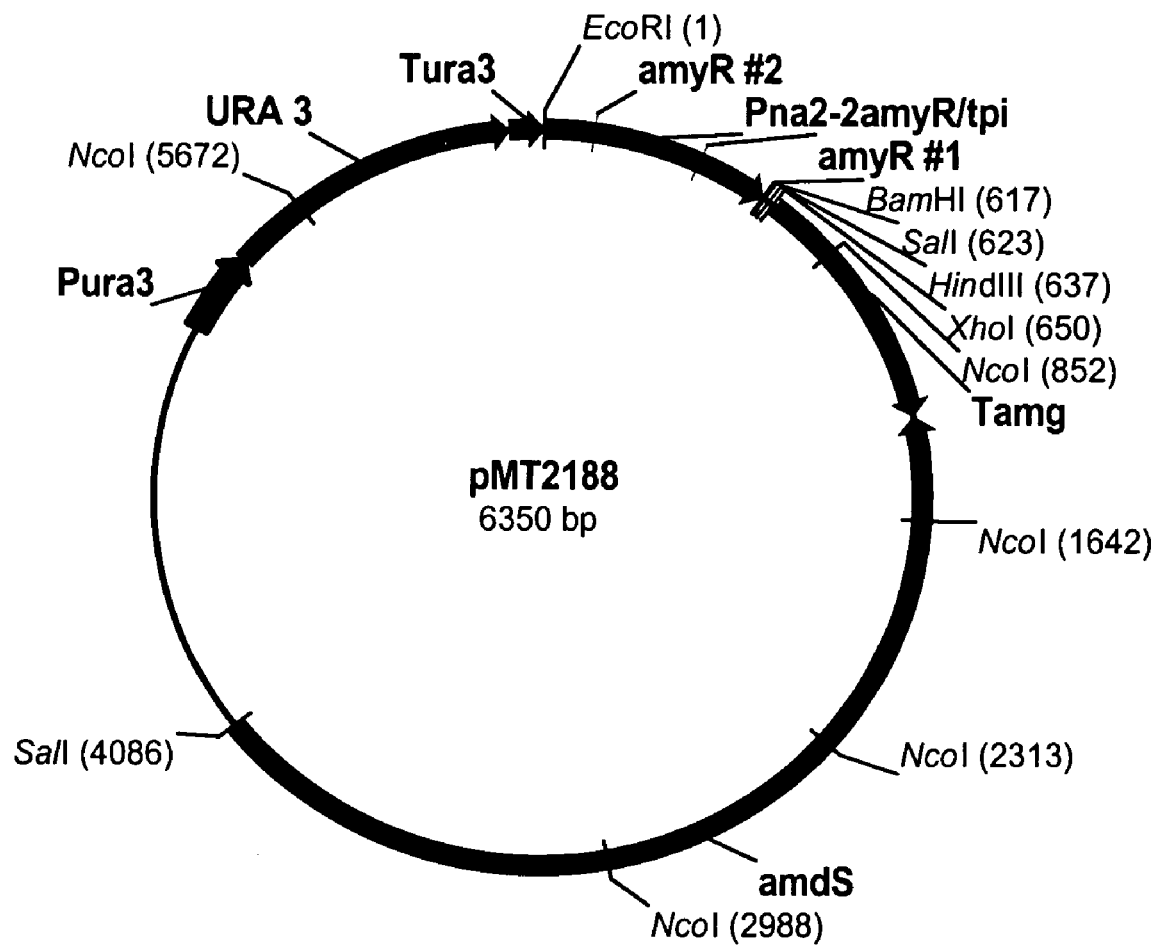
FIG. 4 shows a restriction map of pMT2188.

The resulting plasmid was designated pMT2188 (FIG. 4).

Figure 5:
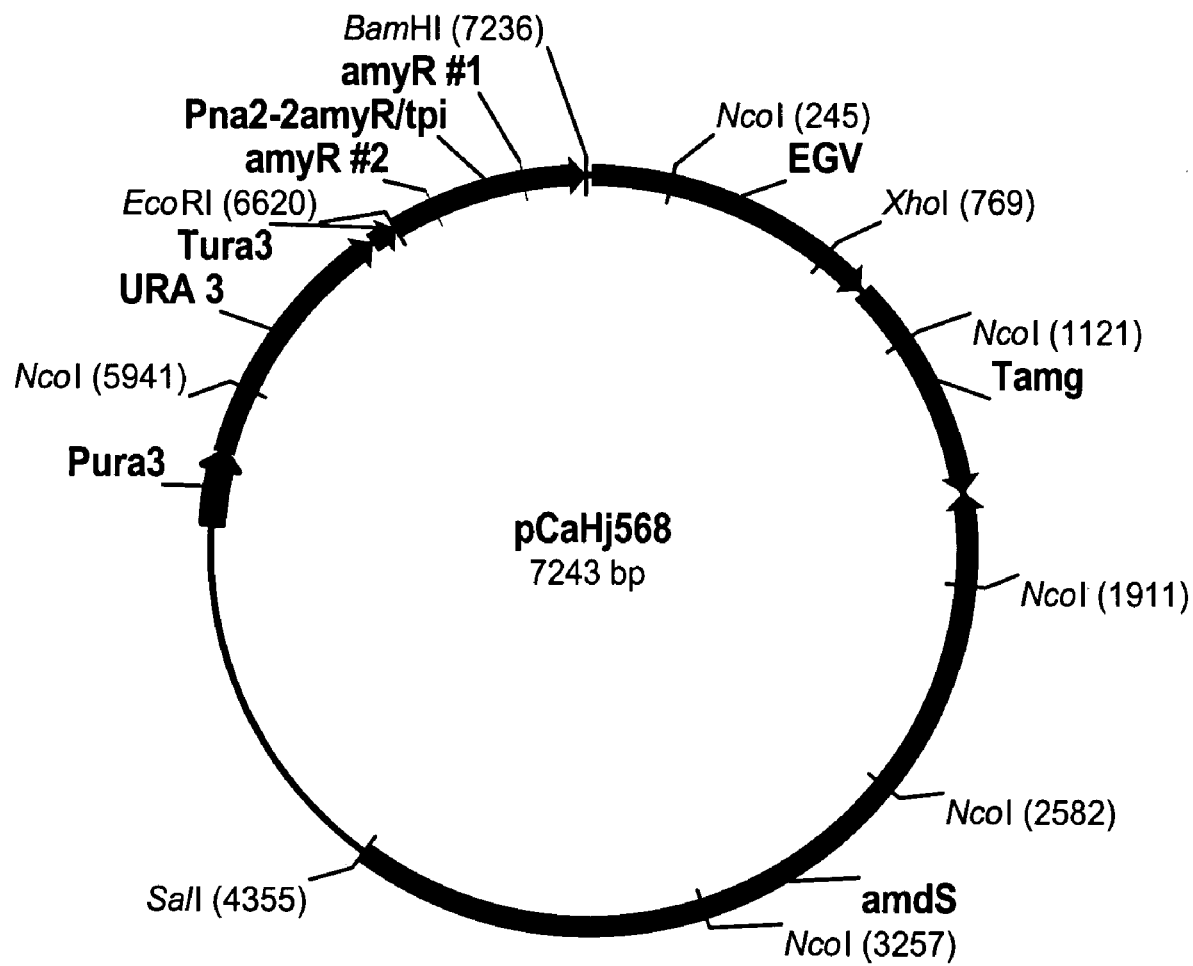
FIG. 5 shows a restriction map of pCaHj568.

The *Humicola insolens* endoglucanase 5 coding region was transferred from pCaHj170 as a Bam HI-Sal I fragment into pMT2188 digested with Bam HI and Xho I to generate pCaHj568 (FIG. 5).

Example 4

Construction of pMJ05 Expression Vector

Expression vector pMJ05 was constructed by PCR amplifying the 915 bp *Humicola insolens* endoglucanase 5 coding region from pCaHj568 using primers HiEGV-F and HiEGV-R shown below.

```
HiEGV-F (sense):
                                        (SEQ ID NO: 16)
5'-AAGCTTAAGCATGCGTTCCTCCCCCCTCC-3'

HiEGV-R (antisense):
                                        (SEQ ID NO: 17)
5'-CTGCAGAATTCTACAGGCACTGATGGTACCAG-3'
```

The amplification reactions (50 µl) were composed of 1× ThermoPol Reaction Buffer, 0.3 mM dNTPs, 10 ng/µl pCaHj568 plasmid, 0.3 µM HiEGV-F primer, 0.3 µM HiEGV-R primer, and 2 units of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65°

C., and 120 seconds at 72° C. (5 minute final extension). The reaction products were isolated on a 1.0% agarose gel using TAE buffer where a 937 bp product band was excised from the gel and purified using a QIAquick Gel Extraction Kit according to the manufacturer's instructions.

This 937 bp purified fragment was used as template DNA for subsequent amplifications using the following primers:

```
HiEGV-R (antisense):
                                         (SEQ ID NO: 18)
5'-CTGCAGAATTCTACAGGCACTGATGGTACCAG-3'

HiEGV-F-overlap (sense):
                                         (SEQ ID NO: 19)
5'-ACCGCGGACTGCGCATCATGCGTTCCTCCCCCTCC-3'
```

Primer sequences in italics are homologous to 17 bp of the *Trichoderma reesei* Cel7A cellobiohydrolase 1 promoter and underlined primer sequences are homologous to 29 bp of the *Humicola insolens* endoglucanase 5 coding region. The 36 bp overlap between the promoter and the coding sequence allowed precise fusion of the 994 bp fragment comprising the *Trichoderma reesei* Cel7A cellobiohydrolase Ipromoter to the 918 bp fragment comprising the *Humicola insolens* endoglucanase 5 open reading frame.

The amplification reactions (50 μl) were composed of 1× ThermoPol Reaction Buffer, 0.3 mM dNTPs, 1 μl of the purified 937 bp PCR fragment, 0.3 μM HiEGV-F-overlap primer, 0.3 μM HiEGV-R primer, and 2 units of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 945 bp product band was excised from the gel and purified using a QIAquick Gel Extraction Kit according to the manufacturer's instructions.

A separate PCR was performed to amplify the *Trichoderma reesei* Cel7A cellobiohydrolase 1 promoter sequence extending from 994 bp upstream of the ATG start codon of the gene from *Trichoderma reesei* RutC30 genomic DNA using the following primers (sense primer was engineered to have a Sal I restriction site at the 5'-end):

```
TrCBHIpro-F (sense):
                                         (SEQ ID NO: 20)
5'-AAACGTCGACCGAATGTAGGATTGTTATC-3'

TrCBHIpro-R (antisense):
                                         (SEQ ID NO: 21)
5'-GATGCGCAGTCCGCGGT-3'
```

The amplification reactions (50 μl) were composed of 1× ThermoPol Reaction Buffer, 0.3 mM dNTPs, 100 ng/μl *Trichoderma reesei* RutC30 genomic DNA, 0.3 μM TrCBHIpro-F primer, 0.3 μM TrCBHIpro-R primer, and 2 units of Vent polymerase. The reactions were incubated in an Eppendorf Mastercycler 5333 programmed as follows: 30 cycles each for 30 seconds at 94° C., 30 seconds at 55° C., and 120 seconds at 72° C. (5 minute final extension). The reaction products were isolated on a 1.0% agarose gel using TAE buffer where a 998 bp product band was excised from the gel and purified using a QIAquick Gel Extraction Kit according to the manufacturer's instructions.

The purified 998 bp PCR fragment was used to as template DNA for subsequent amplifications using the following primers:

```
TrCBHIpro-F:
                                         (SEQ ID NO: 22)
5'-AAACGTCGACCGAATGTAGGATTGTTATC-3'

TrCBHIpro-R-overlap:
                                         (SEQ ID NO: 23)
5'-GGAGGGGGGAGGAACGCATGATGCGCAGTCCGCGGT-3'
```

Sequences in italics are homologous to the 17 bp of the *Trichoderma reesei* cbh1 promoter and underlined sequences are homologous to the 29 bp of the *Humicola insolens* endoglucanase 5 coding region. The 36 bp overlap between the promoter and the coding sequence allowed precise fusion of the 994 bp fragment comprising the *Trichoderma reesei* Cel7A promoter to the 918 bp fragment comprising the *Humicola insolens* endoglucanase 5 open reading frame.

The amplification reactions (50 μl) were composed of 1× ThermoPol Reaction Buffer, 0.3 mM dNTPs, 1 μl of the purified 998 bp PCR fragment, 0.3 μM TrCBH1pro-F primer, 0.3 μM TrCBH1pro-R-overlap primer, and 2 units of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1017 bp product band was excised from the gel and purified using a QIAquick Gel Extraction Kit according to the manufacturer's instructions.

The 1017 bp *Trichoderma reesei* Cel7A cellobiohydrolase 1 promoter PCR fragment and the 945 bp *Humicola insolens* endoglucanase 5 PCR fragment were used as template DNA for subsequent amplification using the following primers to precisely fuse the 994 bp *Trichoderma reesei* Cel7A cellobiohydrolase Ipromoter to the 918 bp *Humicola insolens* endoglucanase 5 coding region using overlapping PCR.

```
TrCBHIpro-F:
                                         (SEQ ID NO: 24)
5'-AAACGTCGACCGAATGTAGGATTGTTATC-3'

TrCBHIpro-F:
                                         (SEQ ID NO: 25)
5'-CTGCAGAATTCTACAGGCACTGATGGTACCAG-3'
```

The amplification reactions (50 μl) were composed of 1× ThermoPol Reaction Buffer, 0.3 mM dNTPs, 0.3 μM TrCBH1pro-F primer, 0.3 μM HiEGV-R primer, and 2 units of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1926 bp product band was excised from the gel and purified using a QIAquick Gel Extraction Kit according to the manufacturer's instructions.

Figure 6:
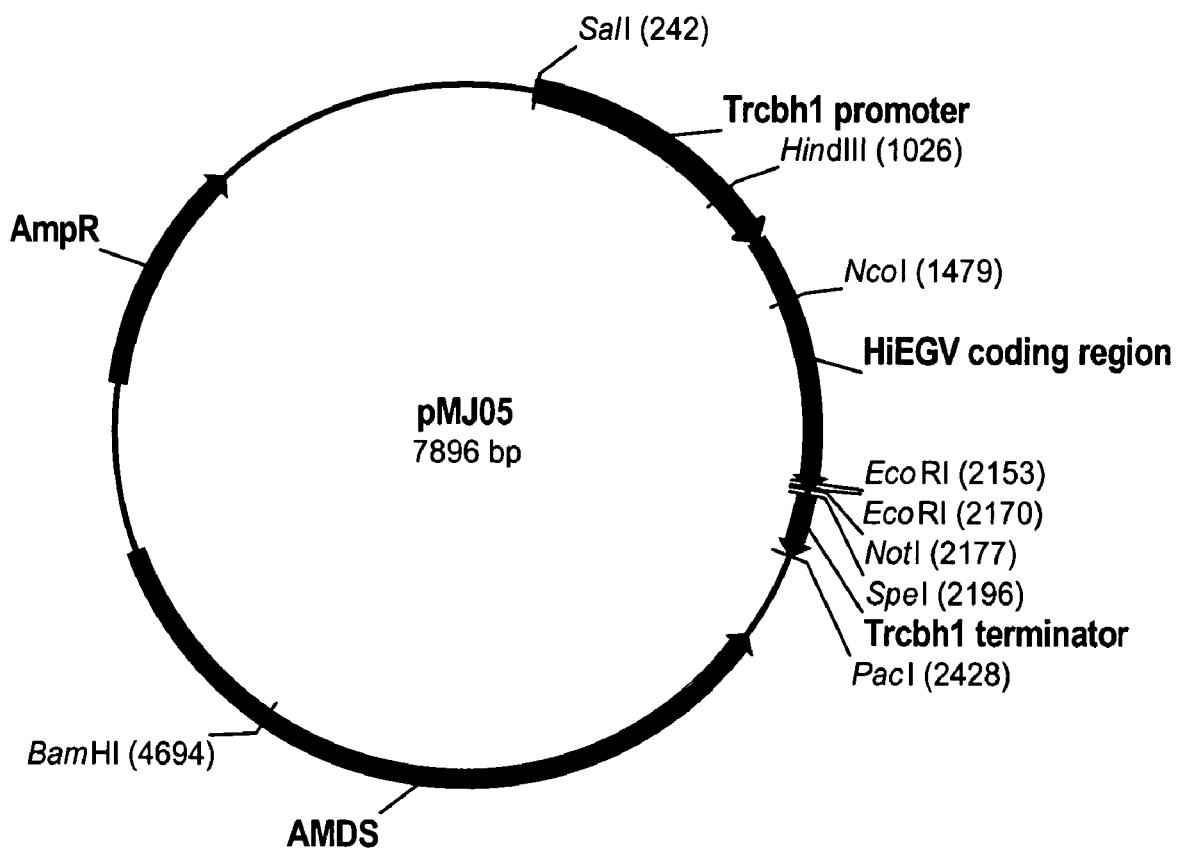
FIG. 6 shows a restriction map of pMJ05.

The resulting 1926 bp fragment was cloned into pCR-Blunt-II-TOPO vector (Invitrogen, Carlsbad, Calif.) using a ZeroBlunt TOPO PCR Cloning Kit following the manufacturer's protocol. The resulting plasmid was digested with Not I and Sal I and the 1926 bp fragment purified and ligated into pMJ04, which was also digested with the same two restriction enzymes, to generate pMJ05 (FIG. 6).

Example 5

Construction of pSMai135

The *Aspergillus oryzae* beta-glucosidase coding region (WO 2002/095014, *E. coli* DSM 14240, minus the putative signal sequence, see FIG. 7, SEQ ID NOs: 26 and 27) from Lys-20 to the TAA stop codon was PCR amplified from pJaL660 (WO 2002/095014) as template with primer 993728 (sense) and primer 993727 (antisense) shown below. Sequences in italics are homologous to 20 bp of the *Humicola insolens* endoglucanase 5 signal sequence and sequences underlined are homologous to 22 bp of the *Aspergillus oryzae* beta-glucosidase coding region. A Spe I site was engineered into the 5' end of the antisense primer.

```
TrCBHIpro-F:
                                    (SEQ ID NO: 28)
5'-TGCCGGTGTTGGCCCTTGCC
AAGGATGATCTCGCGTACTCCC-3'

Primer 993727:
                                    (SEQ ID NO: 29)
5'-GACTAGTCTTACTGGGCCTTAGGCAGCG-3'
```

The amplification reactions (50 µl) were composed of Pfx Amplification Buffer, 0.25 mM dNTPs, 10 ng/µl pJaL660, 6.4 µM primer 993728, 3.2 µM primer 993727, 1 mM MgCl$_2$, and 2.5 units of Pfx polymerase. The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 2523 bp product band was excised from the gel and purified using a QIAquick Gel Extraction Kit according to the manufacturer's instructions.

A separate PCR amplification was performed to amplify 1000 bp of the *Trichoderma reesei* Cel7A cellobiohydrolase 1 promoter and 63 bp of the putative *Humicola insolens* endoglucanase 5 signal sequence (ATG start codon to Ala-21, FIG. 8, SEQ ID NOs: 30 (DNA sequence) and 31 (deduced amino acid sequence); accession no. AAB03660 for DNA sequence), using primer 993724 (sense) and primer 993729 (antisense) shown below. Primer sequences in italics are homologous to 20 bp of the *Humicola insolens* endoglucanase 5 signal sequence and underlined primer sequences are homologous to 22 bp of the *Aspergillus oryzae* beta-glucosidase coding region. Plasmid pMJ05, which comprises the *Humicola insolens* endoglucanase 5 coding region under the control of the *Trichoderma reesei* Cel7A cellobiohydrolase 1 promoter, was used as a template to generate a 1063 bp fragment comprising the *Trichoderma reesei* Cel7A cellobiohydrolase 1 promoter/*Humicola insolens* endoglucanase 5 signal sequence fragment. A 42 bp of overlap was shared between the *Trichoderma reesei* Cel7A promoter/*Humicola insolens* endoglucanase 5 signal sequence and the *Aspergillus oryzae* coding sequence to provide a perfect linkage between the promoter and the ATG start codon of the 2523 bp *Aspergillus oryzae* beta-glucosidase.

```
Primer 993724:
                                    (SEQ ID NO: 32)
5'-ACGCGTCGACCGAATGTAGGATTGTTATCC-3'

Primer 993729:
                                    (SEQ ID NO: 33)
5'-GGGAGTACGCGAGATCATCCTTGGCAAGGGCCAACACCGGCA-3'
```

The amplification reactions (50 µl) were composed of Pfx Amplification Buffer, 0.25 mM dNTPs, 10 ng/µl pMJ05, 6.4 µM primer 993728, 3.2 µM primer 993727, 1 mM MgCl$_2$, and 2.5 units of Pfx polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension). The reaction products were isolated on a 1.0% agarose gel using TAE buffer where a 1063 bp product band was excised from the gel and purified using a QIAquick Gel Extraction Kit according to the manufacturer's instructions.

The purified overlapping fragments were used as a template for amplification using primer 993724 (sense) and primer 993727 (antisense) described above to precisely fuse the 1063 bp *Trichoderma reesei* Cel7A cellobiohydrolase 1 promoter/*Humicola insolens* endoglucanase V5signal sequence fragment to the 2523 bp of *Aspergillus oryzae* beta-glucosidase by overlapping PCR.

The amplification reactions (50 µl) were composed of Pfx Amplification Buffer, 0.25 mM dNTPs, 6.4 µM primer 993724, 3.2 µM primer 993727, 1 mM MgCl$_2$, and 2.5 units of Pfx polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension). The reaction products were isolated on a 1.0% agarose gel using TAE buffer where a 3591 bp product band was excised from the gel and purified using a QIAquick Gel Extraction Kit according to the manufacturer's instructions.

Figure 9:
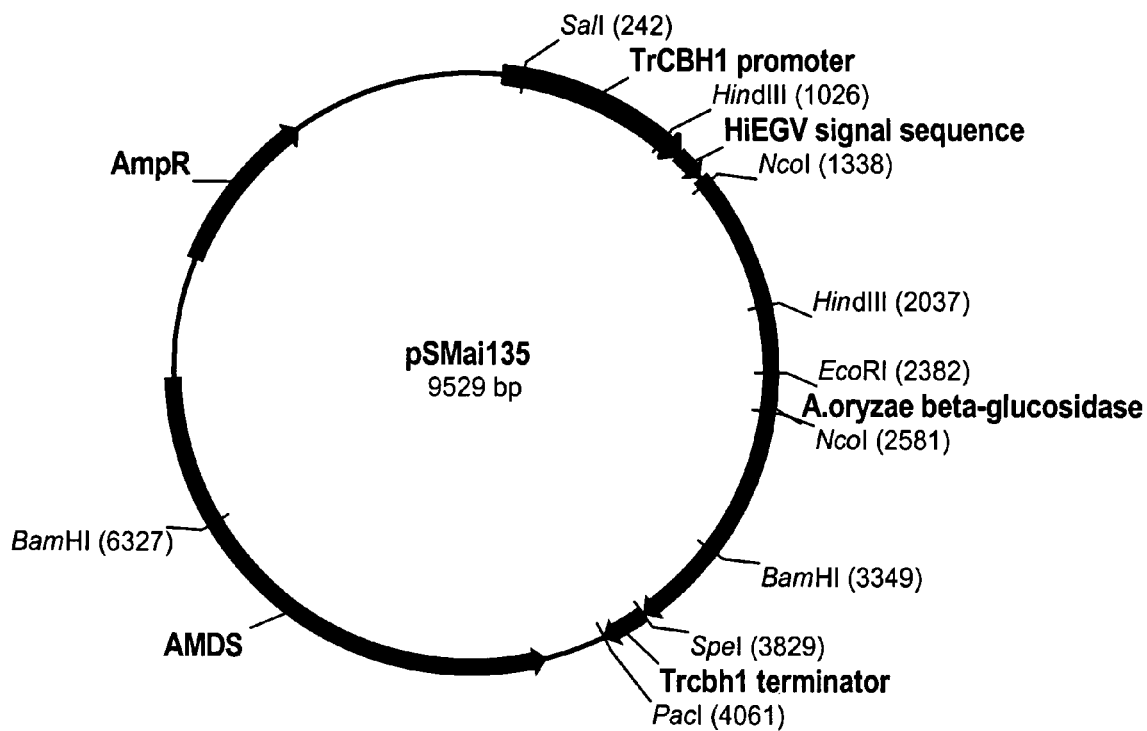
FIG. 9 shows a restriction map of pSMai135.

The resulting 3591 bp fragment was digested with Sal I and Spe I and ligated into pMJ04 digested with the same restriction enzymes to generate pSMai135 (FIG. 9).

Example 6

Expression of *Aspergillus oryzae* Beta-Glucosidase in *Trichoderma reesei*

Plasmid pSMai135 encoding the mature *Aspergillus oryzae* beta-glucosidase enzyme, linked to *Humicola insolens* endoglucanase 5 secretion signal (FIG. 8, SEQ ID NOs: 30 (DNA sequence) and 31 (deduced amino acid sequence), was introduced into *Trichoderma reesei* RutC30 by PEG-mediated transformation. The expression plasmid contains the *Aspergillus nidulans* amdS gene to enable transformants to grow on acetamide as the sole nitrogen source.

Protoplast preparation and transformation was performed using a modified protocol by Penttila et al., 1987, *Gene* 61: 155-164. Briefly, *Trichoderma reesei* RutC30 was cultivated at 27° C. and 90 rpm in 25 ml of YP medium supplemented with 2% (w/v) glucose and 10 mM uridine for 17 hours. Mycelia was collected by filtration using Millipore's Vacuum Driven Disposable Filtration System (Millipore, Bedford, Mass.) and washed twice with deionized water and twice with 1.2 M sorbitol. Protoplasts were generated by suspending the washed mycelia in 20 ml of 1.2 M sorbitol containing 15 mg of Glucanex (Novozymes A/S, Bagsvaerd, Denmark) per ml and 0.36 units of chitinase (Sigma Chemical Co., St. Louis, Mo.) per ml and incubating for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and re-suspended in STC to a final concentration of 1×10$^8$ protoplasts per ml. Excess protoplasts were stored in a Cryo 1° C. Freezing Container (Nalgene, Rochester, N.Y.) at −80° C.

Approximately 7 µg of pSMai135 digested with Pme I was added to 100 µl of protoplast solution and mixed gently, followed by 260 µl of PEG buffer, mixed, and incubated at room temperature for 30 minutes. STC (3 ml) was then added, mixed and the transformation solution was plated onto COVE plates using *Aspergillus nidulans* amdS selection. The plates were incubated at 28° C. for 5-7 days. Transformants were sub-cultured onto COVE2 plates and grown at 28° C.

Sixty-seven transformants (SMA135-01 to SMA135-67) harboring the *Aspergillus oryzae* beta-glucosidase gene were randomly selected and cultured in 125 ml baffled shake flasks containing 25 ml of cellulase-inducing media at 28° C. and 200 rpm for 7 days. *Trichoderma reesei* RutC30 was run as a control. Culture broth samples were removed 7 days post-inoculation, centrifuged at 15,700×g for 5 minutes in a micro-centrifuge, and the supernatants transferred to new tubes. Samples were stored at 4° C. until enzyme assay. The supernatants were assayed for beta-glucosidase activity using p-nitrophenyl-beta-D-glucopyranoside as substrate, as described above.

A number of SMA135 transformants showed beta-glucosidase activities several fold more than that of *Trichoderma reesei* RutC30. Transformant SMA135-04 produced the highest beta-glucosidase activity having 7 times more beta-glucosidase activity than produced by *Trichoderma reesei* RutC30 as a control.

SDS polyacrylamide electrophoresis was carried out using Criterion Tris-HCl (5% resolving) gels (BioRad, Hercules, Calif.) with The Criterion System (BioRad, Hercules, Calif.). Five μl of day 7 supernatants (see above) were suspended in 2× concentration of Laemmli Sample Buffer (BioRad, Hercules, Calif.) and boiled for 3 minutes in the presence of 5% beta-mercaptoethanol. The supernatant samples were loaded onto a polyacrylamide gel and subjected to electrophoresis with 1× Tris/Glycine/SDS as running buffer (BioRad, Hercules, Calif.). The resulting gel was stained with BioRad's Bio-Safe Coomassie Stain.

Twenty-six of the 67 *Trichoderma reesei* SMA135 transformants produced a protein of approximately 110 kDa that was not visible in the host strain, *Trichoderma reesei* RutC30. *Trichoderma reesei* transformant, SMA135-04, produced the highest level of beta-glucosidase.

Example 7

Production of Recombinant *Aspergillus oryzae* Beta-Glucosidase in *Trichoderma reesei* by Fermentation Fermentation was performed on *Trichoderma reesei* strain SMA135-04 to produce quantities of *Aspergillus oryzae* beta-glucosidase. *Trichoderma reesei* RutC30 (host strain) was run as a control. Fermentations were performed using the standard conditions as described by Mandels and Weber, 1969, *Adv. Chem. Ser.* 95: 391-413) on 2% cellulose. The fermentations ran for 165 hours at which time the final fermentation broths were centrifuged and the supernatants stored at −20° C. until beta-glucosidase activity assay using the procedure described earlier.

Beta-glucosidase activity on the *Trichoderma reesei* SMA135-04 fermentation sample was determined to be approximately 8 times more active than that of *Trichoderma reesei* RutC30.

Example 8

Identification of a Beta-Glucosidase Family GH3A Gene in the Genomic Sequence of *Aspergillus fumigatus*

A Blast search (Altschul et al., 1997, *Nucleic Acids Res.* 25: 3389-3402) of the *Aspergillus fumigatus* partial genome sequence (The Institute for Genomic Research, Rockville, Md.) was carried out using as query a beta-glucosidase protein sequence from *Aspergillus aculeatus* (Accession No. P48825). Several genes were identified as putative Family GH3A homologs based upon a high degree of similarity to the query sequence at the amino acid level. One genomic region of approximately 3000 bp with greater than 70% identity to the query sequence at the amino acid level was chosen for further study.

Example 9

*Aspergillus fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in TE (10 mM Tris-1 mM EDTA), and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase free RNase A was added at a concentration of 20 mg/liter and the lysate was incubated at 37° C. for 30 minutes. Cellular debris was removed by centrifugation, and DNA was isolated by using a Qiagen Maxi 500 column (QIAGEN Inc., Chatsworth, Calif.). The columns were equilibrated in 10 ml of QBT washed with 30 ml of QC, and eluted with 15 ml of QF (all buffers from QIAGEN Inc., Chatsworth, Calif.). DNA was precipitated in isopropanol, washed in 70% ethanol, and recovered by centrifugation. The DNA was resuspended in TE buffer.

Example 10

Construction of pAlLo2 Expression Vector

Figure 11:
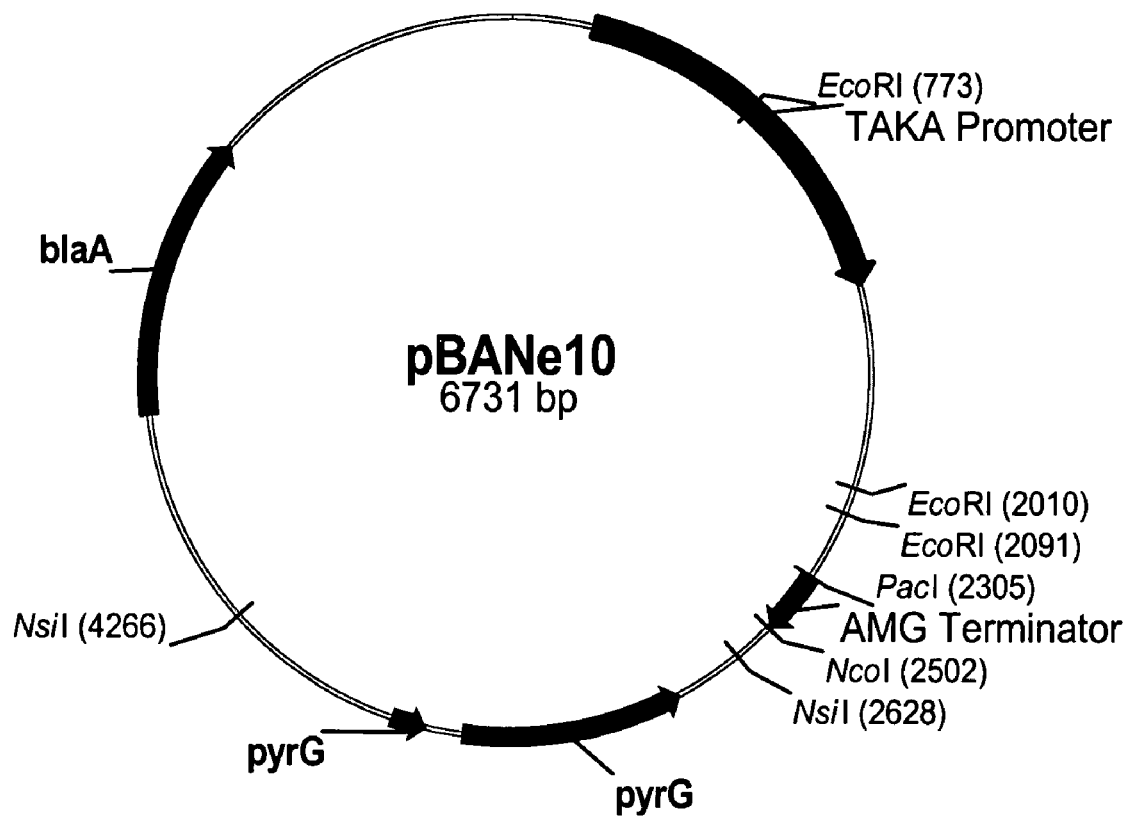
FIG. 11 shows a restriction map of pBANe10.
Figure 12:
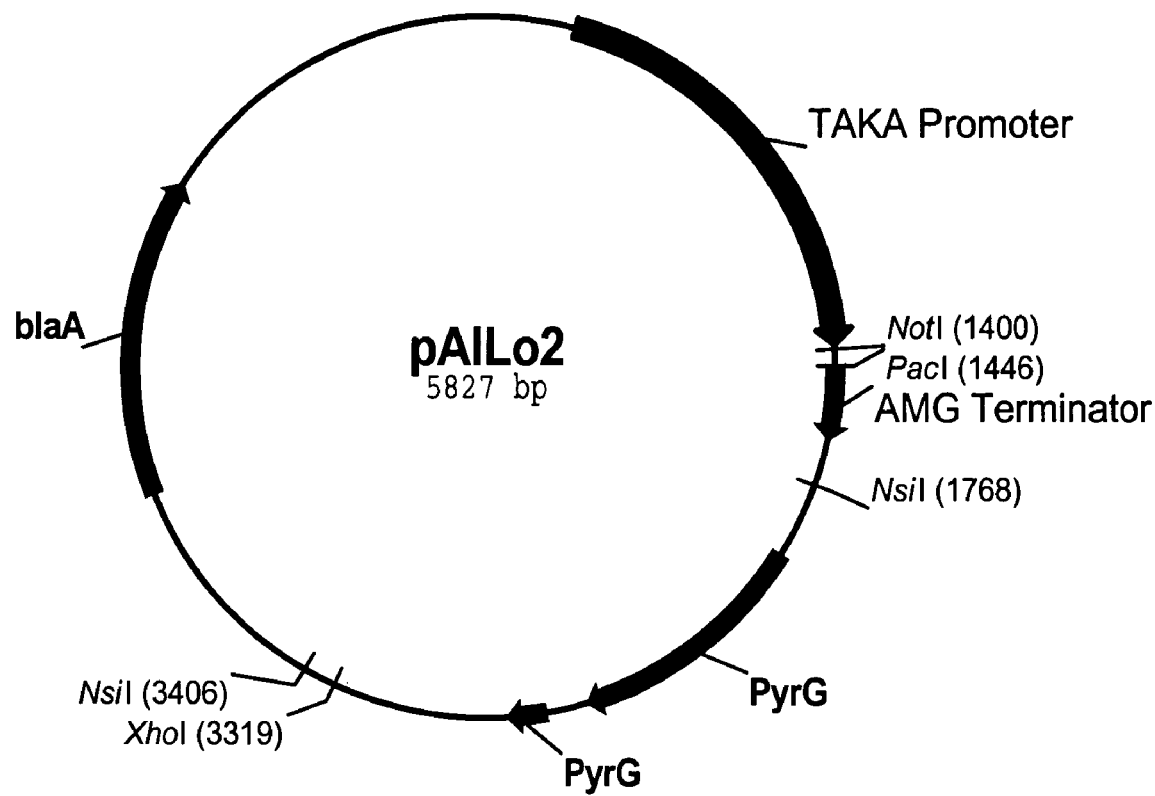
FIG. 12 shows a restriction map of pAlLo2.

The amdS gene of pAlLo1 (Example 1) was swapped with the *Aspergillus nidulans* pyrG gene. Plasmid pBANe10 (FIG. 11) was used as a source for the pyrg gene. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAlLo1 and pBANe10 were digested with the restriction enzyme Nsi I and the products purified by agarose gel electrophoresis using standard procedures. The Nsi I fragment from pBANe10 containing the pyrG gene was ligated to the backbone of pAlLo1 to replace the original Nsi I DNA fragment containing the amdS gene. Recombinant clones were analyzed by restriction digest to determine whether they had the correct insert and correct orientation. A clone with the pyrg gene transcribed in the counterclockwise direction was selected. The new plasmid was designated pAlLo2 (FIG. 12).

Example 11

Cloning of the Family GH3A Beta-Glucosidase Gene and Construction of an *Aspergillus oryzae* Expression Vector Two synthetic oligonucleotide primers shown below were designed to PCR amplify a *Aspergillus fumigatus* gene encoding a Family GH3A beta-glucosidase from the genomic DNA prepared in Example 9. An InFusion Cloning Kit (BD Biosciences, Palo Alto, Calif.) was used to clone the fragment directly into the expression vector, pAlLo2, without the need for restriction digests and ligation.

```
Forward primer:
                                            (SEQ ID NO: 34)
5'-ACTGGATTTACCATGAGATTCGGTTGGCTCG-3'

Reverse primer:
                                            (SEQ ID NO: 35)
5'-AGTCACCTCTAGTTACTAGTAGACACGGGGC-3'
```

Bold letters represent coding sequence. The remaining sequence is homologous to the insertion sites of pAlLo2.

Fifty picomoles of each of the primers above were used in a PCR reaction containing 100 ng of *Aspergillus fumigatus* genomic DNA, 1× Pfx Amplification Buffer (Invitrogen, Carlsbad, Calif.), 1.5 µl of 10 mM blend of dATP, dTTP, dGTP, and dCTP, 2.5 units of Platinum Pfx DNA Polymerase (Invitrogen, Carlsbad, Calif.), 1 µl of 50 mM MgSO$_4$ and 2.5 µl of 10×pCRx Enhancer solution (Invitrogen, Carlsbad, Calif.) in a final volume of 50 µl. The amplification conditions were one cycle at 94° C. for 2 minutes; 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAquick Gel Extraction Kit according to the manufacturer's instructions.

Figure 13:
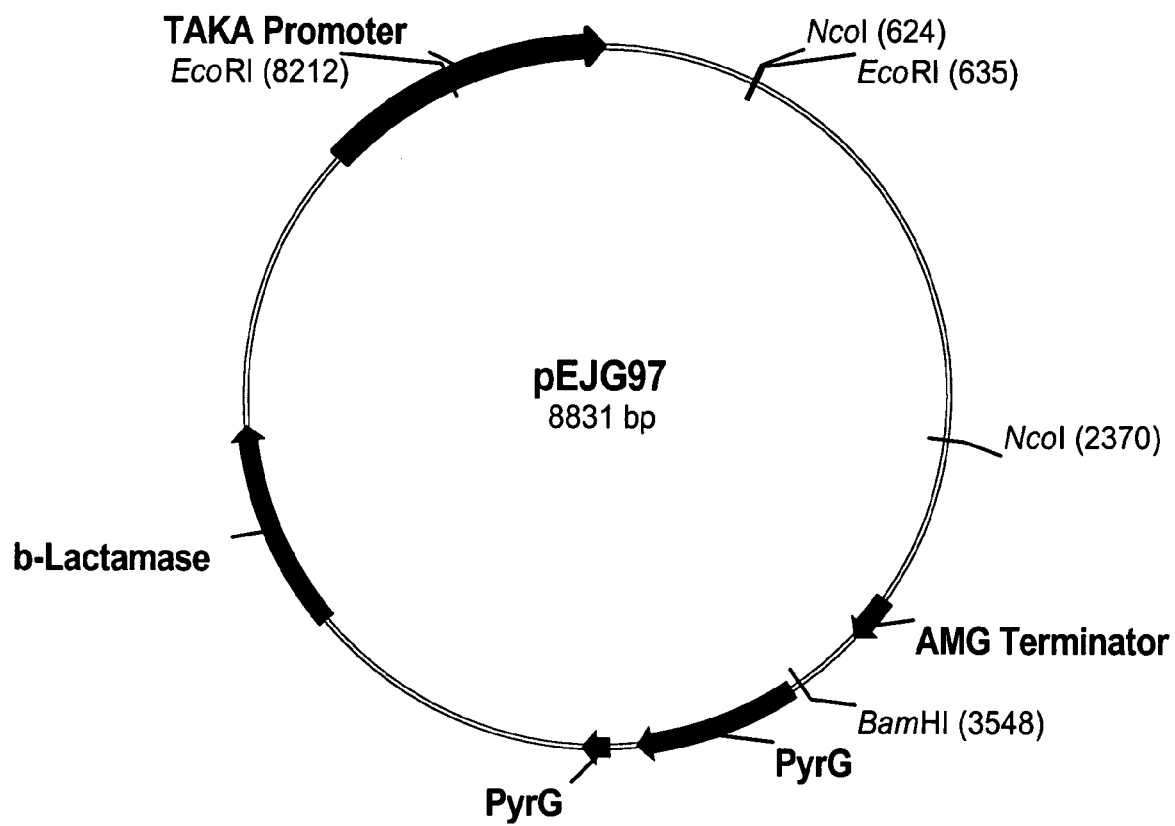
FIG. 13 shows a restriction map of pEJG97.

The fragment was then cloned into the pAlLo2 expression vector using an Infusion Cloning Kit. The vector was digested with restriction endonucleases Nco I and Pac I (using conditions specified by the manufacturer). The fragment was purified by gel electrophoresis and QIAquick Gel Extraction Kit. The gene fragment and digested vector were ligated together in a reaction resulting in the expression plasmid pEJG97 (FIG. 13) in which transcription of the Family GH3A beta-glucosidase gene was under the control of the NA2-tpi promoter. The ligation reaction (50 µl) was composed of 1× InFusion Buffer (BD Biosciences, Palo Alto, Calif.), 1×BSA (BD Biosciences, Palo Alto, Calif.), 1 µl of Infusion enzyme (diluted 1:10) (BD Biosciences, Palo Alto, Calif.), 150 ng of pAlLo2 digested with Nco I and Pac 1, and 50 ng of the *Aspergillus fumigatus* beta-glucosidase purified PCR product. The reaction was incubated at room temperature for 30 minutes. One µl of the reaction was used to transform *E. coli* XL10 Solopac Gold cells (Stratagene, La Jolla, Calif.). An *E. coli* transformant containing the pEJG97 plasmid was detected by restriction digestion and plasmid DNA was prepared using a BioRobot 9600 (QIAGEN Inc., Chatsworth, Calif.)

Example 12

Characterization of the *Aspergillus fumigatus* Genomic Sequence Encoding a Family GH3A Beta-Glucosidase DNA sequencing of the *Aspergillus fumigatus* beta-glucosidase gene from pEJG97 was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

A gene model for the *Aspergillus fumigatus* sequence was constructed based on similarity to homologous genes from *Aspergillus aculeatus, Aspergillus niger*, and *Aspergillus kawachii*. The nucleotide sequence (SEQ ID NO: 36) and deduced amino acid sequence (SEQ ID NO: 37) are shown in FIG. 10. The genomic fragment encodes a polypeptide of 863 amino acids, interrupted by 8 introns of 62, 55, 58, 63, 58, 58, 63 and 51 bp. The % G+C content of the gene is 54.3%. Using the SignalP software program (Nielsen et al., 1997, *Protein Engineering* 10: 1-6), a signal peptide of 19 residues was predicted. The predicted mature protein contains 844 amino acids with a molecular mass of 91.7 kDa.

A comparative alignment of beta-glucosidase sequences was determined using the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* beta-glucosidase gene shared 78%, 76%, and 76% identity to the deduced amino acid sequences of the *Aspergillus aculeatus* (accession number P48825), *Aspergillus niger* (accession number O00089), and *Aspergillus kawachii* (accession number P87076) beta-glucosidases.

Example 13

Expression of the *Aspergillus fumigatus* Family GH3A Beta-Glucosidase Gene in *Aspergillus oryzae* JaL250

*Aspergillus oryzae* JaL250 protoplasts were prepared according to the method of Christensen et al., 1988, *Bio/Technology* 6: 1419-1422. Five µg of pEJG97 (as well as pAlLo2 as a vector control) was used to transform *Aspergillus oryzae* JaL250.

The transformation of *Aspergillus oryzae* JaL250 with pEJG97 yielded about 100 transformants. Ten transformants were isolated to individual PDA plates.

Confluent PDA plates of five of the ten transformants were washed with 5 ml of 0.01% Tween 20 and inoculated separately into 25 ml of MDU2BP medium in 125 ml glass shake flasks and incubated at 34° C., 250 rpm. Five days after incubation, 0.5 µl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that one of the transformants (designated transformant 1) had a major band of approximately 130 kDa.

A confluent plate of transformant 1 (grown on PDA) was washed with 10 ml of 0.01% Tween 20 and inoculated into a 2 liter Fernbach containing 400 ml of MDU2BP medium to generate broth for characterization of the enzyme. The flask was harvested on day 5 and filtered using a 0.22 µm GP Express plus Membrane (Millipore, Bedford, Mass.).

Prior to hydrolysis experiments, *Aspergillus oryzae* beta-glucosidase (recombinantly produced in *Aspergillus oryzae*) was desalted and exchanged to 50 mM sodium acetate pH 5.0 buffer, using a Centricon Plus-20 centrifugal filter with Biomax-5 membrane (5000 NMWL; Millipore, Bedford, Mass.).

Example 14

Construction of pMJ09

Vector pMJ06 was constructed by PCR amplifying the *Trichoderma reesei* Cel7A cellobiohydrolase 1 gene (cbh1) promoter from *Trichoderma reesei* RutC30 genomic DNA using primers 993696 (antisense) and 993695 (sense) shown below. The antisense primer was engineered to have a Sal I site at the 5'-end of the sense primer and an Nco I site at the 5'-end of the antisense primer.

```
Primer 993695 (sense):
                                 (SEQ ID NO: 38)
5'-ACTAGTCGACCGAATGTAGGATTGTT-3'

Primer 993696 (antisense):
                                 (SEQ ID NO: 39)
5'-TGACCATGGTGCGCAGTCC-3'
```

The amplification reactions (50 µl) were composed of 1× ThermoPol Reaction Buffer, 0.3 mM dNTPs, 100 ng *Trichoderma reesei* RutC30 genomic DNA (which was prepared using a QIAGEN DNeasy Plant Maxi Kit), 0.3 µM primer 993696, 0.3 µM primer 993695, and 2 units of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension).

The reaction products were isolated on a 1.0% agarose gel using TAE buffer where a 988 bp product band was excised from the gel and purified using a QIAGEN QIAquick Gel Extraction Kit according to the manufacturer's instructions.

Figure 14:
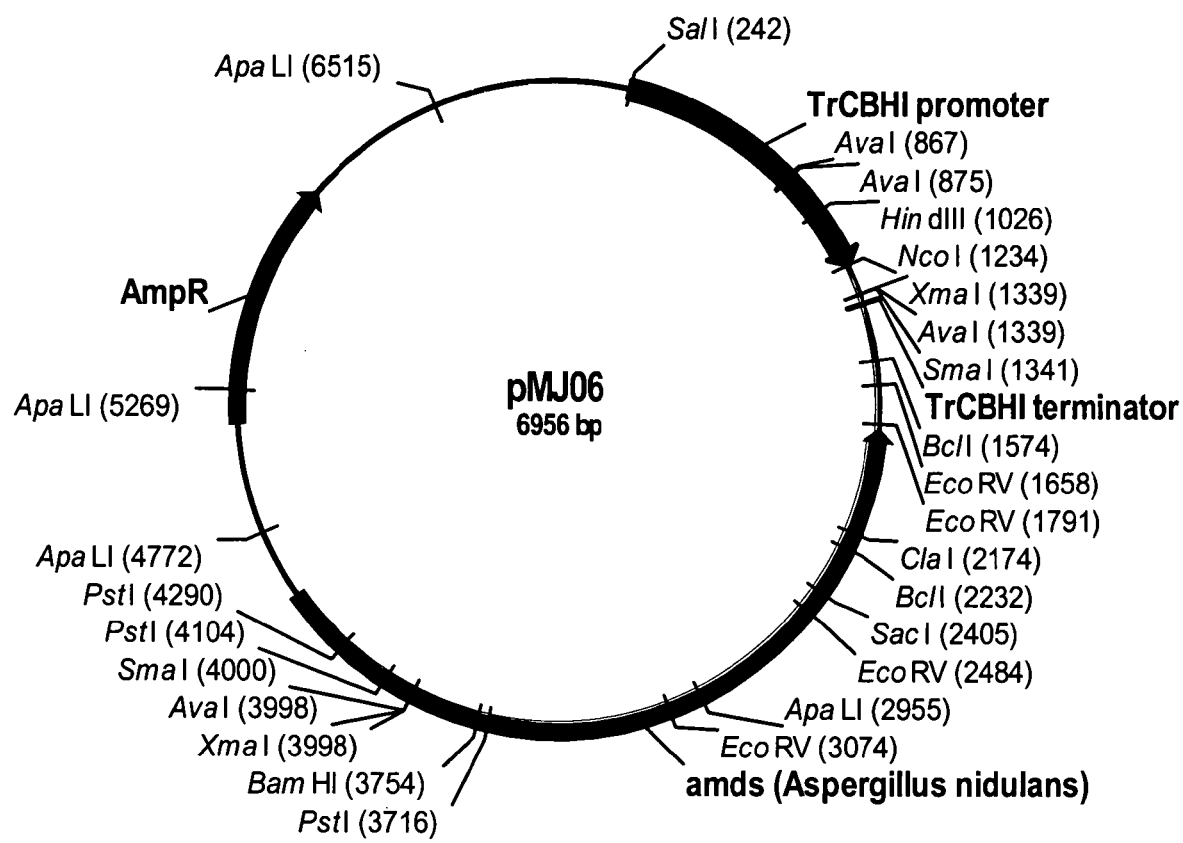
FIG. 14 shows a restriction map of pMJ06.

The resulting PCR fragment was digested with Nco I and Sal I and ligated into pMJ04 digested with the same restriction enzymes, using a Rapid Ligation Kit, to generate pMJ06 (FIG. 14).

Expression vector pMJ09 was constructed by PCR amplifying the *Trichoderma reesei* Cel7A cellobiohydrolase Igene (cbh1) terminator from *Trichoderma reesei* RutC30 genomic DNA using primers 993843 (antisense) and 99344 (sense) shown below. The antisense primer was engineered to have a Pac I and a Spe I sites at the 5'-end and a Pvu I site at the 5'-end of the sense primer.

```
Primer 993844 (sense):
                                 (SEQ ID NO: 40)
5'-CGATCGTCTCCCTATGGGTCATTACC-3'

Primer 993843 (antisense):
                                 (SEQ ID NO: 41)
5'-ACTAGTTAATTAAGCTCCGTGGCGAAAG-3'
```

The amplification reactions (50 µl) were composed of 1× ThermoPol Reaction Buffer, 0.3 mM dNTPs, 100 ng of *Trichoderma reesei* RutC30 genomic DNA (which was extracted using a QIAGEN DNeasy Plant Maxi Kit), 0.3 µM primer 993844, 0.3 µM primer 993843, and 2 units of Vent polymerase The reactions were incubated in an Eppendorf Mastercycler 5333 programmed as follows: 30 cycles each for 30 seconds at 94° C., 30 seconds at 55° C., and 60 seconds at 72° C. (15 minute final extension).

The reaction products were isolated on a 1.0% agarose gel using TAE buffer where a 473 bp product band was excised from the gel and purified using a QIAGEN QIAquick Gel Extraction Kit according to the manufacturer's instructions.

Figure 15:
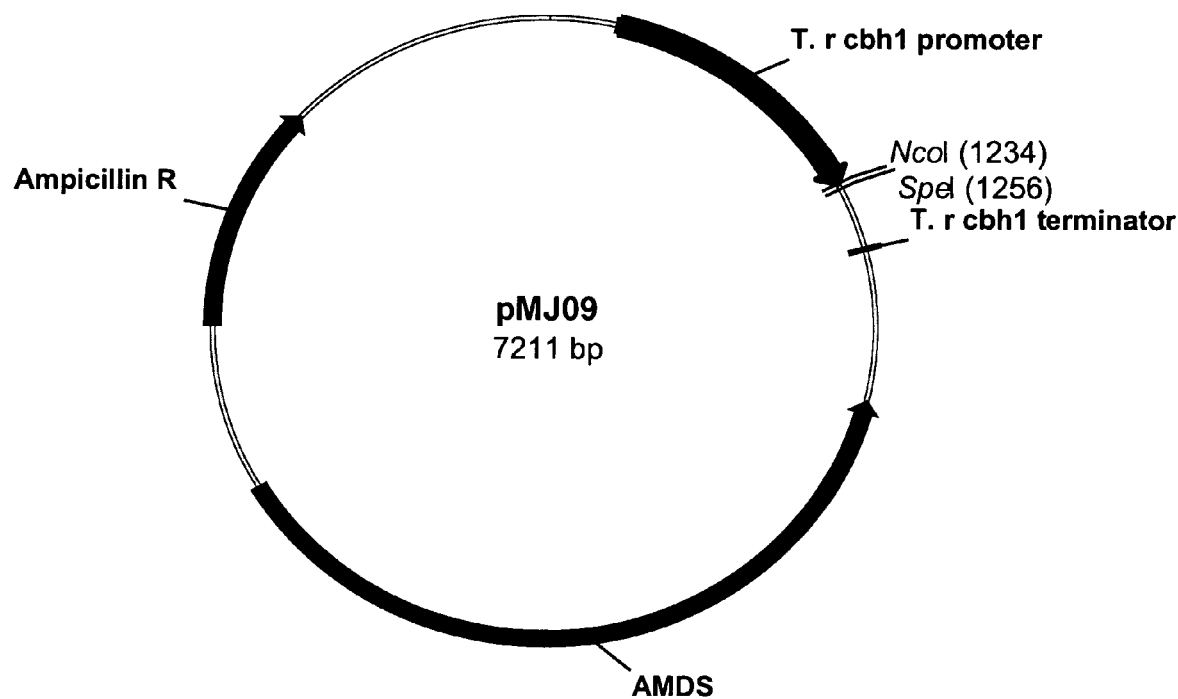
FIG. 15 shows a restriction map of pMJ09.

The resulting PCR fragment was digested with Pvu I and Spe I and ligated into pMJ06, digested with Pac I and Spe I using a Rapid Ligation Kit, to generate pMJ09 (FIG. 15).

Example 15

Cloning, Characterization, and Expression of the Family 7 *Trichoderma reesei* Endoglucanse (eg1) Gene Two synthetic oligonucleotide primers shown below were designed to PCR amplify a *Trichoderma reesei* gene encoding a putative Family 7 endoglucanase from cDNA prepared from *Trichoderma reesei* RutC30 by using a Cells-to-cDNA Kit (Ambion, Austin, Tex.) according to the manufacturer's instructions.

```
Forward primer:
                                 (SEQ ID NO: 42)
5'-CTTCACCATGGCGCCCTCAGTTACACTGC-3'

Reverse primer:
                                 (SEQ ID NO: 43)
5'-GCCGTTAATTAAGGCAAGTCAACGCTCTAAAGG-3'
```

Fifty picomoles of each of the primers above were used in a PCR reaction containing 100 ng of *Trichoderma reesei* cDNA, 1×Pwo Amplification Buffer (Roche, Indianapolis, Ind.), 4 µl of 10 mM blend of dATP, dTTP, dGTP, and dCTP, and 2.5 units of Pwo DNA Polymerase (Roche, Indianapolis, Ind.) in a final volume of 50 µl. The amplification conditions were 1 cycle at 94° C. for 2 minutes; 35 cycles each at 94° C. for 15 seconds, 55° C. for 30 seconds, and 72° C. for 2 minutes. The heat block then went to a 4° C. soak cycle.

The reaction products were isolated on a 1.0% agarose gel using TAE buffer where a 1.5 kb product band was excised from the gel and purified using a QIAquick Gel Extraction Kit (QIAGEN Inc., Chatsworth, Calif.) according to the manufacturer's instructions.

Figure 16:
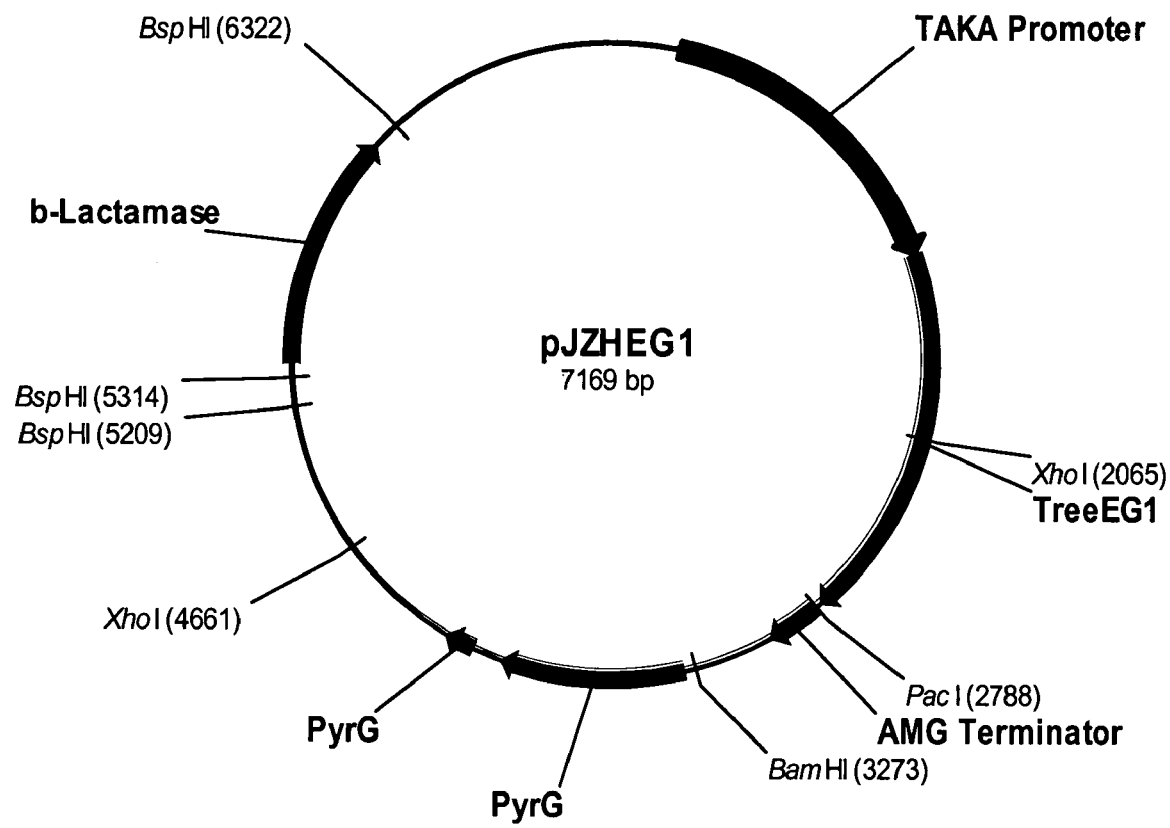
FIG. 16 shows a restriction map of pJZHEG1.

The fragment was then cloned into pAlLo2. Both fragment and vector were digested with Nco I and Pac I, and then were purified by gel electrophoresis and Qiaquick gel purification. The digested gene fragment and vector were ligated together in a reaction resulting in the expression plasmid pJZHEG1 (FIG. 16) in which transcription of the eg1 gene was under the control of the TAKA promoter. The ligation reaction (40 µl) was composed of 1× ligation Buffer (Roche, Indianapolis, Ind.), 1×DNA dilution Buffer (Roche, Indianapolis, Ind.), 5.0 units of T4 DNA ligase enzyme (Roche, Indianapolis, Ind.), 100 ng of pAlLo2 digested with Nco I and Pac I, and 100 ng of the *Trichoderma reesei* eg1 PCR product. The reaction was incubated at room temperature for 30 minutes. One µl of the reaction was used to transform *E. coli* XL10 Solopac Gold cells (Stratagene, La Jolla, Calif.). An *E. coli* transformant containing the pJZHEG1 plasmid was detected by restriction digestion and plasmid DNA was prepared using a BioRobot 9600 (QIAGEN Inc., Chatsworth, Calif.).

DNA sequencing of the *Trichoderma reesei* eg1 from pJZHEG1 was performed with a Perkin-Elmer Applied Biosystems Model 377 XL Automated DNA Sequencer (Perkin-Elmer/Applied Biosystems, Inc., Foster City, Calif.) using dye-terminator chemistry according to the manufacturer's instructions. Nucleotide sequence data were scrutinized for quality and all sequences were compared to each other with assistance of PHRED/PHRAP software (University of Washington, Seattle, Wash.). A comparative alignment of eg1 sequence was determined using the Clustal W method (Higgins, 1989, *CABIOS* 5: 151-153) with the Vector NTI software (InfoMax, San Francisco, Calif.). The alignment indicated that the deduced amino acid sequence of the *Trichoderma reesei* eg1 gene is identical to the deduced amino acid sequence of the *Trichoderma reesei* EG1 (accession number AAA34212, Penttila et al., 1986, *Gene* 45: 253-263).

*Aspergillus oryzae* JaL250 protoplasts were prepared according to the method of Christensen et al., 1988, supra. Five μg of pJZHEG1 (as well as pAlLo2 as a vector control) was used to transform *Aspergillus oryzae* JaL250.

The transformation of *Aspergillus oryzae* JaL250 with pJZHEG1 yielded about 40 transformants per μg DNA. Twenty transformants were isolated to individual PDA plates. Each plate was washed with 5 ml of 0.01% Tween 20 and inoculated separately into 25 ml of MDU2BP medium in 125 ml glass shake flasks and incubated at 34° C., 250 rpm. Five days after incubation, 0.5 μl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that one of the transformants (designated transformant 9) had a major band of approximately 58 kDa.

A confluent plate of transformant 9 (grown on PDA) was washed with 10 ml of 0.01% Tween 20 and inoculated into a 2 liter Fernbach containing 400 ml of MDU2BP medium to generate broth for characterization of the enzyme. The flask was harvested on day 5 and filtered using a 0.22 μm GP Express plus Membrane (Millipore, Bedford, Mass.). Endoglucanase activity was determined as described herein.

Prior to hydrolysis experiments, *Trichoderma reesei* endoglucanase 1 (recombinantly produced in *Aspergillus oryzae*) was desalted and exchanged into 50 mM sodium acetate pH 5.0 buffer using a Centricon Plus-20 centrifugal filter with Biomax-5 membrane (5000 NMWL; Millipore, Bedford, Mass.).

Example 16

Preparation of Pretreated Corn Stover

Corn stover was pretreated at the U.S. Department of Energy National Renewable Energy Laboratory (NREL) using dilute sulfuric acid. The following conditions were used for the pretreatment: 1.4 wt % sulfuric acid at 165° C. and 107 psi for 8 minutes. The water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. Prior to enzymatic hydrolysis, the PCS was washed with a large volume of DDI water on a glass filter. The dry weight of the water-washed PCS was found to be 24.54%.

Example 17

Preparation of Lignacious Residue

Lignacious residue was prepared by incubating 5% PCS with cell-free filtered fermentation broth of *Aspergillus oryzae* beta-glucosidase (recombinantly produced in *Trichoderma reesei*) at 10 mg per g of PCS under constant stirring in a 900-ml reaction for 6 days at pH 5.0, 50° C. After hydrolysis, liquid hydrolysate was removed by centrifugation at 3836×g for 10 minutes, and the solid lignin-enriched residue was washed four times with 250 ml of deionized water. The residue was then incubated for 5 days in 250 ml of deionized water under constant stirring at 65° C. to inactivate any remaining adsorbed enzyme. After additional washing with deionized water followed by centrifugation as described above, approximately 100 ml of a 15% suspension of lignaceous residue in deionized water was obtained.

Example 18

Sugar Analysis

Twenty μl aliquots were removed from PCS hydrolysis reactions at specified time points using an 8-channel pipettor, and added to 180 μl of alkaline mixture (102 mM $Na_2CO_3$ plus 58 mM $NaHCO_3$) in a MultiScreen HV 96-well filtration plate (Millipore, Bedford, Mass.) to terminate the reaction. The samples were vacuum-filtered into another flat-bottomed microplate to remove the PCS residue. After appropriate dilution, the filtrates were analyzed for reducing sugar (RS) using p-hydroxybenzoic acid hydrazide (PHBAH) assay (Lever M., 1973, Colorimetric and fluorometric carbohydrate determination with p-hydroxybenzoic acid hydrazide, *Biochemical Medicine* 7: 274-281) in a microplate format.

A 90-μl aliquot of the diluted sample was placed into each well of a 96-well conical-bottomed microplate (Corning Inc., Acton, Mass., Costar, clear polycarbonate). The assay was started by adding 60 μl of 1.25% PHBAH in 2% sodium hydroxide to each well. The uncovered plate was heated on a custom-made heating block for 10 minutes at 95° C. After the microplate was cooled to room temperature, 35 μl of deionized water was added to each well. A 100-μl aliquot was removed from each well and transferred to a flat-bottomed 96-well plate (Corning Inc., Acton, Mass., Costar, medium binding polystyrene). The absorbance at 410 nm ($A_{410}$) was measured using a SpectraMAX Microplate Reader (Molecular Devices, Sunnyvale, Calif.). The $A_{410}$ value was translated into glucose equivalents using a standard curve.

The standard curve was obtained with six glucose standards (0.005, 0.010, 0.025, 0.050, 0.075, and 0.100 mg/ml), which were treated similarly to the samples. Glucose standards were prepared by diluting 10 mg/ml stock glucose solution with deionized water.

The degree of cellulose conversion to reducing sugar (hydrolysis yield, %) was calculated using the following equation:

$$RS\ Yield_{(\%)} = RS_{(mg/ml)} * 100 * 162 / (Cellulose_{(mg/ml)} * 180)$$

$$= RS_{(mg/ml)} * 100 / (Cellulose_{(mg/ml)} * 1.111)$$

In this equation, RS is the concentration of reducing sugar in solution measured in glucose equivalents (mg/ml), and the factor 1.111 reflects the weight gain in converting cellulose to glucose.

Example 19

Enhanced Production of Sugars from PCS Using Softanol® 90 Non-Ionic Surfactant at 50° C.

Hydrolysis of PCS (5% w/v on a dry weight basis) by Celluclast 1.5 L (2.5, 5, 10, and 20 mg/g PCS) supplemented with desalted and buffer exchanged *Aspergillus oryzae* beta-glucosidase (recombinantly produced in *Aspergillus oryzae*) at 0.6 mg per g of PCS was carried out in 50 mM sodium acetate pH 5.0 in a 10-ml volume with intermittent stirring at 50° C. Samples were taken at different time-points and analyzed for reducing sugars as described in Example 18. Reactions containing Celluclast 1.5 L at 2.5 and 5 mg per g of PCS were supplemented with 0.5% v/v Softanol® 90 (0.1 ml/g PCS), and the results were compared with control reactions without the surfactant.

Figure 17:
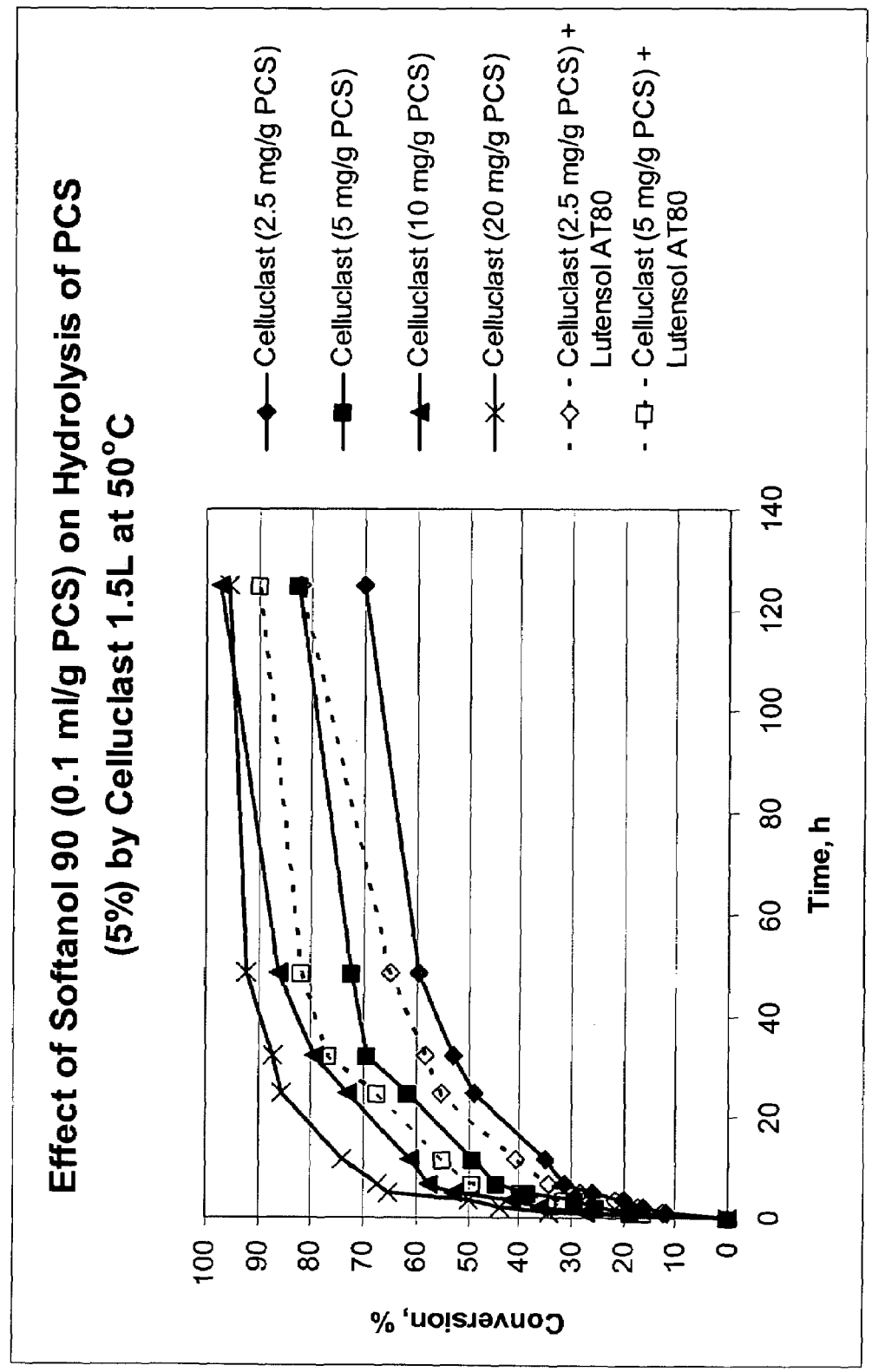
FIG. 17 shows the effect of Softanol® 90 (0.1 ml/g PCS) on hydrolysis of PCS (5%) by Celluclast 1.5 L at 50° C.

The results as shown in Table 2 and FIG. 17 demonstrated that addition of Softanols 90 increased the hydrolysis yield of reducing sugars after incubation for 125 hours from 70% to 86% for reactions with 2.5 mg Celluclast/g PCS (23% improvement), and from 83% to 94% for reactions with 5 mg Celluclast/g PCS (14% improvement). Using Softanol® 90, it was possible to reduce the enzyme loading by a factor of two compared to reactions without the surfactant, while achieving the same 125 hour hydrolysis yield.

TABLE 2

Effect of Softanol ® 90 and Lutensol ® AT80 (0.1 ml/g PCS) on Hydrolysis of PCS (5%) by Celluclast 1.5 L at 50° C.

| Reaction | Surfactant, % | Surfactant, ml/g PCS | 125-hour Conversion, % | Improvement at 125 h, % |
|---|---|---|---|---|
| Celluclast (2.5 mg/g PCS) | 0.0 | 0.0 | 70 | NA |
| Celluclast (5 mg/g PCS) | 0.0 | 0.0 | 83 | NA |
| Celluclast (10 mg/g PCS) | 0.0 | 0.0 | 97 | NA |
| Celluclast (20 mg/g PCS) | 0.0 | 0.0 | 96 | NA |
| Celluclast (2.5 mg/g PCS) + Softanol ® 90 (0.1 ml/g PCS) | 0.5 | 0.1 | 86 | 23 |
| Celluclast (5 mg/g PCS) + Softanol ® 90 (0.1 ml/g PCS) | 0.5 | 0.1 | 94 | 14 |
| Celluclast (2.5 mg/g PCS) + Lutensol ® AT80 (0.1 ml/g PCS) | 0.5 | 0.1 | 82 | 17 |
| Celluclast (5 mg/g PCS) + Lutensol ® AT80 (0.1 ml/g PCS) | 0.5 | 0.1 | 90 | 9 |

Example 20

Enhanced Production of Sugars from PCS using Lutensol® AT80 Non-Ionic Surfactant at 50° C.

Example 19 was repeated, except that Lutensol® AT80 was used at 0.1 ml/g PCS (0.5% v/v).

Figure 18:
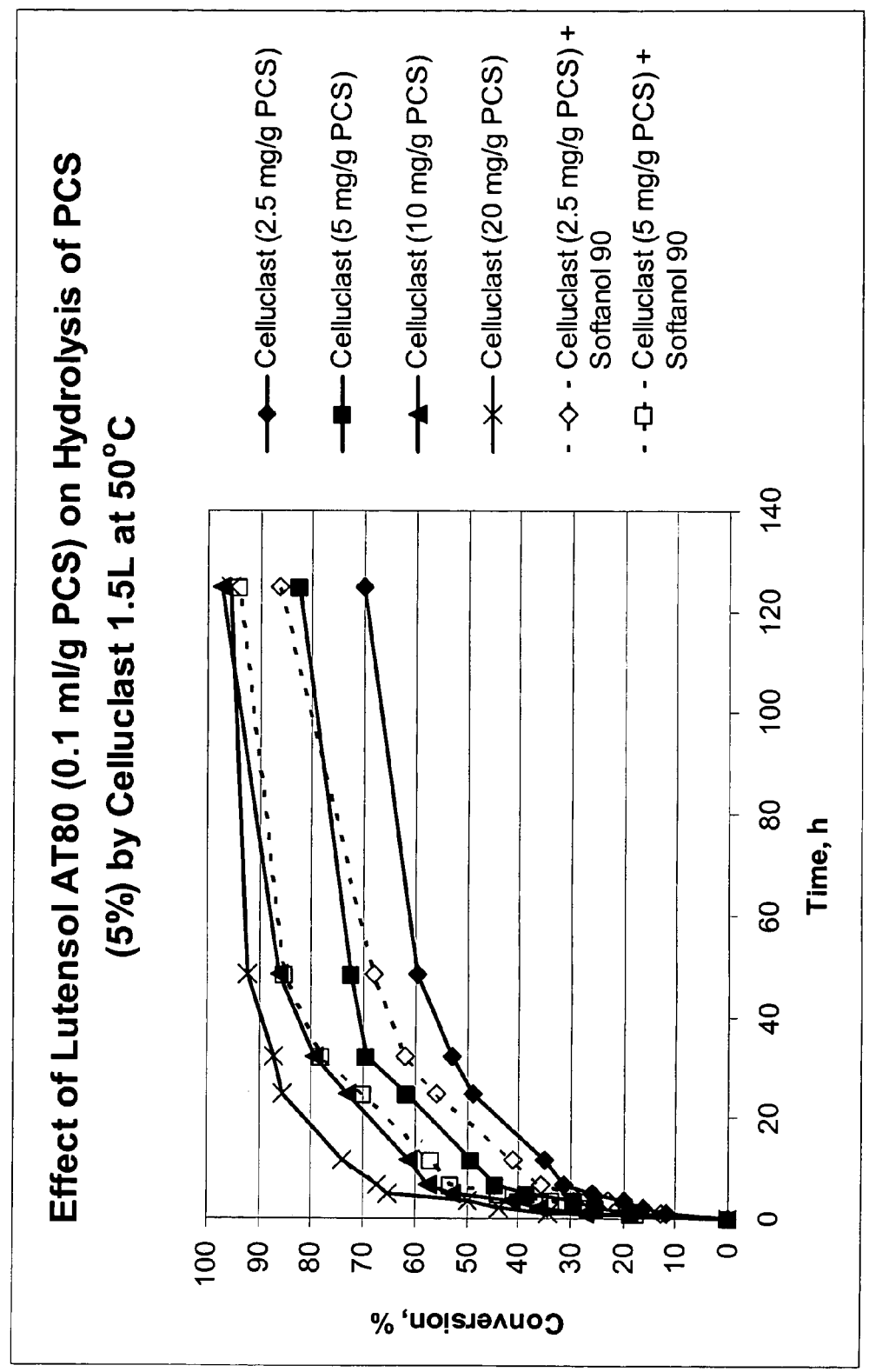
FIG. 18 shows the effect of Lutensol® AT80 (0.1 ml/g PCS) on hydrolysis of PCS (5%) by Celluclast 1.5 L at 50° C.

The results as shown in Table 2 and FIG. 18 demonstrated that addition of Lutensol® AT80 increased the 125-hour hydrolysis yield of reducing sugars from 70% to 82% for reactions with 2.5 mg Celluclast/g PCS (17% improvement), and from 83% to 90% for reactions with 5 mg Celluclast/g PCS (9% improvement).

Example 21

Enhanced Production of Sugars from PCS using Softanol® 90 at 50° C. and 55° C.

Example 19 was repeated, except that additional loading of Celluclast 1.5 L was included (1.25 mg/g PCS), Softanol® 90 was used at 0.2 ml/g PCS (1.0% v/v), and the hydrolysis was run at two temperatures, 50° C. and 55° C. Softanol® 90 was added to the reactions containing 1.25, 2.5, and 5 mg of Celluclast 1.5 L per g of PCS, and the results were compared with control reactions without the surfactant. The results are shown in Table 3 and FIGS. 19 and 20.

Figure 19:
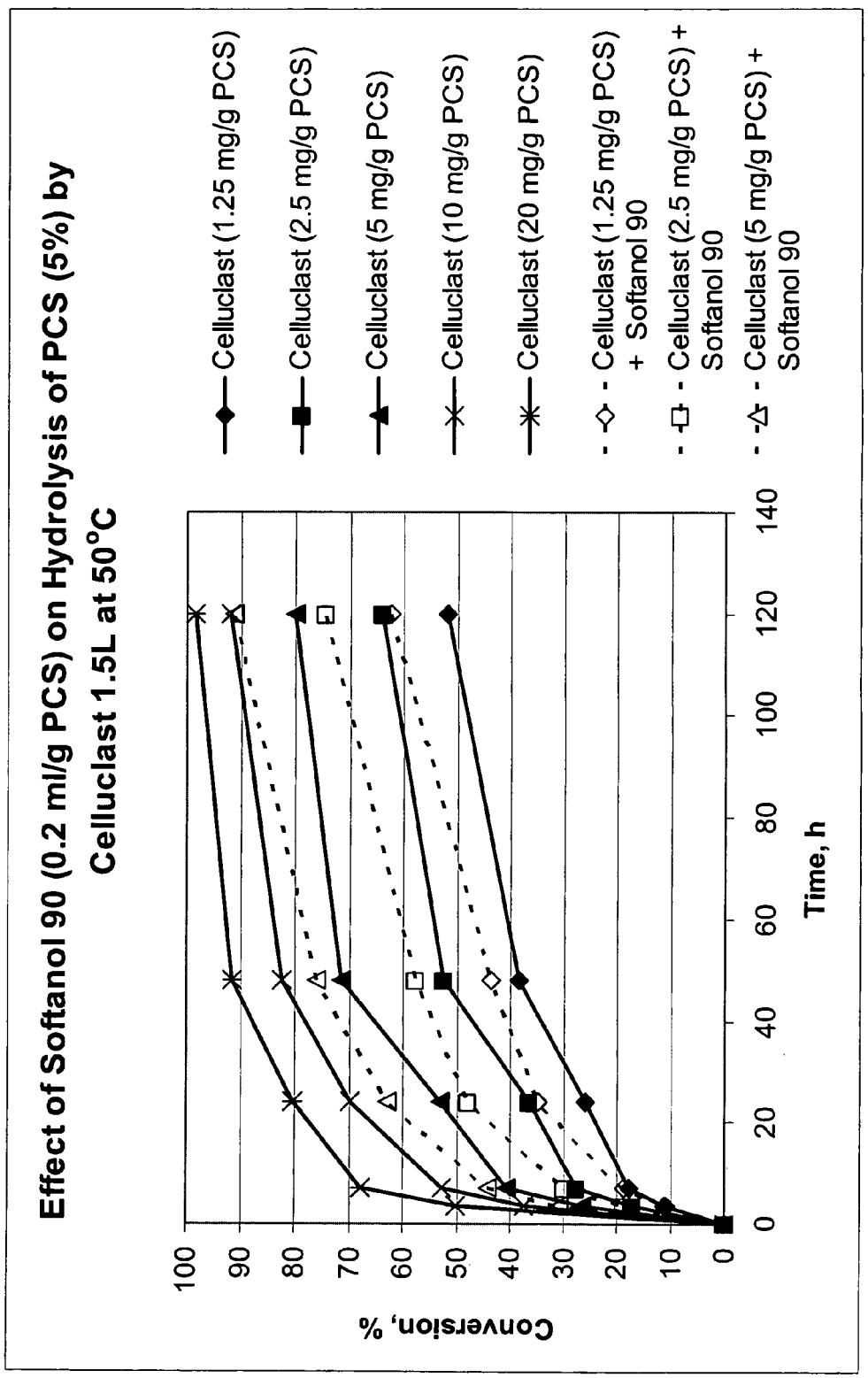
FIG. 19 shows the effect of Softanol® 90 (0.2 ml/g PCS) on hydrolysis of PCS (5%) by Celluclast 1.5 L at 50° C.

At 50° C., addition of Softanol® 90 increased the 120-hour hydrolysis yield of reducing sugars by 14-20% compared to reactions without the surfactant. FIG. 19 shows that in the presence of Softanol® 90, the enzyme loading could be reduced by a factor of two compared to reactions without the surfactant while maintaining the same hydrolysis yield.

Figure 20:
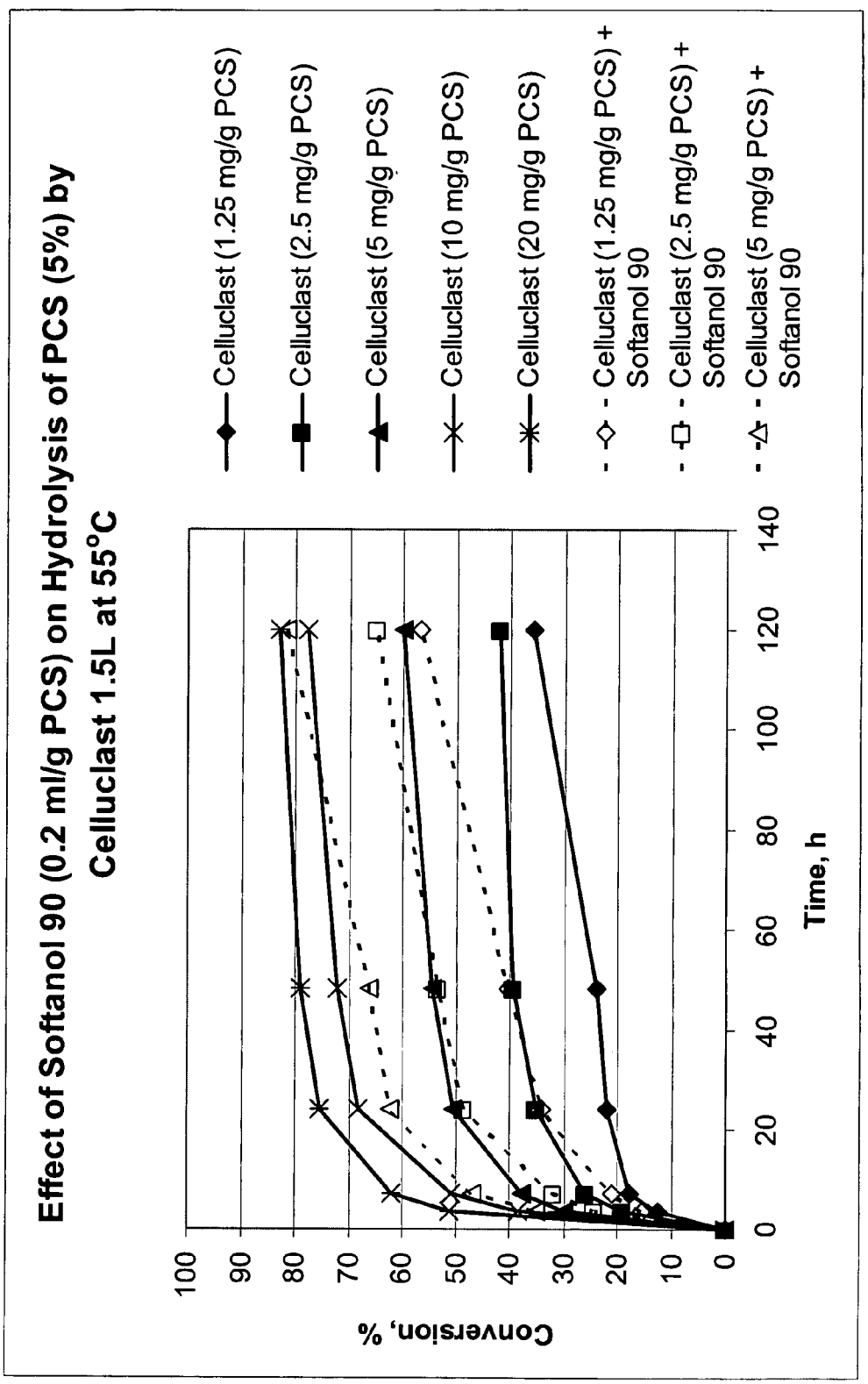
FIG. 20 shows the effect of Softanol® 90 (0.2 ml/g PCS) on hydrolysis of PCS (5%) by Celluclast 1.5 L at 55° C.

At 55° C., Softanol® 90 showed more significant improvement than at 50° C. Addition of Softanol® 90 at 55° C. increased the 120-hour hydrolysis yields of reducing sugars by 36-59% compared to reactions without the surfactant. FIG. 20 shows that in the presence of Softanol® 90, four times lower enzyme loadings compared to reactions without the surfactant could achieve comparable hydrolysis yields of reducing sugars.

TABLE 3

Effect of Softanol ® 90 (0.2 ml/g PCS) on Hydrolysis of PCS (5%) by Celluclast 1.5 L at 50° C. and 55° C.

| T° C. | Reaction | Softanol ® 90, ml/g PCS | 120-hour Conversion % | Improvement at 120 h, % |
|---|---|---|---|---|
| 50 | Celluclast (1.25 mg/g PCS) | 0.0 | 52 | NA |
| | Celluclast (2.5 mg/g PCS) | 0.0 | 64 | NA |
| | Celluclast (5 mg/g PCS) | 0.0 | 80 | NA |
| | Celluclast (10 mg/g PCS) | 0.0 | 92 | NA |
| | Celluclast (20 mg/g PCS) | 0.0 | 98 | NA |
| | Celluclast (1.25 mg/g PCS) + Softanol ® 90 | 0.2 | 62 | 20 |
| | Celluclast (2.5 mg/g PCS) + Softanol ® 90 | 0.2 | 75 | 17 |
| | Celluclast (5 mg/g PCS) + Softanol ® 90 | 0.2 | 91 | 14 |

TABLE 3-continued

Effect of Softanol ® 90 (0.2 ml/g PCS) on Hydrolysis of PCS (5%) by Celluclast 1.5 L at 50° C. and 55° C.

| T° C. | Reaction | Softanol ® 90, ml/g PCS | 120-hour Conversion % | Improvement at 120 h, % |
|---|---|---|---|---|
| 55 | Celluclast (1.25 mg/g PCS) | 0.0 | 36 | NA |
| | Celluclast (2.5 mg/g PCS) | 0.0 | 42 | NA |
| | Celluclast (5 mg/g PCS) | 0.0 | 60 | NA |
| | Celluclast (10 mg/g PCS) | 0.0 | 78 | NA |
| | Celluclast (20 mg/g PCS) | 0.0 | 83 | NA |
| | Celluclast (1.25 mg/g PCS) + Softanol ® 90 | 0.2 | 57 | 59 |
| | Celluclast (2.5 mg/g PCS) + Softanol ® 90 | 0.2 | 65 | 54 |
| | Celluclast (5 mg/g PCS) + Softanol ® 90 | 0.2 | 82 | 36 |

Example 22

Softanol® 90 Dose Dependence for Hydrolysis of PCS by Celluclast 1.5 L at 50° C.

Example 19 was repeated, except that Softanol® 90 was added at 0.05, 0.1, 0.2, 0.3, and 0.4 ml/g PCS to reactions with 2 mg of Celluclast 1.5 L per g of PCS, and desalted and buffer exchanged *Aspergillus oryzae* beta-glucosidase (recombinantly produced in *Aspergillus oryzae*) was added at 3% of Celluclast loading (0.6 mg/g PCS).

Figure 21:
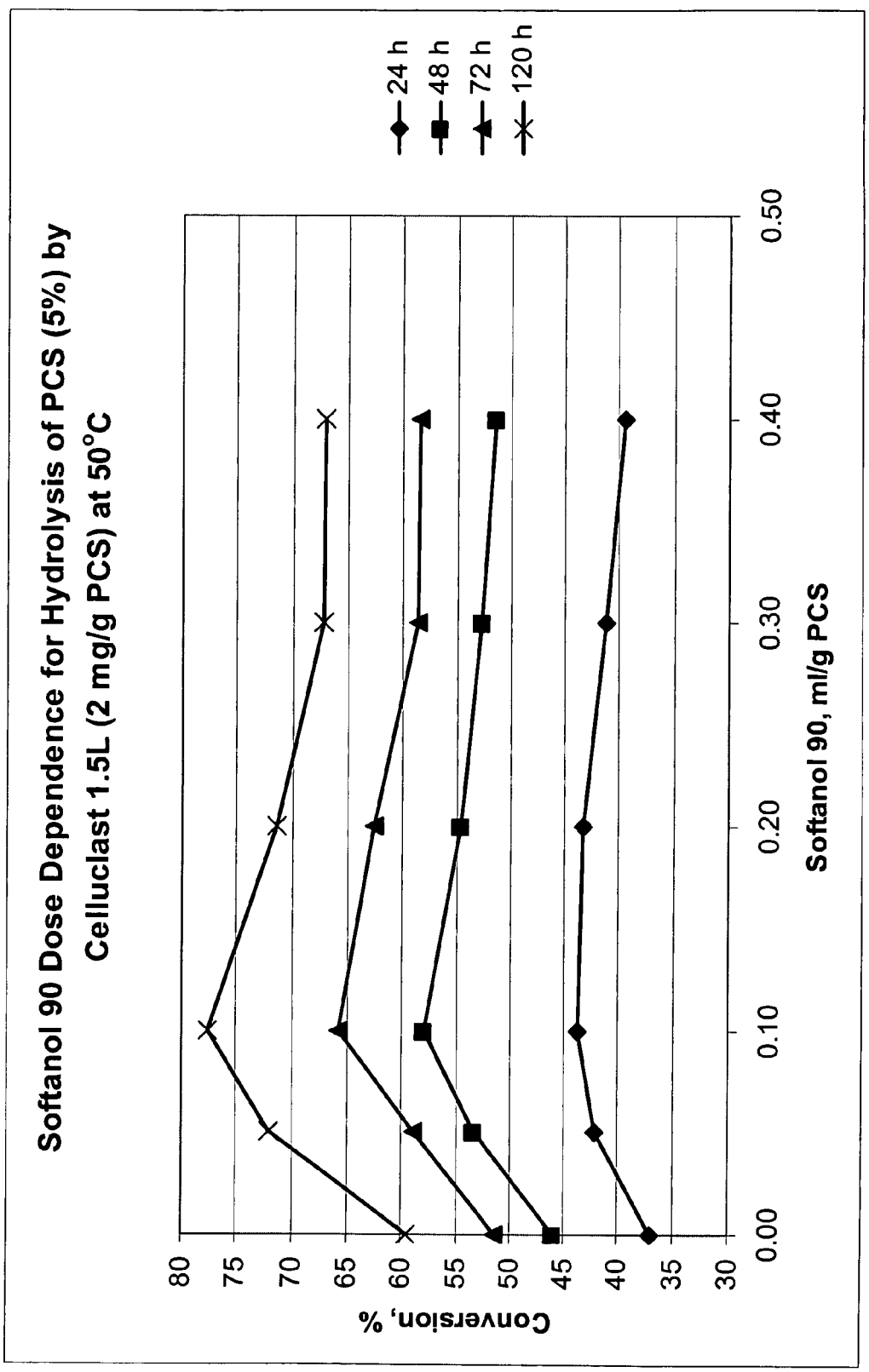
FIG. 21 shows the Softanol® 90 dose dependence for hydrolysis of PCS (5%) by Celluclast 1.5 L (2 mg/g PCS) at 50° C.

The results are shown in Table 4 and FIG. 21. The optimal loading of Softanol® 90 was found to be 0.1 ml per g of PCS, which corresponded to a Softanol® 90 concentration of 0.5% v/v.

TABLE 4

Softanol ® 90 Dose Dependence for Hydrolysis of PCS (5%) by Celluclast 1.5 L (2 mg/g PCS) at 50° C.

| Reaction | Softanol ® 90, % | Softanol ® 90, ml/g PCS | 120-hour Conversion, % | Improvement at 120 h, % |
|---|---|---|---|---|
| Celluclast (2 mg/g PCS) | 0.0 | 0.0 | 60 | NA |
| Celluclast (2 mg/g PCS) + Softanol ® 90 | 0.25 | 0.05 | 72 | 21 |
| | 0.5 | 0.1 | 78 | 30 |
| | 1.0 | 0.2 | 72 | 20 |
| | 1.5 | 0.3 | 67 | 13 |
| | 2.0 | 0.4 | 67 | 13 |

Example 23

Enhanced Production of Sugars from PCS Using Different Softanol® Products at 50° C.

Example 22 was repeated, except that different Softanol® products, Softanol® 50, 90, 120, or 200, with increasing degree of ethoxylation and increasing hydrophilic/lipophilic balance (HLB) values were added at 0.2 ml per g of PCS (1.0% v/v) to reactions with 2 mg of Celluclast 1.5 L per g of PCS.

Figure 22:
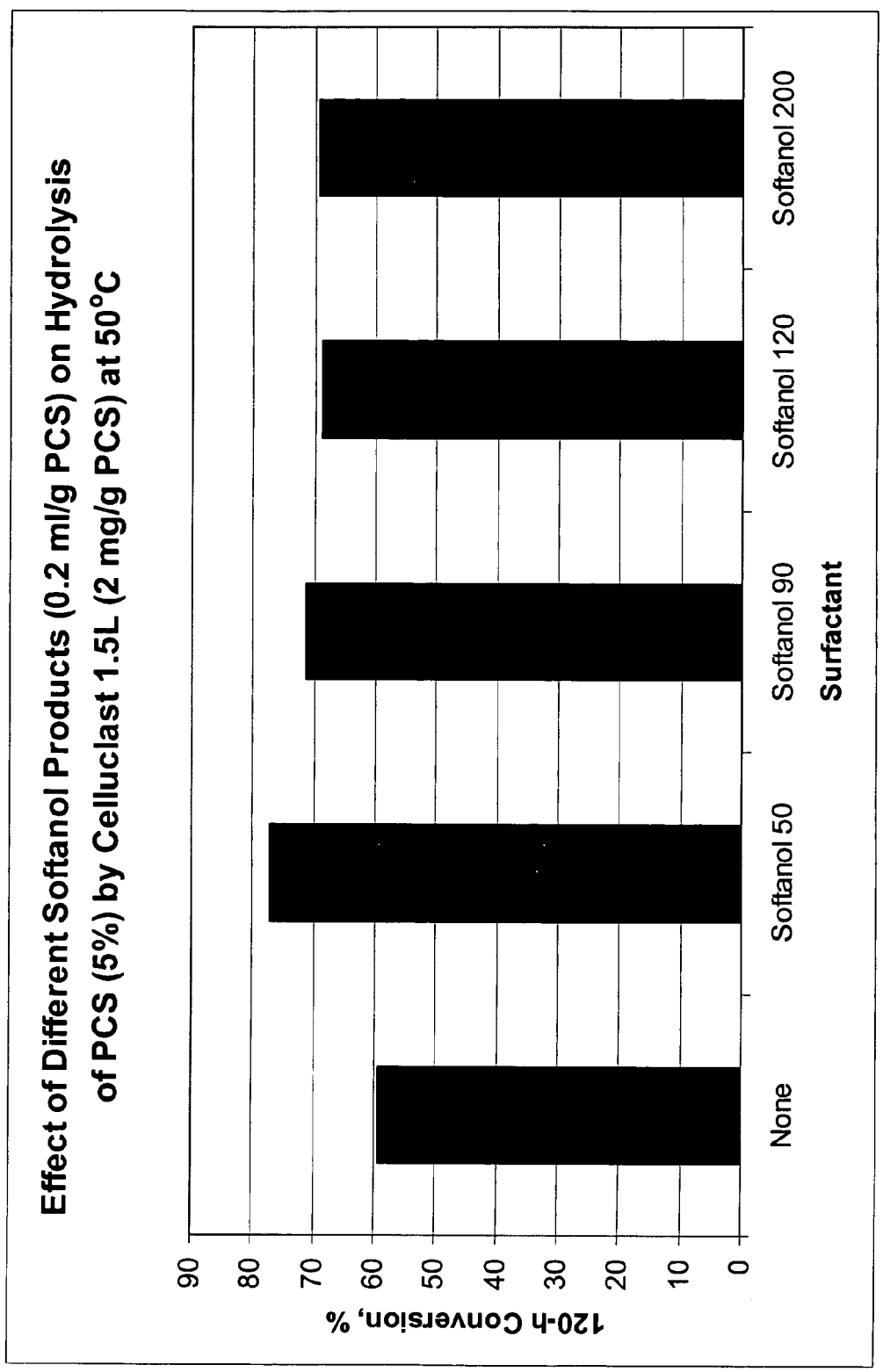
FIG. 22 shows the effect of different Softanol® products on hydrolysis of PCS (5%) by Celluclast 1.5 L (2 mg/g PCS) at 50° C.

FIG. 22 shows that all Softanol® products performed similarly, increasing the final hydrolysis yield of reducing sugars by 17-30% compared to reactions without surfactants.

Example 24

Effect of Softanol® 90 on Hydrolysis of PCS by Celluclast 1.5 L and *Trichoderma reesei* Fermentation Broth Expressing *Aspergillus oryzae* Beta-Glucosidase at 50° C.

Example 22 was repeated, except that Softanol® 90 was added at 0.2 ml per g of PCS (1.0% v/v) to reactions with Celluclast 1.5 L (2 mg/g PCS) supplemented with desalted and buffer exchanged *Aspergillus oryzae* beta-glucosidase (recombinantly produced in *Aspergillus oryzae*) at 0.06 mg per g of PCS or to reactions with cell-free filtered fermentation broth of *Aspergillus oryzae* beta-glucosidase (recombinantly produced in *Trichoderma reesei*) at 2 mg per g of PCS.

Figure 23:
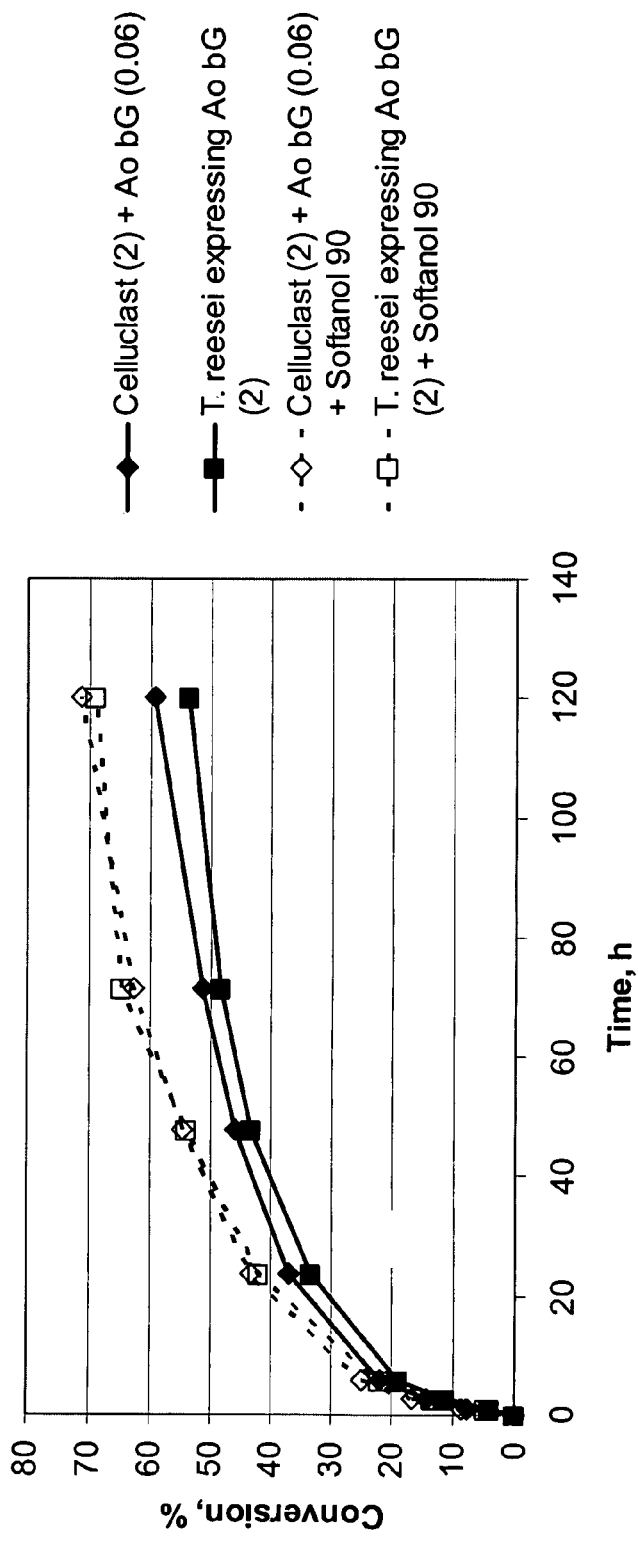
FIG. 23 shows the effect of Softanol□ 90 (0.2 ml/g PCS) on hydrolysis of PCS (5%) by Celluclast 1.5 L (2 mg/g PCS) supplemented with *Aspergillus oryzae* beta-glucosidase (0.06 mg/g PCS) and cell-free broth of *Trichoderma reesei* expressing *Aspergillus oryzae* beta-glucosidase (2 mg/g PCS) at 50° C.

Without Softanol® 90, both enzymes performed similarly. FIG. 23 shows that the addition of Softanol® 90 provided a comparable boosting effect for both enzymes.

Example 25

Enhancing Effect of Softanol® 90 on Hydrolysis of PCS by *Trichoderma reesei* CBHI at 40-65° C.

*Trichoderma reesei* cellobiohydrolase 1 (CBHI) was isolated and purified to homogeneity from Celluclast 1.5 L using methods described by Suurnäkki et al., 2000, *Cellulose* 7: 189-209.

Hydrolysis of ethanol-washed/milled PCS (1% w/v on a dry weight basis) by purified *Trichoderma reesei* CBHI (2, 5, and 10 mg/g PCS) was carried out in 50 mM sodium acetate pH 5.0 in a 0.5-ml volume with intermittent stirring at 40° C., 50° C., 55° C., 60° C., and 65° C. Samples were taken at different time-points and analyzed for reducing sugars as described in Example 18. Reactions containing *Trichoderma reesei* CBHI at 2 mg/g PCS were supplemented with 0.1% v/v Softanol® 90 (0.1 ml/g PCS), and the results were compared with control reactions run without the surfactant.

Figure 24:
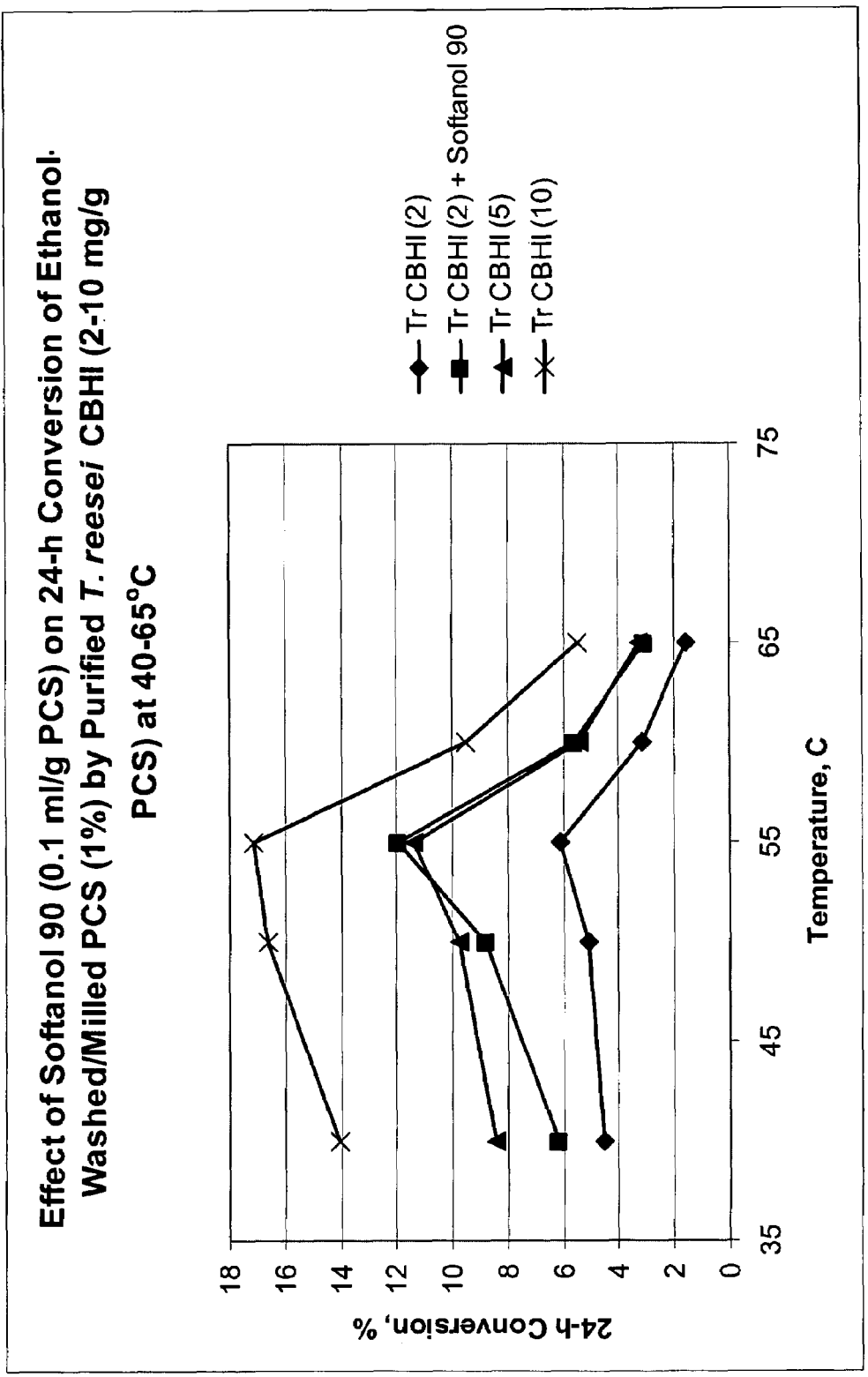
FIG. 24 shows the effect of Softanol® 90 (0.1 ml/g PCS) on 24 hour conversion of ethanol washed/milled PCS (1%) by purified *Trichoderma reesei* cellobiohydrolase 1 (2-10 mg/g PCS) at 40-65° C.

The results are shown in FIG. 24. At 55° C., addition of Softanol® 90 increased the 24-hour hydrolysis yield of reducing sugars by 94% compared to reaction without the surfactant (from 6.1% to 11.9%). Achieving a comparable hydrolysis yield in the absence of Softanol® 90 required 2.5 times higher enzyme loading (5 mg/g PCS).

Example 26

Enhancing Effect of Softanol® 90 on Hydrolysis of PCS by (*Trichoderma reesei* CBHI plus *Aspergillus fumigatus* Beta-Glucosidase) Mixture at 40-65° C.

Example 25 was repeated, except that *Trichoderma reesei* CBHI was supplemented with desalted and buffer exchanged *Aspergillus fumigatus* beta-glucosidase (recombinantly produced in *Aspergillus oryzae*) at 5% of the CBHI protein loading (0.1, 0.25, and 0.5 mg/g PCS).

Figure 25:
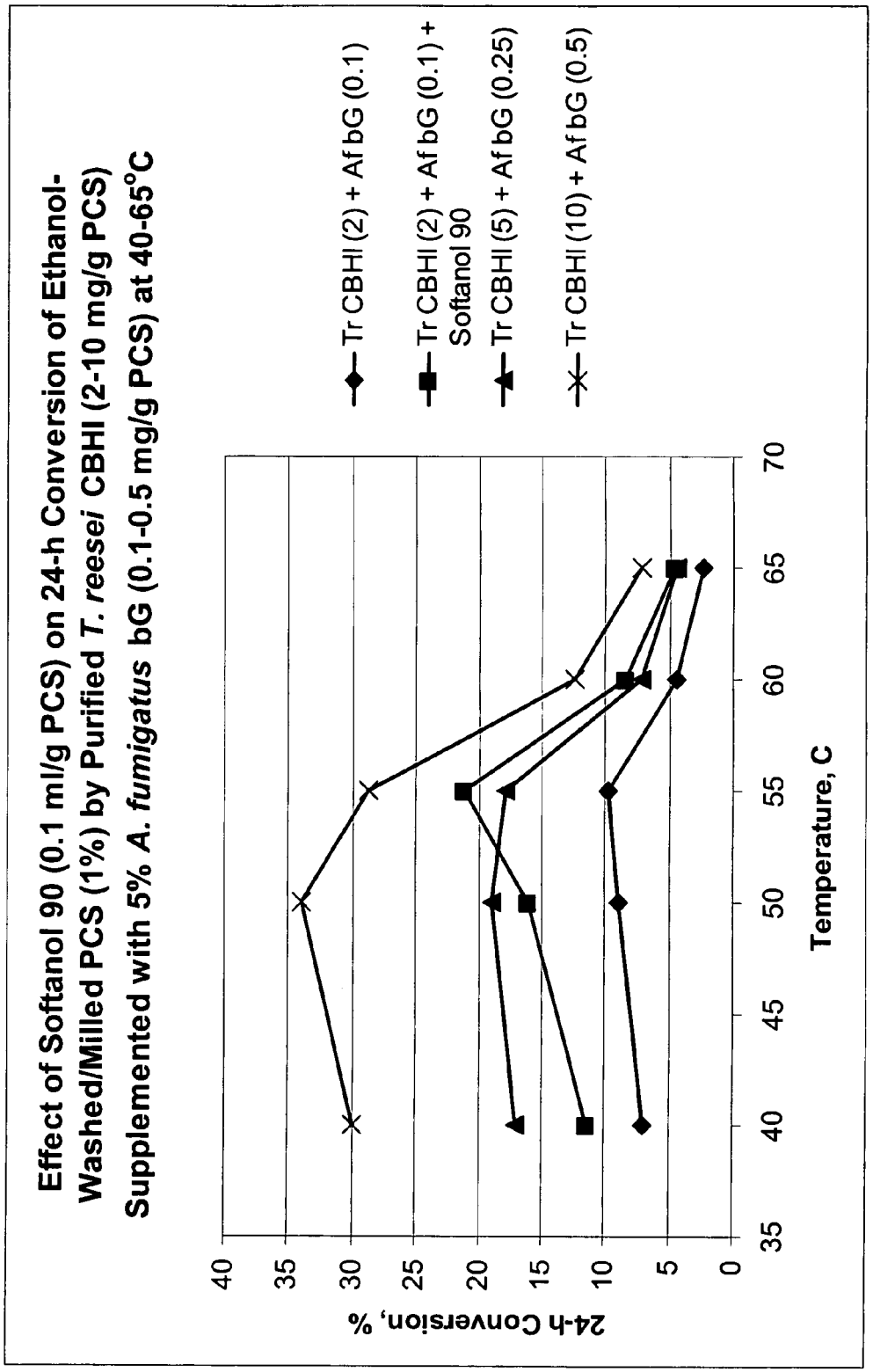
FIG. 25 shows the effect of Softanol® 90 (0.1 ml/g PCS) on 24 hour conversion of ethanol washed/milled PCS (1%) by purified *Trichoderma reesei* cellobiohydrolase 1 (2-10 mg/g PCS) supplemented with 5% *Aspergillus fumigatus* beta-glucosidase (0.1-0.5 mg/g PCS) at 40-65° C.

The results as shown in FIG. 25 demonstrated that at 55° C., addition of Softanol® 90 increased the 24-hour hydrolysis yield of reducing sugars by 115% compared to reaction without the surfactant (from 9.8% to 21.1%). Achieving comparable hydrolysis yield in the absence of Softanol® 90 required 2.5 times higher enzyme loading (5 mg/g PCS).

Example 27

Enhancing Effect of Softanol® 90 on Hydrolysis of PCS by *Trichoderma reesei* CBHI Plus *Trichoderma reesei* EGI Plus *Aspergillus fumigatus* Beta-Glucosidase Mixture at 40-65° C.

Example 25 was repeated, except that *Trichoderma reesei* CBHI (2, 5, 10, and 20 mg/g PCS) was supplemented with desalted and buffer exchanged *Trichoderma reesei* endoglucanase 1 (EGI; recombinantly produced in *Aspergillus oryzae*) at 20% of the CBHI protein loading (0.4, 1, 2, and 4 mg/g PCS) and desalted and buffer exchanged *Aspergillus fumigatus* beta-glucosidase (recombinantly produced in *Aspergillus oryzae*) at 5% of CBHI protein loading (0.1, 0.25, 0.5, and 1 mg/g PCS).

Figure 26:
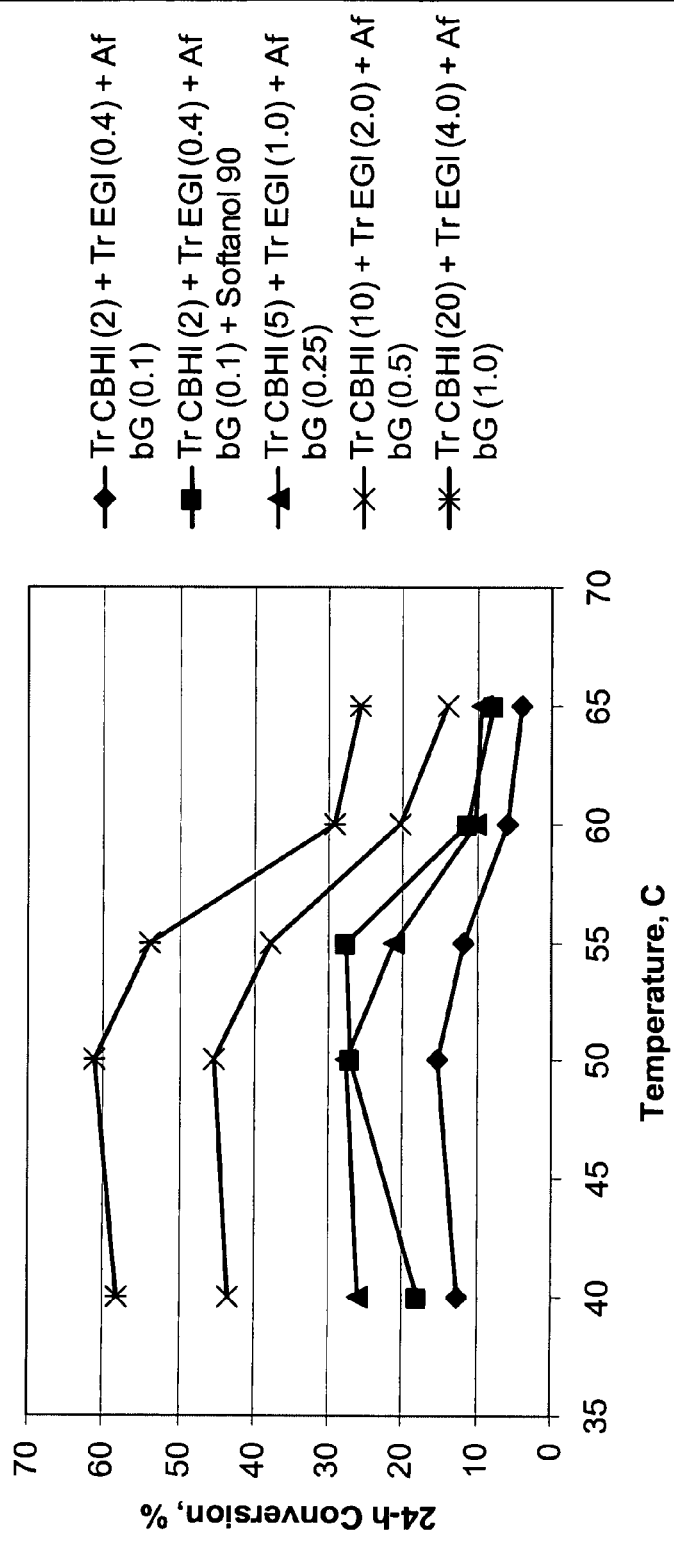
FIG. 26 shows the effect of Softanol® 90 (0.1 ml/g PCS) on 24 hour conversion of ethanol washed/milled PCS (1%) by purified *Trichoderma reesei* cellobiohydrolase 1 (2-20 mg/g PCS) supplemented with 20% *Trichoderma reesei* endoglucanase 1 (0.4-4 mg/g PCS) and 5% *Aspergillus fumigatus* beta-glucosidase (0.1-1 mg/g PCS) at 40-65° C.

The results are shown in FIG. 26. At 55° C., addition of Softanol® 90 increased the 24-hour hydrolysis yield of reducing sugars by 132% compared to reaction without the surfactant (from 11.9% to 27.6%). The resulting hydrolysis yield was higher than that obtained using 2.5 times higher enzyme loading (5 mg/g PCS) in the absence of Softanol® 90 (27.6% vs. 21.3%).

Example 28

Enhancing Effect of Softanol® 90 on Hydrolysis of PCS by *Trichoderma reesei* CBHI Plus Acidothermus Cellulolyticus E1cd Plus *Aspergillus fumigatus* Beta-Glucosidase Mixture at 40-65° C.

Example 27 was repeated, except that bacterial endoglucanase, *Acidothermus cellulolyticus* E1cd obtained from NREL, was used instead of fungal endoglucanase, *Trichoderma reesei* EGI. Acidothermus cellulolyticus E1cd was expressed from *Streptomyces lividans* TK24 acccording to U.S. Pat. No. 5,275,944. A truncated form of this enzyme was produced by subjecting the *Streptomyces lividans*-expressed enzyme to proteolytic treatment to remove the cellulose-binding domain (Baker et al., 1995, in *Enzymatic Degradation of Insoluble Polysaccharides*, Saddler, J. N. and Penner, M. H., eds., ACS Series 618, American Chemical Society, Washington, D.C., 113-141).

Figure 27:
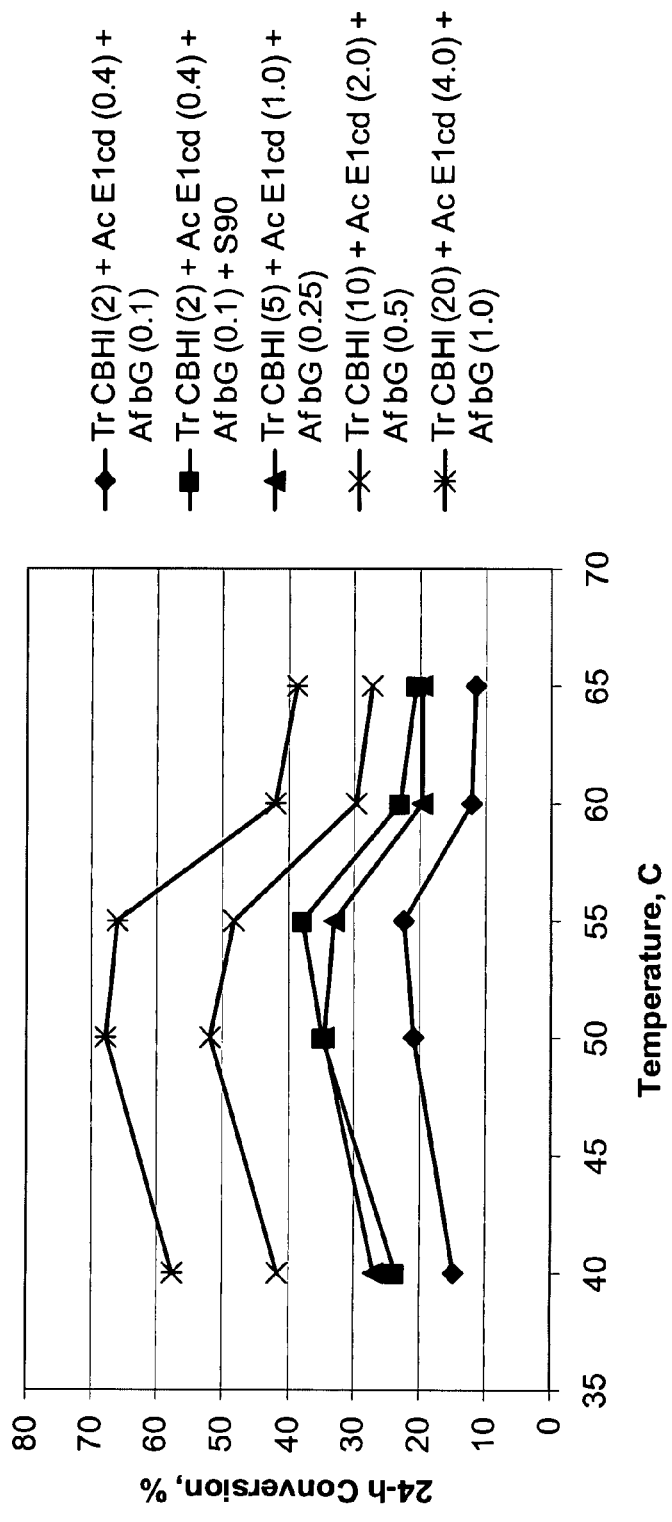
FIG. 27 shows the effect of Softanol® 90 (0.1 ml/g PCS) on 24 hour conversion of ethanol washed/milled PCS (1%) by purified *Trichoderma reesei* cellobiohydrolase 1 (2-20 mg/g PCS) supplemented with 20% *Acidothermus cellulolyticus* E1cd (0.4-4 mg/g PCS) and 5% *Aspergillus fumigatus* beta-glucosidase (0.1-1 mg/g PCS) at 40-65° C.

The results as shown in FIG. 27 demonstrated that at 55° C., addition of Softanol® 90 increased the 24-hour hydrolysis yield of reducing sugars by 70% compared to reaction without the surfactant (from 22.2% to 37.7%). The resulting hydrolysis yield was higher than that obtained using 2.5 times higher enzyme loading (5 mg/g PCS) in the absence of Softanol® 90 (37.7% vs. 33%).

Example 29

Effect of Softanol® 90 on Hydrolysis of Avicel by Celluclast 1.5 L at 50° C.

Hydrolysis of microcrystalline cellulose, Avicel PH101 (1% w/v on a dry weight basis, FMC Corporation, Philadelphia, Pa.) by Celluclast 1.5 L (1.25, 2.5, 5, 10, and 20 mg/g cellulose) supplemented with desalted and buffer exchanged *Aspergillus oryzae* beta-glucosidase (recombinantly produced in *Aspergillus oryzae*) at 0.6 mg per g of cellulose was carried out in 50 mM sodium acetate pH 5.0 in a 1-ml volume with intermittent stirring at 50° C. Samples were taken at different time-points and analyzed for reducing sugars as described in Example 18. Reactions containing Celluclast 1.5 L at 1.25, 2.5 and 5 mg/g cellulose were supplemented with Softanol® 90 at 0.05, 0.1 and 0.2 ml/g cellulose, and the results were compared with control reactions without the surfactant.

Figure 28:
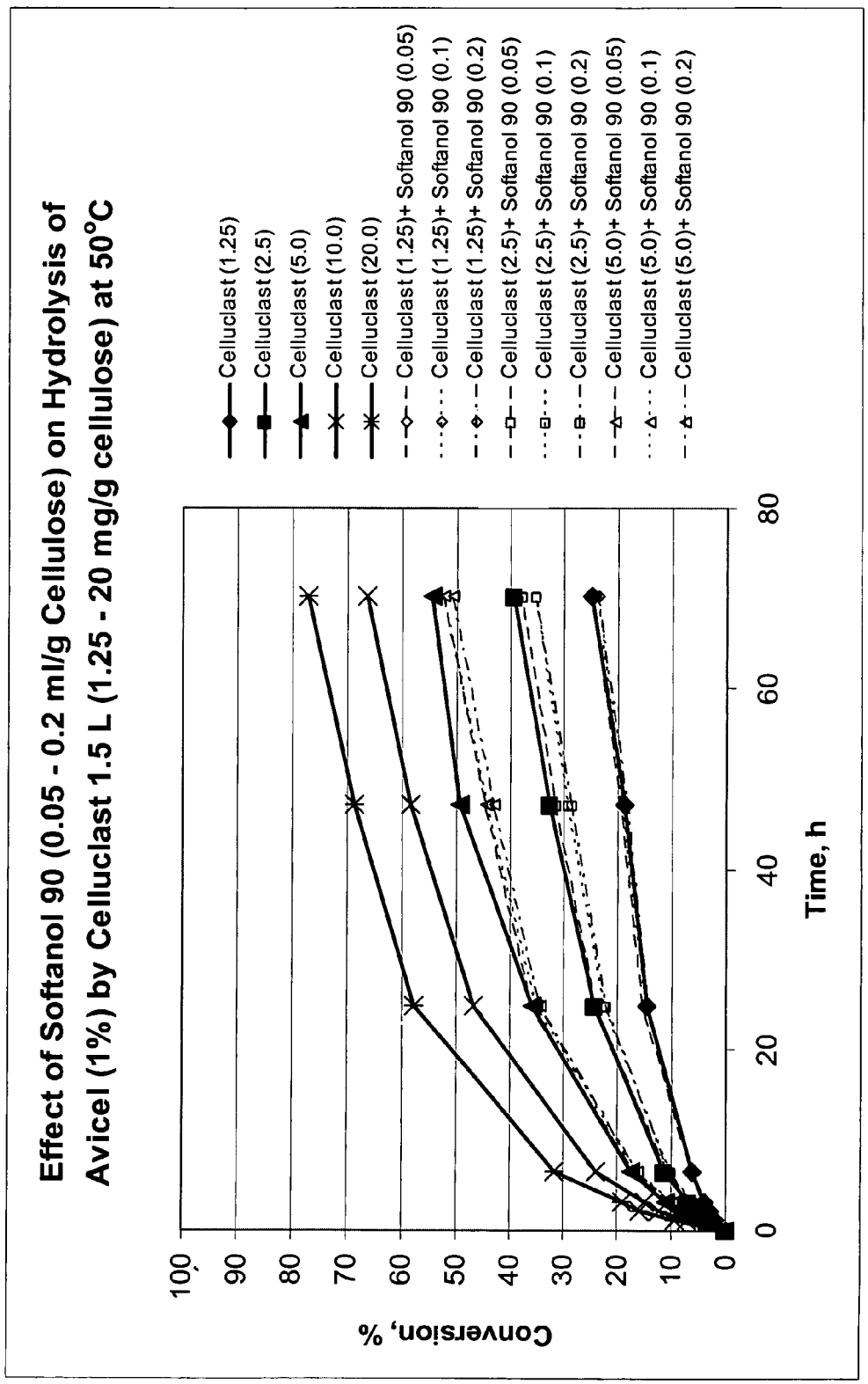
FIG. 28 shows the effect of Softanol® (0.05-0.2 ml/g cellulose) on hydrolysis of Avicel (1%) by Celluclast 1.5 L (1.25-20 mg/cellulose) at 50° C.

FIG. 28 shows that Softanol® 90 had no significant boosting effect on hydrolysis of Avicel under the above conditions.

Example 30

Enhanced Production of Sugars from PCS Using Non-Ionic Surfactants at 50° C.

Hydrolysis of water-washed/milled PCS (5% w/v on a dry weight basis) by cell-free filtered fermentation broth of *Aspergillus oryzae* beta-glucosidase (recombinantly produced in *Trichoderma reesei*) at 2 mg per g of PCS was carried out in the presence of various non-ionic surfactants (0.1 ml/g PCS) as shown in Table 5 in a 2-ml volume with intermittent stirring at pH 5.0, 50° C. for 71 hours. Samples were taken at different time-points and analyzed for reducing sugars as described in Example 18. The results were compared to a control reaction containing no surfactant.

Table 5 shows that addition of surfactants increased the 71-hour hydrolysis yield of reducing suger from 60% (no surfactant) to 63-19% (4-19% improvement).

TABLE 5

Effect of Non-Ionic Surfactants (0.1 ml/g PCS) on Hydrolysis of PCS (5%) by *Trichoderma reesei* Fermentation Broth with Expressed *Aspergillus oryzae* Beta-Glucosidase (2 mg/g PCS) at 50° C.

| Surfactant | 71-hour Conversion, % | Improvement at 71 hours, % |
|---|---|---|
| None | 60 | NA |
| Softanol ® 50 | 66 | 8.7 |

TABLE 5-continued

Effect of Non-Ionic Surfactants (0.1 ml/g PCS) on Hydrolysis of PCS (5%) by *Trichoderma reesei* Fermentation Broth with Expressed *Aspergillus oryzae* Beta-Glucosidase (2 mg/g PCS) at 50° C.

| Surfactant | 71-hour Conversion, % | Improvement at 71 hours, % |
|---|---|---|
| Softanol ® 90 | 72 | 18.8 |
| Softanol ® 120 | 69 | 14.8 |
| Softanol ® 200 | 71 | 18.3 |
| Lutensol ® AT50 | 71 | 18.3 |
| Lutensol ® AT80 | 69 | 13.8 |
| Tergitol ™ NP-9 | 66 | 10.2 |
| Novell ™ II TDA-6.6 | 70 | 16.5 |
| Novell ™ II TDA-8.5 | 69 | 14.4 |
| Brij ™ 35 | 70 | 16.1 |
| Brij ™ 56 | 70 | 16.5 |
| Brij ™ 97 | 63 | 3.9 |
| Brij ™ 98 | 71 | 18.4 |
| Pluronic ® F-68 | 71 | 18.1 |

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* TOP10 (pEJG113) | NRRL B-30695 | Oct. 17, 2003 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for degrading a lignocellulosic material, comprising:
    treating the lignocellulosic material with an effective amount of one or more cellulolytic enzymes in the presence of at least one surfactant selected from the group consisting of a secondary alcohol ethoxylate, fatty alcohol ethoxylate, and tridecyl ethoxylate, wherein the presence of the surfactant increases the degradation of the lignocellulosic material compared to the absence of the surfactant.

2. The method of claim 1, wherein the lignocellulosic material is selected from the group consisting of herbaceous material, agricultural residue, forestry residue, municipal solid waste, waste paper, and pulp and paper mill residue.

3. The method of claim 1, wherein the lignocellulosic material is corn stover.

4. The method of claim 1, wherein the one or more cellulolytic enzymes are selected from the group consisting of a cellulase, endoglucanase, cellobiohydrolase, and beta-glucosidase.

5. The method of claim 1, further comprising treating the lignocellulosic material with an effective amount of one or more enzymes selected from the group consisting of a hemicellulase, esterase, protease, laccase, peroxidase, or a mixture thereof.

6. The method of claim 5, wherein the esterase is a lipase, phospholipase, cutinase, or a mixture thereof.

7. The method of claim 1, wherein the method is a pretreatment process.

8. The method of claim 1, wherein the method is in a simultaneous saccharification and fermentation process (SSF).

9. The method of claim 1, wherein the method is in a hybrid hydrolysis and fermentation process (HHF).

10. The method of claim 1, further comprising recovering the degraded lignocellulosic material.

11. The method of claim 1, wherein the at least one surfactant is a secondary alcohol ethoxylate.

12. The method of claim 1, wherein the at least one surfactant is a fatty alcohol ethoxylate.

13. The method of claim 1, wherein the at least one surfactant is a tridecyl ethoxylate.

* * * * *